US010398514B2

(12) United States Patent
Ryan et al.

(10) Patent No.: US 10,398,514 B2
(45) Date of Patent: Sep. 3, 2019

(54) SYSTEMS AND METHODS FOR SENSORY AUGMENTATION IN MEDICAL PROCEDURES

(71) Applicant: Insight Medical Systems, Inc., Laguna Hills, CA (US)

(72) Inventors: Matthew William Ryan, Aliso Viejo, CA (US); Andrew Philip Hartman, Encinitas, CA (US); Nicholas van der Walt, Laguna Hills, CA (US); David Jacob Mayman, New York, NY (US)

(73) Assignee: Insight Medical Systems, Inc., Laguna Hills, CA (US)

( * ) Notice: Subject to any disclaimer, the term of this patent is extended or adjusted under 35 U.S.C. 154(b) by 0 days.

(21) Appl. No.: 15/897,559

(22) Filed: Feb. 15, 2018

(65) Prior Publication Data

US 2018/0168740 A1    Jun. 21, 2018

Related U.S. Application Data

(63) Continuation-in-part of application No. 15/674,749, filed on Aug. 11, 2017, now abandoned, and a
(Continued)

(51) Int. Cl.
*A61B 34/20* (2016.01)
*A61B 1/00* (2006.01)
(Continued)

(52) U.S. Cl.
CPC ............ *A61B 34/20* (2016.02); *A61B 1/0005* (2013.01); *A61B 1/00048* (2013.01);
(Continued)

(58) Field of Classification Search
CPC ......... A61B 34/10; A61B 34/20; A61B 34/25; A61B 90/37; A61B 2090/36–369; A61B 90/361
See application file for complete search history.

(56) References Cited

U.S. PATENT DOCUMENTS

2002/0075201 A1    6/2002  Sauer
2004/0019274 A1    1/2004  Galloway, Jr.
(Continued)

FOREIGN PATENT DOCUMENTS

WO    2005/088539 A2    9/2005
WO    2006/079211 A1    8/2006
(Continued)

OTHER PUBLICATIONS

PCT Search Report & Written Opinion dated May 23, 2018; Application No. PCT/US2018/018330.
(Continued)

*Primary Examiner* — Mark K Zimmerman
*Assistant Examiner* — Jonathan M Cofino
(74) *Attorney, Agent, or Firm* — Aurora Consulting LLC; Ashley Sloat

(57) ABSTRACT

The present invention provides a mixed reality surgical navigation system (10) to be worn by a user (106) during a surgical procedure comprising: a display device (104), to be worn by a user (106) during a surgical procedure, comprising a processor unit (102), a display generator (204), a sensor suite (210) having at least one camera (206) or depth sensor wherein the processing unit (102) creates a reference surface map (5804) of an exposed surface (5806) of an anatomical object (4204) with data received from the sensor suite (210); the processing unit (102) establishes a reference frame (5810) relative to the sensor suite (210) for the reference surface map (5804); orientation of the reference frame (5810) is established by creating additional surface maps (5834) of other anatomical features (5824) of the anatomical object (4204); the processing unit (102) tracks a pose of the anatomical object (4204) relative to the system (10) by creating a displaced surface map (5814) of the exposed surface (5806) and rotating and translating the
(Continued)

displaced surface map (5814) and reference frame (5810) to achieve a best fit to the reference surface map (5804).

24 Claims, 36 Drawing Sheets

Related U.S. Application Data continuation-in-part of application No. PCT/US2017/046438, filed on Aug. 11, 2017.

(60) Provisional application No. 62/375,483, filed on Aug. 16, 2016, provisional application No. 62/375,483, filed on Aug. 16, 2016.

(51) Int. Cl.
| | | |
|---|---|---|
| *A61B 34/00* | (2016.01) | |
| *A61B 34/10* | (2016.01) | |
| *A61B 90/00* | (2016.01) | |
| *A61B 1/317* | (2006.01) | |
| *A61B 90/30* | (2016.01) | |

(52) U.S. Cl.
CPC .............. *A61B 1/317* (2013.01); *A61B 34/10* (2016.02); *A61B 34/25* (2016.02); *A61B 90/36* (2016.02); *A61B 90/37* (2016.02); *A61B 34/76* (2016.02); *A61B 90/30* (2016.02); *A61B 90/361* (2016.02); *A61B 2034/108* (2016.02); *A61B 2034/2048* (2016.02); *A61B 2034/2055* (2016.02); *A61B 2034/2065* (2016.02); *A61B 2034/2068* (2016.02); *A61B 2090/365* (2016.02); *A61B 2090/368* (2016.02); *A61B 2090/371* (2016.02); *A61B 2090/3937* (2016.02)

(56) References Cited

U.S. PATENT DOCUMENTS

| | | |
|---|---|---|
| 2004/0181149 A1 | 9/2004 | Langlotz |
| 2005/0203380 A1 | 9/2005 | Sauer et al. |
| 2005/0281465 A1 | 12/2005 | Marquart |
| 2008/0202509 A1 | 8/2008 | Dillon |
| 2013/0123801 A1 | 5/2013 | Umasuthan |
| 2013/0150863 A1 | 6/2013 | Baumgartner |
| 2013/0237811 A1 | 9/2013 | Mihailescu |
| 2014/0022283 A1 | 1/2014 | Chan |
| 2014/0031668 A1 | 1/2014 | Mobasser |
| 2014/0369584 A1* | 12/2014 | Fan ..................... A61B 6/501 382/131 |
| 2016/0000518 A1* | 1/2016 | Thoranaghatte ........ G06F 3/017 703/11 |
| 2016/0183841 A1 | 6/2016 | Dulndam |
| 2016/0191887 A1 | 6/2016 | Casas |
| 2016/0324580 A1 | 11/2016 | Esterberg |

FOREIGN PATENT DOCUMENTS

| | | |
|---|---|---|
| WO | 2015/192117 A1 | 12/2015 |
| WO | 2017/185170 A1 | 11/2017 |
| WO | 2018/063528 A1 | 4/2018 |

OTHER PUBLICATIONS

Augmented Reality and Image Guided Robotic Surgery: Luc Soler, M.D.; https://www.youtube.com/watch?v=uVDxMR-47kU, last accessed Dec. 12, 2017.

Abstract for Surgical Navigation with a Head-Mounted Tracking System and Display; Sadda P; 2013.

The Emervence of Augmented Reality in Orthopaedic Surgery and Education; Dustin K. Baker; The Orthopaedic Journal at Harvard Medical School; Jun. 16, 2015.

Augmented Reality Navigation with Automatic Marker-Free Image Registration Using 3-D Image Overlay for Dental . . . , ResearchGate, Mar. 29, 2014, Wang et al.

An Inertial and Optiacal Sensor Fusion Approach for Six Degree of Freedom Pose Estimation; Sensors 2015; He et al.

Annex to Form PCT/ISA/206 Communication Relating to the Results of the Partial International Search dated Nov. 9, 2017; Application No. PCT/US2017/046438.

Anonymous: "Mixed reality—Wikipedia", Jun. 16, 2016, XP055417913, Retrieved from the Internet: URL: https://en.wikipedia.org/w/index.php?title=Mixed_reality&oldid=725636526 [retrieved on Oct. 23, 2017] abstract.

Anonymous: "Simultaneous localization and mapping—Wikipedia", Jul. 25, 2016, XP055418128, Retrieved from the Internet: URL: https://en.wikipedia.org/w/index.php?title=Simultaneouslocalization and mapping&oldid=731478358 [retrieved on Oct. 23, 2017] the whole document.

Copending U.S. Appl. No. 15/674,749, filed Aug. 11, 2017.
Copending U.S. Appl. No. 15/897,559, filed Feb. 15, 2018.
Copending PCT Application No. PCT/US2018/018330, Filed Feb. 15, 2018.

* cited by examiner

SYSTEMS AND METHODS FOR SENSORY AUGMENTATION IN MEDICAL PROCEDURES

CLAIM OF BENEFIT OF FILING DATE

This application is a continuation-in-part of U.S. application Ser. No. 15/674,749 filed Aug. 11, 2017 and Patent Cooperation Treaty Application No. PCT/US2017/046438 filed Aug. 11, 2017, both of which claim priority from U.S. Provisional Application Ser. No. 62/375,483 titled: "Systems and Methods of Sensory Augmentation in Medical Procedures" filed on Aug. 16, 2016; all of which are incorporated by reference in their entirety for all purposes.

FIELD OF INVENTION

The present invention relates to novel visualization and sensory augmentation devices, systems, methods and apparatus for positioning, localization, and situational awareness during medical procedures including but not limited to surgical, diagnostic, therapeutic and anesthetic procedures.

BACKGROUND INFORMATION

Current medical procedures are typically performed by a surgeon or medical professional with little or no assistance outside of the required tools to affect changes on the patient. For example, an orthopedic surgeon may have some measurement tools (e.g. rulers or similar) and cutting tools (e.g. saws or drills), but visual, audible and tactile inputs to the surgeon are not assisted. In other words, the surgeon sees nothing but what he or she is operating on, hears nothing but the normal communications from other participants in the operating room, and feels nothing outside of the normal feedback from grasping tools or other items of interest in the procedure. Alternatively, large console type navigation or robotic systems are utilized in which the display and cameras are located outside the sterile field away from the surgeon. These require the surgeon to repeatedly shift his or her gaze between the surgical site and the two-dimensional display. Also, the remote location of the cameras introduces line-of-sight issues when drapes, personnel or instruments obstruct the camera's view of the markers in the sterile field and the vantage point of the camera does not lend itself to imaging within the wound. Anatomic registrations are typically conducted using a stylus with markers to probe in such a way that the markers are visible to the cameras.

SUMMARY OF INVENTION

The present invention provides projection of feedback necessary for the procedure(s) visually into the user's field of view that does not require an unnatural motion or turning of the user's head to view an external screen. The augmented or virtual display manifests to the user as a natural extension or enhancement of the user's visual perception. Further, sensors and cameras located in the headpiece of the user have the same vantage point as the user, which minimizes line of sight obscuration issues associated with external cameras. 3D mapping of anatomic surfaces and features with the present invention and matching them to models from pre-operative scans are faster and represent a more accurate way to register the anatomy during surgery than current stylus point cloud approaches.

The present invention comprises a novel sensory enhancement device or apparatus generally consisting of at least one augmentation for the user's visual, auditory or tactile senses that assists in the conduct of medical procedures. Visual assistance can be provided in the form of real time visual overlays on the user's field of view in the form of augmented reality or as a replacement of the visual scene in the form of virtual reality. Auditory assistance can be provided in the form of simple beeps and tones or more complex sounds like speech and instruction. Tactile assistance can be provided in the form of simple warning haptic feedback or more complex haptic generation with the goal of guiding the user. In the preferred embodiments, the visual (augmented or virtual) assistance will be supplemented by audio or tactile or both audio and tactile feedback.

The present invention provides a mixed reality surgical navigation system comprising: a head-worn display device (e.g., headset or the like), to be worn by a user (e.g., surgeon) during surgery, comprising a processor unit, a display generator, a sensor suite having at least one tracking camera; and at least one visual marker trackable by the camera, is fixedly attached to a surgical tool; wherein the processing unit maps three-dimensional surfaces of partially exposed surfaces of an anatomical object of interest with data received from the sensor suite; the processing unit establishes a reference frame for the anatomical object by matching the three dimensional surfaces to a three dimensional model of the anatomical object; the processing unit tracks a six-degree of freedom pose (comprised of location and orientation) of the surgical tool with data received from the sensor suite; the processing unit communicates with the display to provide a mixed reality user interface comprising stereoscopic virtual images of desired features of the surgical tool and desired features of the anatomical object in the user's field of view.

The present invention further provides a method of using a mixed reality surgical navigation system for a medical procedure comprising: (a) providing a mixed reality surgical navigation system comprising (i) a head-worn display device comprising a processor unit, a display, a sensor suite having at least one tracking camera; and (ii) at least one visual marker trackable by the camera; (b) attaching the display device to a user's head; (c) providing a surgical tool having the marker; (d) scanning an anatomical object of interest with the sensor suite to obtain data of three-dimensional surfaces of desired features of the anatomical object; (e) transmitting the data of the three-dimensional surfaces to the processor unit for registration of a virtual three-dimensional model of the desired features of the anatomical object; (f) tracking the surgical tool with a six-degree of freedom pose with the sensor suite to obtain data for transmission to the processor unit; and (g) displaying a mixed reality user interface comprising stereoscopic virtual images of the features of the surgical tool and the features of the anatomical object in the user's field of view.

The present invention further provides a mixed reality user interface for a surgical navigation system comprising: stereoscopic virtual images of desired features of a surgical tool and desired features of an anatomical object of interest in a user's field of view provided by a mixed reality surgical navigation system comprising: (i) a head-worn display device comprising a processor unit, a display, a sensor suite having at least one tracking camera; and (ii) at least one visual marker trackable by the camera; wherein the mixed reality user interface is obtained by the following processes: (a) attaching the head-worn display device to a user's head; (b) providing a surgical tool having the marker; (c) scanning a desired anatomical object with the sensor suite to obtain data of three-dimensional surfaces of partially exposed surfaces of the anatomical object; (d) transmitting the data of the three-dimensional surfaces to the processor unit for registration of a virtual three-dimensional model of the features of the anatomical object; (e) tracking the surgical tool with a six-degree of freedom pose with the sensor suite to obtain data for transmission to the processor unit; and (f) displaying a mixed reality user interface comprising stereoscopic virtual images of the features of the surgical tool and the features of the anatomical object in the user's field of view.

BRIEF DESCRIPTION OF THE DRAWINGS

Some embodiments of the present invention are illustrated as an example and are not limited by the figures of the accompanying drawings, in which like references may indicate similar elements and in which.

DETAILED DESCRIPTION OF THE INVENTION

Figure 1:
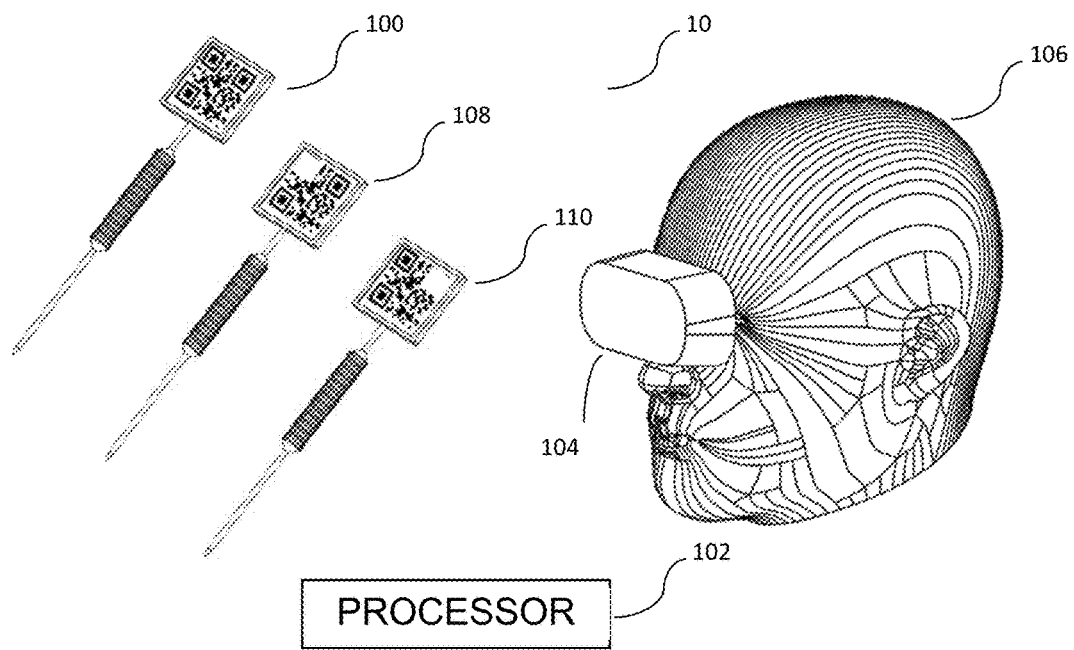
FIG. 1 is a diagrammatic depiction of an augmentation system in accordance to the principles of the present invention.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising", when used in this specification, specify the presence of stated features, steps, operations, elements, and/or components, and/or groups thereof.

Unless otherwise defined, all terms (including technical and scientific terms) used herein have the same meaning as commonly understood by one having ordinary skill in the art to which this invention belongs. It will be further understood that terms such as those defined in commonly used dictionaries should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and claims.

New sensory augmentation devices, apparatuses, and methods for providing data to assist medical procedures are discussed herein. In the following description, for purposes of explanation, numerous specific details are set forth in order to provide a thorough understanding of the present invention. It will be evident, however, to one skilled in the art that the present invention may be practiced without the specific details.

I. The Sensory Augmentation System

Referring to FIGS. 1, 2A-B, and 3, a sensory augmentation system 10 of the present invention is provided for use in medical procedures. The system 10 includes one or more visual markers (100, 108, 110), a processing unit 102, a sensor suite 210 having one or more tracking camera(s) 206, and a display device 104 having a display generator 204 that generates a visual display on the display device 104 for viewing by the user 106. The display device 104 is attached to a user 106 such that the display device 104 can augment his visual input. In one preferred embodiment, the display device 104 is attached to the user's 106 head. Alternatively, the display device 104 is located separately from the user 106, while still augmenting the visual scene. In one embodiment, each of the markers (100, 108, and 110) is distinct and different from each other visually so they can be individually tracked by the camera(s) 206.

Figure 2A:
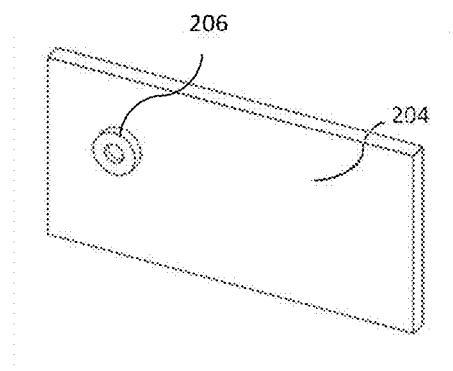
FIG. 2A shows a perspective front view of a diagrammatic depiction of a display device of the system of FIG. 1.
Figure 2B:
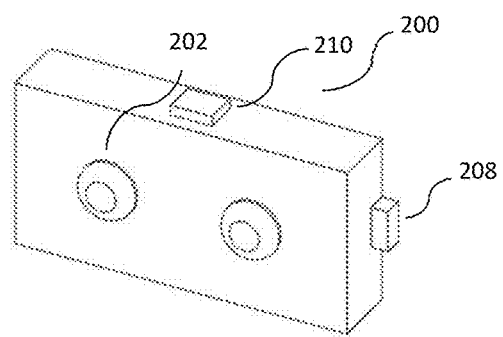
FIG. 2B shows a perspective back view of the display device of FIG. 2A.
Figure 3:
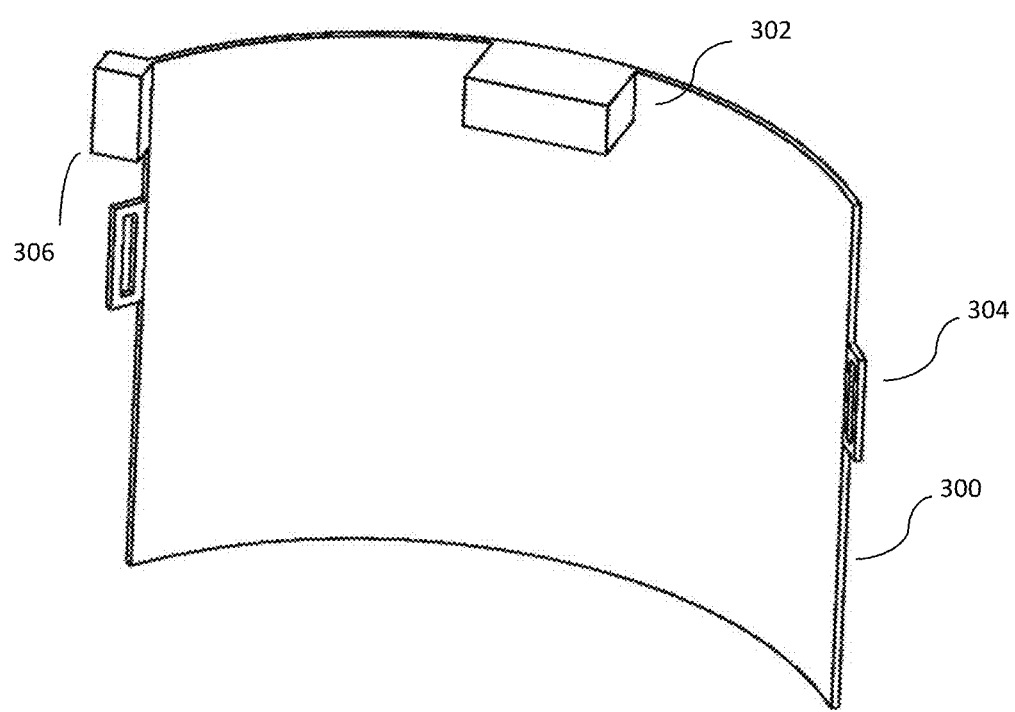
FIG. 3 is a diagrammatic depiction of another embodiment of the display device of the system of FIG. 1.

Referring to FIGS. 2A-2B, another exemplary embodiment of the display device 104 includes a visor housing 200 having optics 202 that allows focusing of the display generator's 204 video display onto the user's 106 eyes. The sensor suite 210 is attached or made part of the display device 104. The visor housing 200 includes an attachment mechanism 208 that allows attachment to the user's 106 head or face such that the alignment of the display device 104 to the user's 106 visual path is consistent and repeatable Referring to FIG. 3, another exemplary embodiment of the display device 104 includes a clear face shield 300 that allows a projection from the display generator 302 onto the shield 300 that overlays data and imagery within the visual path of the user's 106 eyes. The sensor suite 306 is attached or made part of the display device 104. The display device 104 further includes the attachment mechanism 304. The sensor suite 306 and the attachment mechanism 304 serve the same functions as the sensor suite 210 and the attachment mechanism 208 described above.

Figure 4:
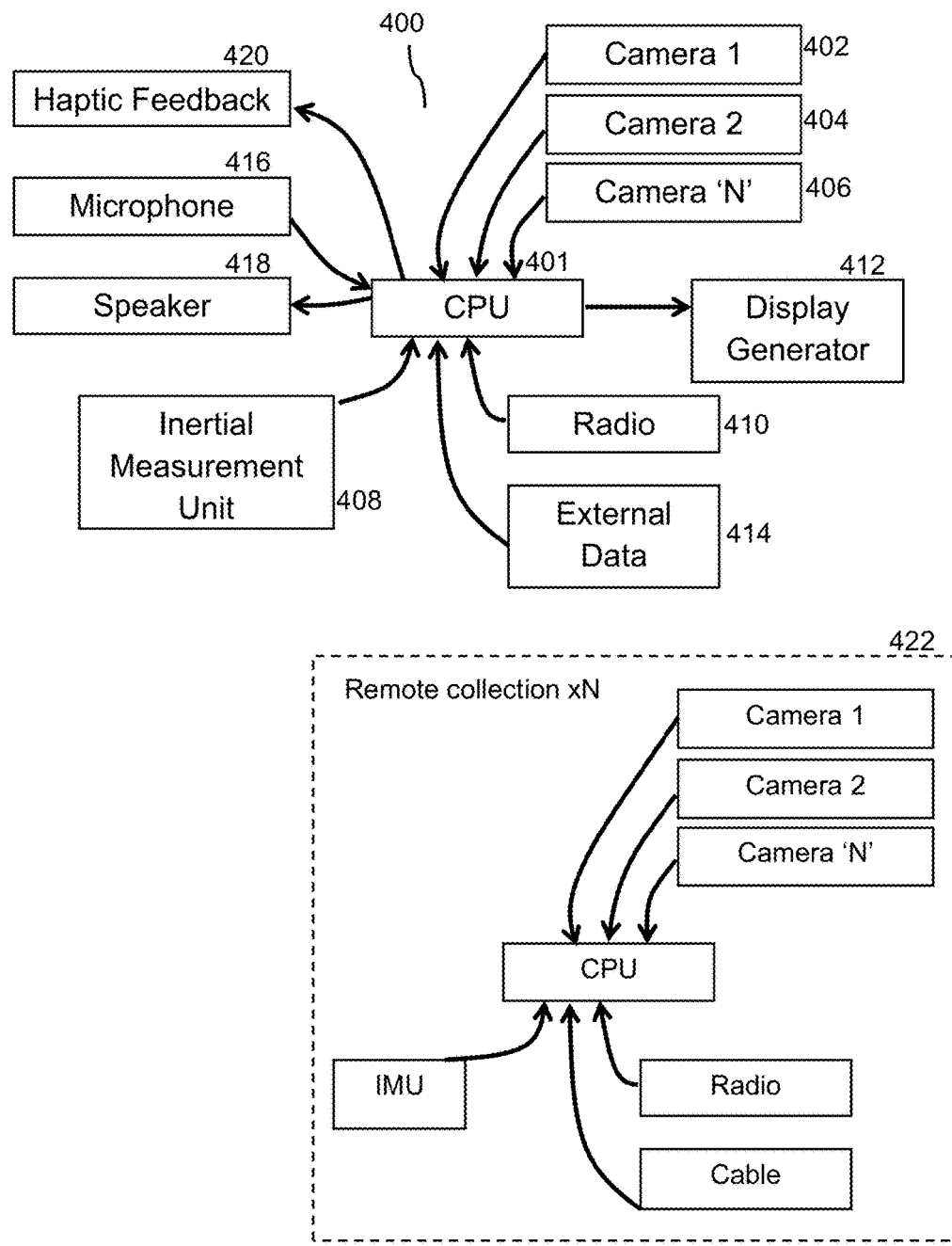
FIG. 4 is a schematic view of the electrical hardware configuration of system of FIG. 1.

Referring to FIG. 4 which shows the electronic hardware configuration of the system 10, the sensor suite (210, 306) not only includes one or more tracking cameras 402, 404, 406 (same as 206), it may optionally include an inertial measurement unit ("IMU") 408; a radio 410 for communication to other sensors or control units; a microphone 416 for voice activation of different display modes, including but not limited to removal of all displayed items for a clear field of view; one or more speakers 418 for audible alerts and other purposes; and haptic feedback 420 in the form of shaker motors, piezoelectric buzzers or other embodiments. The IMU 408 provides added orientation and localization data for an object that is not visually based. The IMU 408 can be used for, but is not limited to, generation of simultaneous localization and mapping ("SLAM") data from camera tracking and IMU's 408 data to determine non-marker specific room features that assist in localization and generation of surface maps of the objects of interest. Furthermore, the sensor suite(s) (400, 210, and 306) includes external data 414 as relayed by wire, radio or stored memory. External data 414 may optionally be in the forms of fluoroscopy imagery, computerized axial tomography ("CAT or CT") scans, positron emission tomography ("PET") scans or magnetic resonance imaging ("MRI") data, or the like. Such data may be combined with other data collected by the sensor suite (400, 210, and 306) to create augmentation imagery.

During operation of the system 10, the display generator 412 (same as 204 and 302) and the processing unit 401 (same as 102) are in electronic communication with the components described above for the sensor suite (210, 306). The processing unit 401 is a central processing unit ("CPU") that controls display management and algorithm prosecution. Referring to FIG. 4, the system 10 may optionally include one or more remote sensor suites 422. These remote sensor suites are physically located away from the display device 104. Each of these remote sensor suites 422 includes some or all of the components described above for the sensor suite (210, 306). It may also optionally include a separate and remote processing unit. The remote sensor suites 422 contribute data to the external data 414, which may be further processed by the processing unit 401 if desired. In another embodiment, the system 10 uses the remote suite(s) 422 to track not only the markers located in the field of regard, but also any marker(s) attached to the display unit 104 worn by the user 106, in order to localize the objects in the field of regard with respect to the user 106.

In one exemplary embodiment, the system 10 uses the sensor suite(s) (422, 210, 306) to create a three-dimensional point cloud of data representing objects in the workspace. This data can be used to create or match to already modeled objects for use in subsequent tracking, visualization or playback at a later time.

Furthermore, the system 10 can optionally overlay imagery and masks using art-disclosed means in order to obscure objects in the field of view, including but not limited to retractors or soft tissue around an exposure that are not the subject of the procedure to assist in highlighting the area and items of interest. In one embodiment, the external image can be projected with overlays in an augmented reality ("AR") mode. In another embodiment, the external image may be ignored and only computer-generated graphics may be used to display data to the user 106 in a virtual reality ("VR") mode. VR mode is supported if the display device 104 or part thereof is made opaque to block the external visual data or if some other method is used to emphasize to the user 106 that concentration should be on the imagery and not the external imagery.

Other alternative embodiments of the display device 104 would include, but not be limited to, holographic or pseudo holographic display projection into the field of regard for the user 106. Furthermore, the display device may optionally provide art-disclosed means of eye tracking that allows determination of the optimal displayed imagery with respect to the user's 106 visual field of view.

The system 10 can optionally use algorithms to discriminate between items in the field of view to identify what constitutes objects of interest versus objects not important to the task at hand. This could include, but is not limited to, identifying bony landmarks on a hip acetabulum for use in comparison and merge with a pre-operative scan in spite of soft tissue and tools that are visible in the same field of regard.

Figure 5:
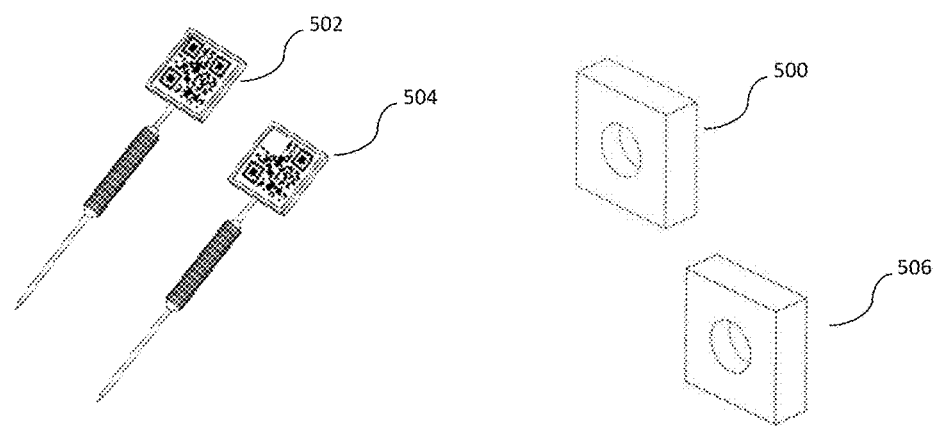
FIG. 5 is a diagrammatic depiction of markers and cameras of the system of FIG. 1.

Referring to FIG. 5, the one or more cameras 500, 506 of the sensor suites (400, 422, 210, and 306) and the one or more visual markers 502, 504 are used to visually track a distinct object (e.g., a surgical tool, a desired location within an anatomical object, etc.) and determine attitude and position relative to the user 106. In one embodiment, each of the one or more markers is distinct and different from each other visually. Standalone object recognition and machine vision technology can be used for marker recognition. Alternatively, the present invention also provides for assisted tracking using IMUs 408 on one or more objects of interest, including but not limited to the markers 502, 504. Please note that the one or more cameras 500, 506 can be remotely located from the user 106 and provide additional data for tracking and localization.

Optimal filtering algorithms are optionally used to combine data from all available sources to provide the most accurate position and orientation data for items in the field of regard. This filter scheme will be able to accommodate events including but not limited to occlusions of the camera(s) field(s) of view, blood, tissue, or other organic temporary occlusions of the desired area of interest, head movement or other camera movement that move the camera(s) field(s) of view away from the area of interest, data drop outs, and battery/power supply depletion or other loss of equipment.

Referring to FIGS. 36A-B, 37A-B, 38A-B, and 39-41A-B, another exemplary embodiment of the display device 104 is an AR headset 3600. The AR headset 3600 is used in various sterile surgical procedures (e.g., spinal fusion, hip and knee arthroplasty, etc.). The AR headset 3600 is clamped on the head of a surgeon 3602 (i.e., user 106) by adjusting a head strap 3604 by turning a thumb wheel 3606. A transparent protective face shield 3608 is optionally attached to the device 3600 by attachment to Velcro strips 3610. Alternatively, attachment may be via adhesive, magnetic, hooks or other art-disclosed attachment means. A coupling feature 3612 is present for attachment of a surgical helmet 3700 both mechanically and electrically to the AR headset 3600. The surgical helmet 3700 is optionally connected to a surgical hood (not shown) that provides full body coverage for the surgeon 3602. Full body coverage is useful for certain surgical procedures such as hip and knee arthroplasty or the like. If the surgical helmet 3700 is to be attached to a surgical hood, then a fan draws air in through the surgical hood into air inlet 3702 and is circulated under the surgical hood and helmet to cool the surgeon 3602 and prevent fogging of the optical components. A chin piece 3704 spaces the helmet 3700 (and if applicable, the attached surgical hood) away from the surgeon's 3602 face. The location of the surgical helmet 3700 relative to the AR headset 3600 is designed to allow unobstructed view of the surgical site for the surgeon 3602 and all cameras and sensors. The surgical helmet 3700 includes the necessary features to attach to and interface with the surgical hood. A flexible cord 3706 connects the AR headset 3600 to a hip module 3708, which can be worn on the surgeon's 3602 belt. A replaceable battery 3800 inserts into the hip module 3708.

Figure 39:
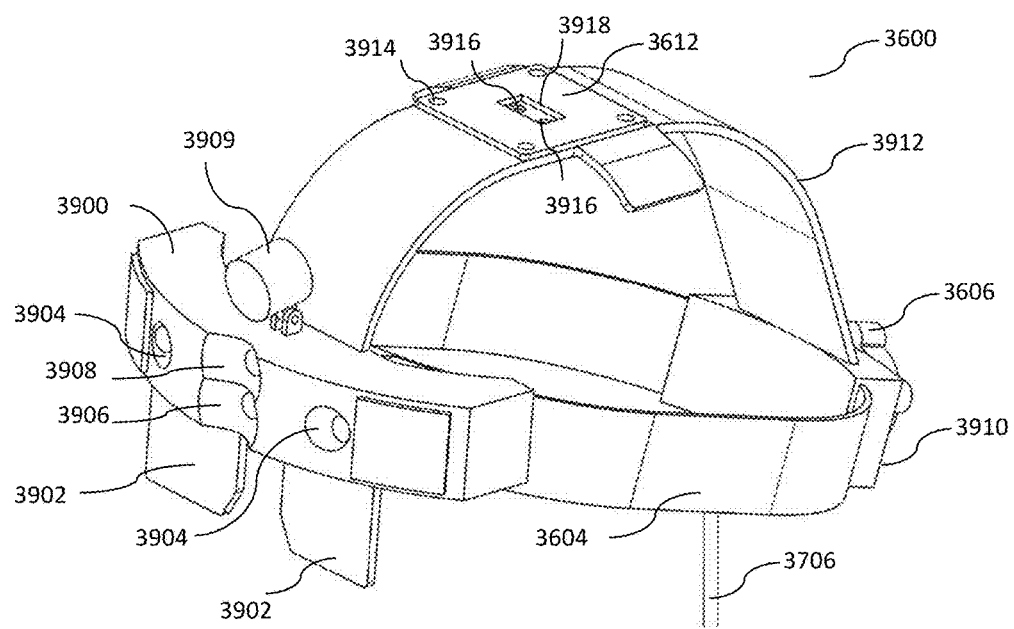
FIG. 39 shows a perspective front view of the AR headset shown in FIG. 36A.

Referring to FIG. 39, the AR headset 3600 includes a display section 3900 having a pair of see through optical displays 3902 for visual augmentation and two tracking cameras 3904 for performing tracking and stereoscopic imaging functions including two-dimensional and three-dimensional digital zoom functions. A depth sensor 3906 and a structured-light projector 3908 are included in the display section 3900. It is preferred that the depth sensor 3906 and the projector 3908 are located in the middle of the display section 3900. A surgical headlight 3909 is optionally mounted to the display section 3900 and may be electrically connected the AR headset 3600 to allow its brightness to be controlled by the software of the AR headset 3600 including by voice command. This feature may be deployed, for example, to dim or switch off the surgical headlight when in mixed reality mode to allow better visualization of virtual content against a bright background. It may also be adjusted to optimize optical tracking which at times can be impaired by high contrast illumination of targets or by low ambient lighting. In another exemplary embodiment, the operating room lights may be controlled wirelessly by the software of the AR headset 3600 for the same reasons.

Figure 40:
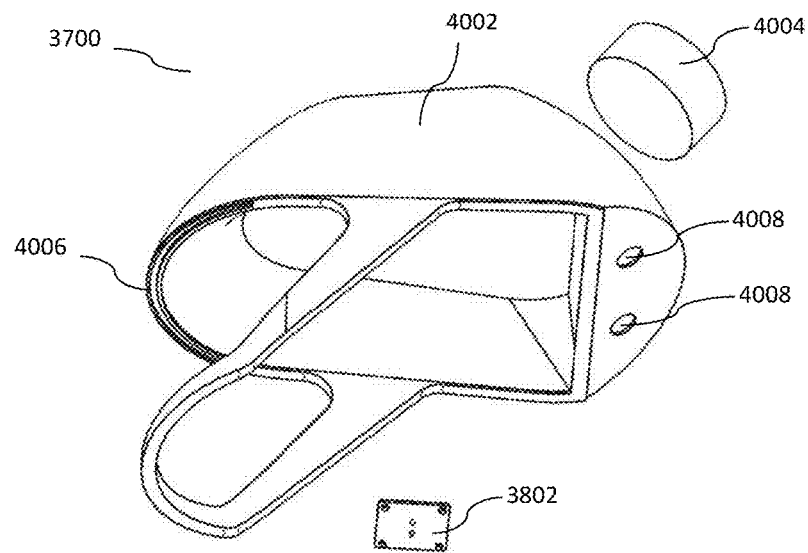
FIG. 40 is an exploded view of the surgical helmet shown in FIG. 37A.

Referring to FIGS. 39-40, the rear section 3910 of the AR headset 3600 may optionally contain the heat-generating and other components of the circuitry such as the microprocessor and internal battery. The arch-shaped bridge section 3912 and the head strap 3604 of the AR headset 3600 mechanically connect the rear section 3910 to the display section 3900. A portion of the bridge section 3912 is flexible to accommodate size adjustments. The bridge section 3912 may include wiring or a flexible circuit board to provide electrical connectivity between the display section 3900 and the rear section 3910. The bridge section 3912 includes the coupling feature 3612, which is a ferromagnetic plate with a plurality of locating holes 3914 and an aperture 3918, which provides access to two electrical contacts 3916 for powering the fan of the surgical helmet 3700. In alternative embodiments, the coupling feature 3612 can be other art-disclosed means such as Velcro, latches or threaded fasteners or the like. The coupling feature 3612 may optionally include a vibration isolation mount to minimize transmission of mechanical noise from the fan of the surgical helmet 3700 to the AR headset 3600, which can be detrimental to tracking performance. The fan 4004 may be software controlled allowing it to be slowed or shut down to minimize the generation of mechanical noise. It may also be controlled by the surgeon 3602 using voice commands. A flexible cord 3706 connects the rear section 3910 to the hip module 3708.

Referring to FIG. 40, the surgical helmet 3700 includes a hollow shell 4002 into which a fan 4004 draws air which is exhausted through various vents in the shell to provide cooling air for the surgeon. A brim vent 4006 provides airflow over the visor of the surgical hood and rear vents 4008 provide cooling air to the rear including to the rear section 3910 of the AR headset 3600.

Figures 41A, 41B:
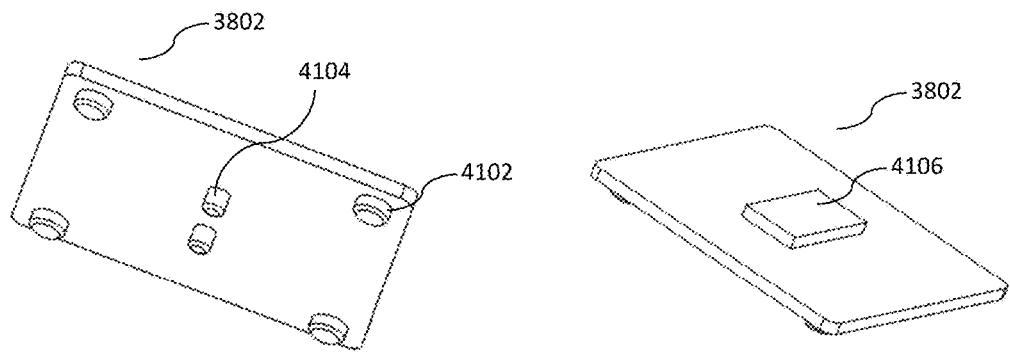
FIG. 41A is a perspective bottom view of the electromechanical coupling plate shown in FIG. 40.
FIG. 41B is a perspective top view of the electromechanical coupling plate shown in FIG. 40.

Referring to FIGS. 41A-B, the coupling plate 3802 includes a plurality of bosses 4102 for location with the holes 3914 in the AR headset 3600. The coupling plate 3802 also includes spring-loaded electrical contacts 4104, which connect with the electrical contacts 3916 of the AR headset 3600 to provide power to the fan 4004. The coupling plate 3802 further includes a magnet 4106, which provides a mechanical retention force between the coupling plate 3802 and the coupling feature 3612.

In an exemplary embodiment, the AR headset 3600 is optionally used as a system for reporting device complaints or design feature requests. The user interface can have a menu option or voice command to initiate a report at the time that it occurs. This would activate voice and video camera recording allowing the user 106 to capture and narrate the complaint in 3D while the issue is occurring. The user 106 terminates complaint with voice or selecting an option. The complaint record is compressed and transmitted to the company via the internet wirelessly providing complaint handling staff excellent data to be able to "re-live" the situation first hand for better diagnosis. Artificial intelligence can be used to parse and aggregate the complaint material to establish patterns and perform statistical analysis. The same sequence can be used to connect to live technical support during the procedure with the exception that the data stream is transmitted real-time.

II. Pre-Operative Procedures

The present invention can be used for pre-operative tasks and surgical procedures. For example, an alternate general surgical procedure that includes possible pre-operative activities is now described. First, a scan of the region of interest of the patient such as CT or MRI is obtained. If possible, the patient should be positioned in a way that approximates positioning during surgery. Second, segmentation of the scan data is performed in order to convert it into three-dimensional models of items of interest including but not limited to: teeth and bony structures, veins and arteries of interest, nerves, glands, tumors or masses, implants and skin surfaces. Models are segregated so that they can later be displayed, labeled or manipulated independently. These will be referred to as pre-operative models. Third, pre-operative planning is performed (optionally using VR for visualization and manipulation of models) using models to identify items including but not limited to: anatomic reference frames, targets for resection planes, volumes to be excised, planes and levels for resections, size and optimum positioning of implants to be used, path and trajectory for accessing the target tissue, trajectory and depth of guidewires, drills, pins, screws or instruments. Fourth, the models and pre-operative planning data are uploaded into the memory of the display device 104 prior to or at time of surgery. This uploading process would most conveniently be performed wirelessly via the radio.

Fifth, the patient is prepared and positioned for surgery. During surgery, the surgical site is ideally be draped in a way that maximizes the visualization of skin surfaces for subsequent registration purposes. This could be achieved by liberal use of Ioban. It would be beneficial to use a film like Ioban that fluoresced or reflected differently when targeted by a specific LED or visible light emitter in a broad illumination, point or projected pattern. This film may also have optical features, markers or patterns, which allowed for easy recognition by the optical cameras of the headpiece.

Sixth, after the patient has been prepped and positioned for surgery, the system 10 (e.g., via the AR headset 3600) scans the present skin envelope to establish its present contour and creates pre-operative 3D models available for user 106 to see on the display device 104. The preferred method is to project a grid or checkerboard pattern in infrared ("IR") band that allows for determination of the skin envelope from the calculated warp/skew/scale of the known image. An alternate method is to move a stylus type object with a marker attached back and forth along exposed skin, allowing the position and orientation track of the stylus and subsequent generation of the skin envelope. Optionally, the skin model is displayed to the user 106, who then outlines the general area of exposed skin, which has been scanned. An optimum position and orientation of the pre-operative skin model is calculated to match the present skin surface. The appropriate pre-operative models are displayed via the display device 104 to the user 106 in 3D. Optionally, the user 106 may then insert an optical marker into a bone of the patient for precise tracking. Placement of this marker may be informed by his visualization of the pre-operative models. The position and orientation of pre-operative models can be further refined by alternative probing or imaging including, but not limited to ultrasound.

Seventh, during surgery, the user 106 using the system 10 with the display device 104, can see the pre-operative planning information and can track instruments and implants and provide intraoperative measurements of various sorts including but not limited to depth of drill or screw relative to anatomy, angle of an instrument, angle of a bone cut, etc.

Figure 8:
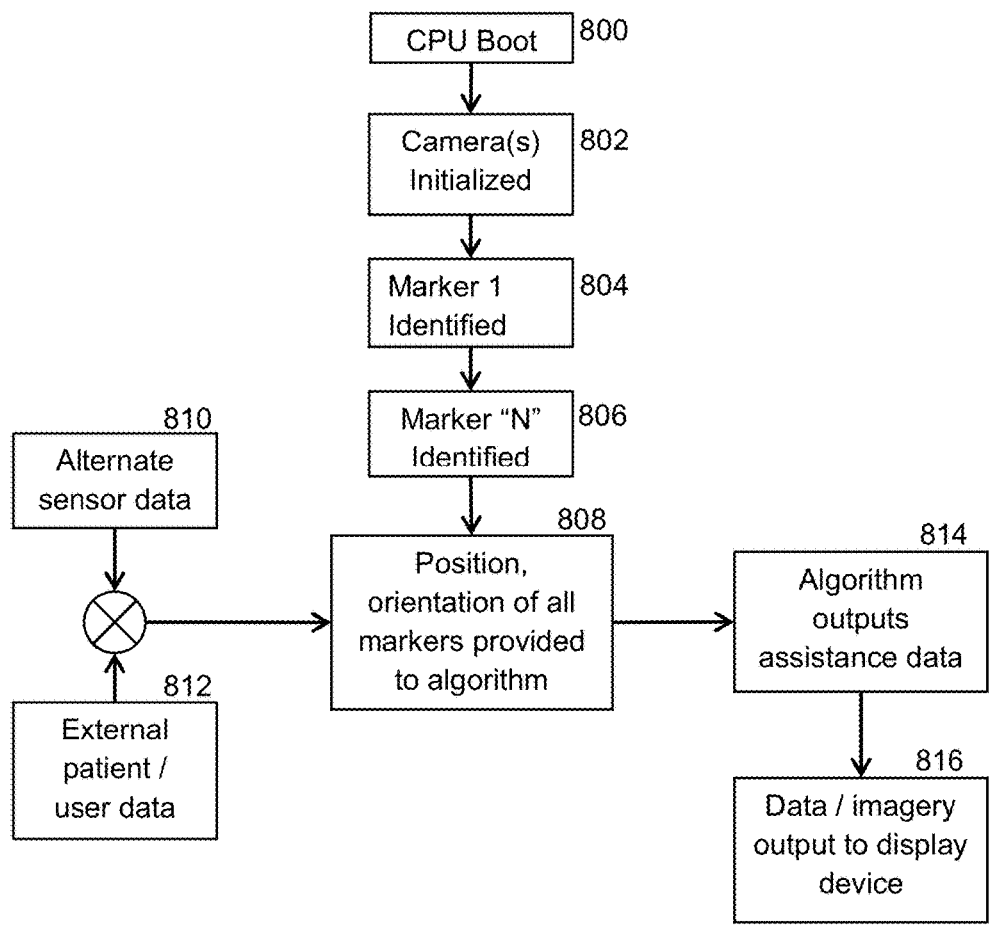
FIG. 8 is a flowchart showing the operational processes of the system of FIG. 1 during a medical procedure.

Referring to FIG. 8, an exemplary embodiment of the operational flow during a procedure using the system 10 is presented. In this embodiment, the CPU 401 boots (800) and initializes one or more cameras 402, 404, 406 (802). When in the field of view of the camera(s) 402, 404, 406, the first marker 100 is located and identified (804), followed by subsequent markers 108, 110 (806). The track of these markers 100, 108, 110 provides position and orientation relative to each other as well as the main camera locations (808). Alternate sensor data from sensors such as IMUs and cameras from the remote sensor suites 422 (810) can be optionally incorporated into the data collection. Further, external assistance data (812) about the patient, target, tools, or other portions of the environment may be optionally incorporated for use in the algorithms. The algorithms used in the present invention are tailored for specific procedures and data collected. The algorithms output (814) the desired assistance data for use in the display device (816).

III. Hip Replacement Procedures

Figure 6:
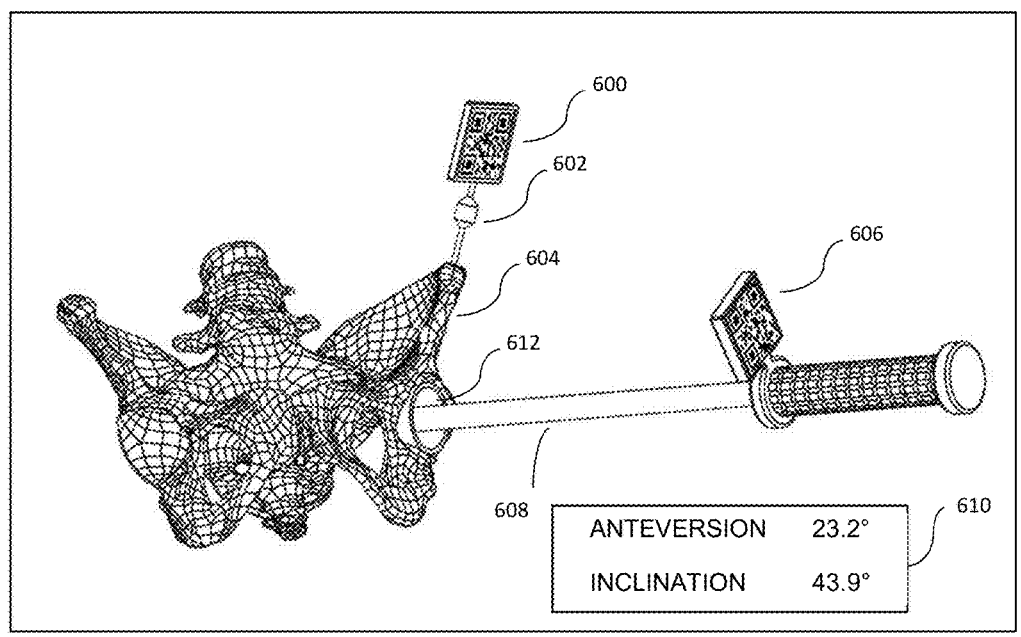
FIG. 6 is a diagrammatic depiction of a mixed reality user interface image ("MXUI") provided by system of FIG. 1 during positioning of an acetabular shell in a hip replacement procedure showing a virtual pelvis.

In one exemplary embodiment of the present invention and referring to FIG. 6, the system 10 is used for hip replacement surgery wherein a first marker 600 is attached via a fixture 602 to a pelvis 604 and a second marker 606 is attached to an impactor 608. The user 106 can see the mixed reality user interface image ("MXUI") shown in FIG. 6 via the display device 104. The MXUI provides stereoscopic virtual images of the pelvis 604 and the impactor 604 in the user's field of view during the hip replacement procedure.

The combination of markers (600, 606) on these physical objects, combined with the prior processing and specific algorithms allows calculation of measures of interest to the user 106, including real time version and inclination angles of the impactor 608 with respect to the pelvis 604 for accurate placement of acetabular shell 612. Further, measurements of physical parameters from pre- to post-operative states can be presented, including but not limited to change in overall leg length. Presentation of data can be in readable form 610 or in the form of imagery including, but not limited, to 3D representations of tools or other guidance forms.

Figure 7:
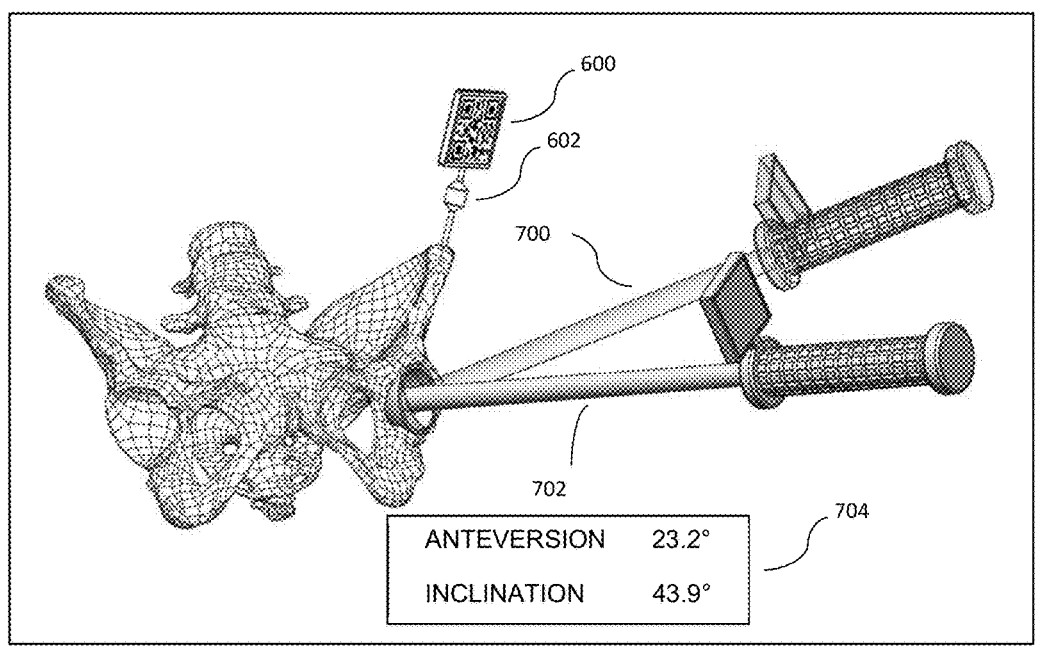
FIG. 7 is a diagrammatic depiction of a MXUI provided by system of FIG. 1 during positioning of an acetabular shell in a hip replacement procedure showing a virtual pelvis and virtual acetabular impactor.

FIG. 7 depicts an alternate view of the MXUI previously shown in FIG. 6, wherein a virtual target 700 and a virtual tool 702 are presented to the user 106 for easy use in achieving the desired version and inclination. In this embodiment, further combinations of virtual reality are used to optimize the natural feeling experience for the user by having a virtual target 700 with actual tool 702 fully visible or a virtual tool (not shown) with virtual target fully visible. Other combinations of real and virtual imagery can optionally be provided. Presentation of data can be in readable form 704 or in the form of imagery including but not limited to 3D representations of tools or other guidance forms.

Figure 9:
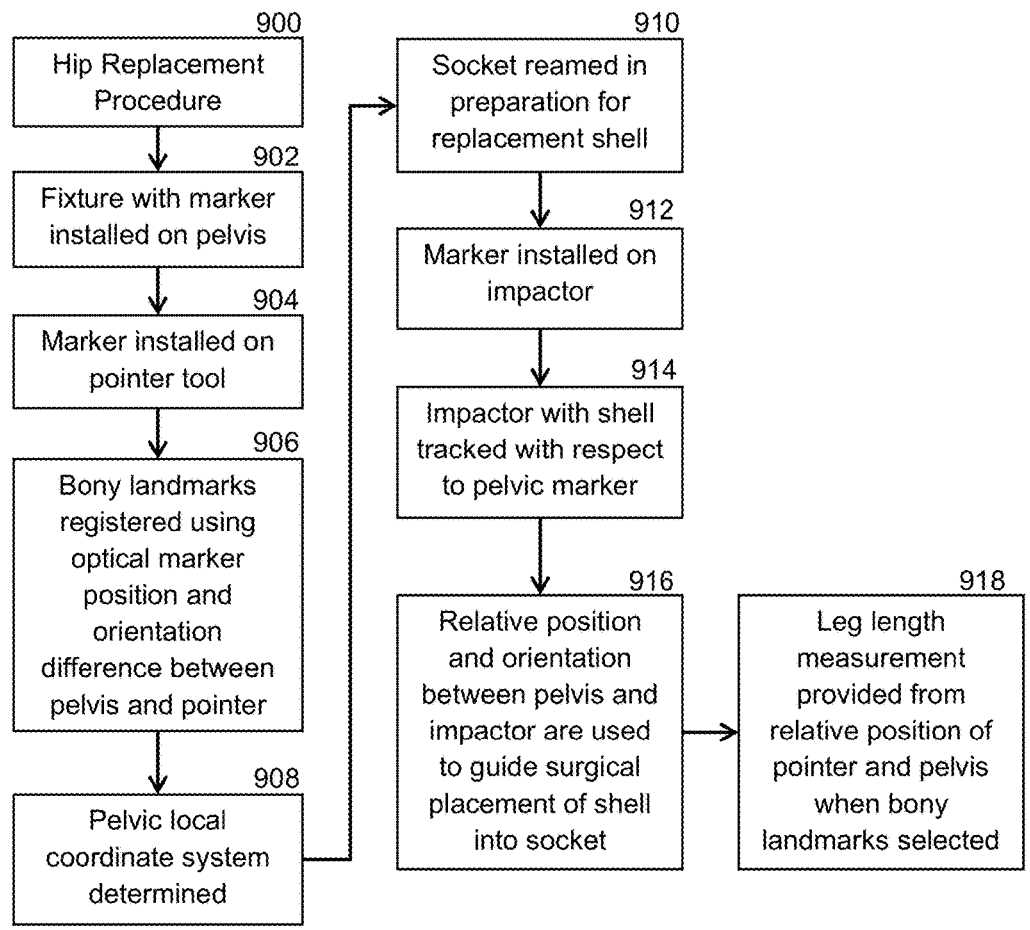
FIG. 9 is a flowchart showing a method of using the system of FIG. 1 to perform a hip replacement procedure in accordance to the principles of the present invention.

Referring to FIG. 9, the present invention further provides a method of using the system 10 to perform a hip replacement procedure (900) in which a hip bone has the socket reamed out and a replacement cup is inserted for use with a patient's leg. In this embodiment, a first marker (e.g., 100, 108, or 110, etc.) is installed on a fixture of known dimensions with respect to the marker and this fixture is installed on the hip bone of a patient (902). A second distinct marker (e.g., 100, 108, or 110, etc.) is installed on a pointing device of known dimensions with respect to the first marker (904). Bony landmarks or other anatomic landmarks position and orientation relative to the hip fixture are registered using the optical markers and the position/orientation difference between the hip and the pointer (906). These points are used to determine a local coordinate system (908). The pointer is used to determine position and orientation of the femur before the femur is dislocated and the acetabulum of the hip bone is reamed to make room for the replacement shell (910). An impactor with replacement shell installed on it has a third distinct marker installed with known dimensions of the impactor (912). The impactor with shell is tracked per the previously described algorithm with respect to the hip marker (914). The relative position and orientation between the hip marker and impactor are used to guide surgical placement of the shell via AR or VR display into the socket at a desired position and angle per medical requirement for the patient (916). The change in leg length can also be calculated at this point in the procedure using the marker position and orientation of the replaced femur (918). Another embodiment augments this procedure with pre-operative CT data to determine component positioning. Another embodiment uses the display output in an AR or VR manner to determine the femoral head cut. Another embodiment uses the data to place screws in the acetabulum.

The coordinate reference frame of the table or support on which the patient lies is desirable in some implementations. Table alignment with respect to ground, specifically gravity, can be achieved as follows. The IMU (from each of the sensor suites such as the one located within the AR headset 3600) provides the pitch and roll orientation of the display device 104 with respect to gravity at any given instant. Alternatively, SLAM or similar environment tracking algorithms will provide the pitch and roll orientation of the display device 104 with respect to gravity, assuming most walls and features associated with them are constructed parallel to the gravity vector. Separate from the display device's 104 relationship between to gravity, the table orientation may be determined by using the stylus to register three (3) independent points on the table. With these three points selected in the display device 104 coordinate frame, the table roll and pitch angles with respect to gravity can then be determined as well. Alternatively, the table may be identified and recognized using machine vision algorithms to determine orientation with respect to gravity. The alignment of the patient spine relative to the display device 104, and therefore any other target coordinate systems such as defined by the hip marker, in pitch and roll is now known. To provide a yaw reference, the stylus can be used in conjunction with the hip marker to define where the patient head is located, which provides the direction of the spine with respect to him. Alternatively, image recognition of the patients head can be used for automatic determination. Ultimately, the roll, pitch and yaw of the table and/or patient spine are now fully defined in the display device 104 and all related coordinate systems.

Figure 11:
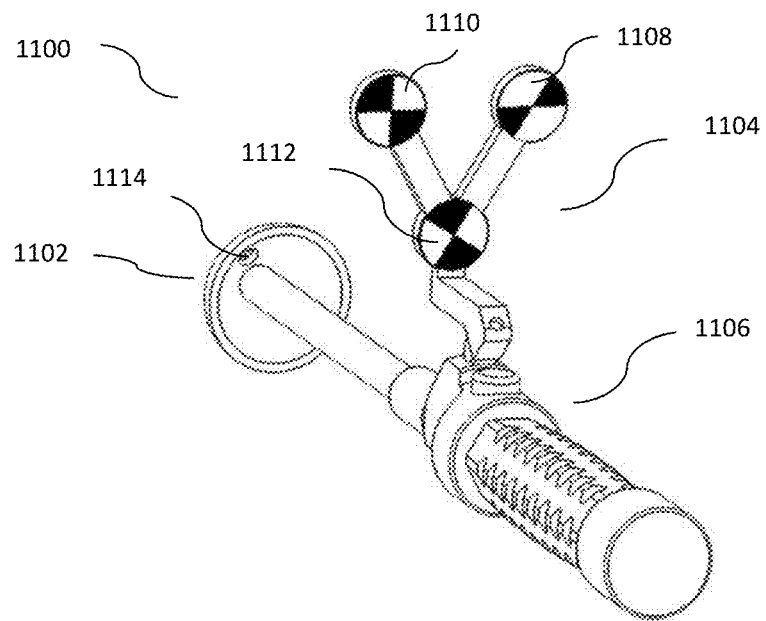
FIG. 11 shows a perspective view of a diagrammatic depiction of a hip impactor assembly including an acetabular shell and an optical marker.
Figure 12:
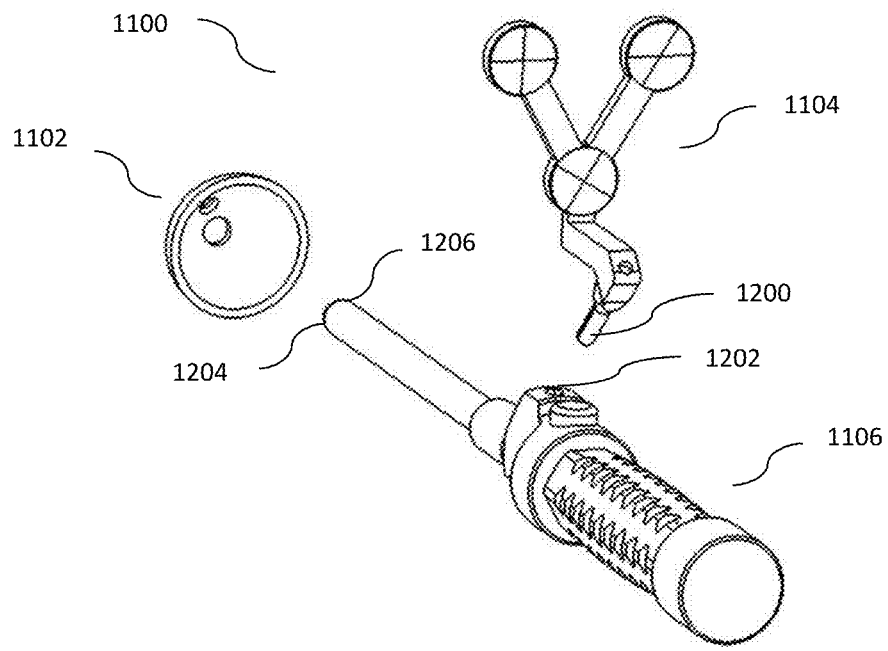
FIG. 12 shows an exploded view of the hip impactor assembly shown in FIG. 11.

Referring to FIGS. 11-12, the system 10 may optionally include a hip impactor assembly 1100 for use in hip arthroplasty procedures. The assembly includes an acetabular shell 1102, and an optical marker 1104 (same as 100, 108, 110, 502, 504, 600, 606, 804, 806, 904, 912 described above) assembled to an acetabular impactor 1106. FIG. 12 depicts an exploded view of the assembly 1100 illustrating how the optical marker 1104 attaches to the impactor 1106 in a reproducible way by insertion of an indexed post 1200 into an indexed hole 1202. The acetabular shell 1102 assembles reproducibly with the impactor 1106 by screwing onto a threaded distal end 1204 of the impactor and seating on a shoulder 1206. The marker 1104 includes a first fiducial 1108, a second fiducial 1110 and a third fiducial 1112; each having adjacent regions of black and white wherein their boundaries form intersecting straight lines. Algorithms in the AR headset 3600 are used to process the images from the stereoscopic cameras (3904) to calculate the point of intersection of each fiducial (1108, 1110, 1112) and thereby determine the six-degrees of freedom pose of the marker 1104. For the purpose of this specification, "pose" is defined as the combination of position and orientation of an object. The fiducials (1108, 1110, and 1112) can be created by printing on self-adhesive sticker, by laser-etching the black regions onto the surface of white plastic material or alternative methods. The shell contains a fixation hole 1114 through which a screw is optionally used to fixate the shell 1102 to the bone of the acetabulum.

Figures 13A, 13B:
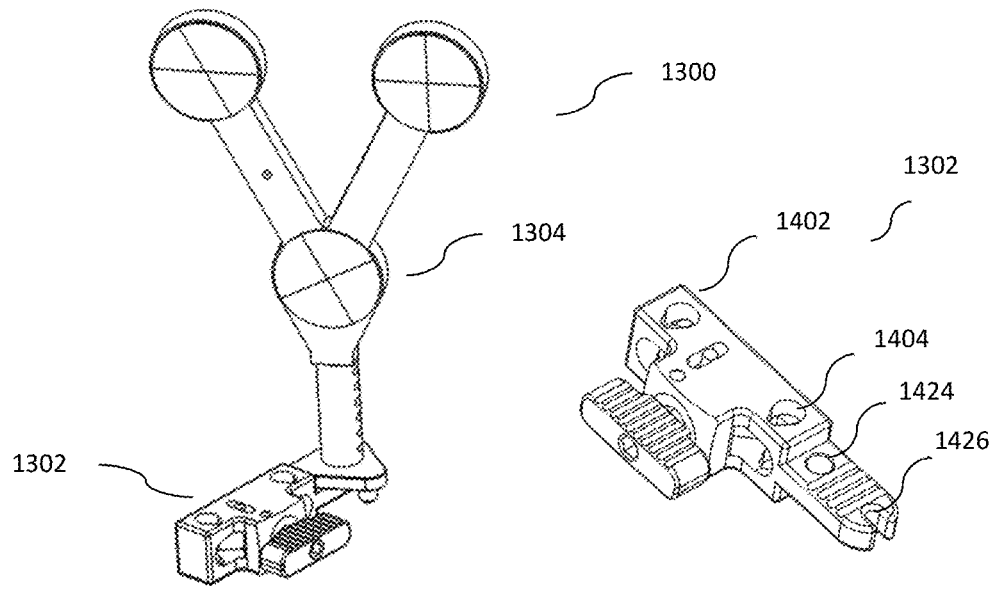
FIG. 13A shows a perspective view of a diagrammatic depiction of an anatomy marker assembly that is optionally included in the system of FIG. 1.
FIG. 13B shows a perspective view of a clamp assembly of the anatomy marker shown in FIG. 13A.
Figure 14:
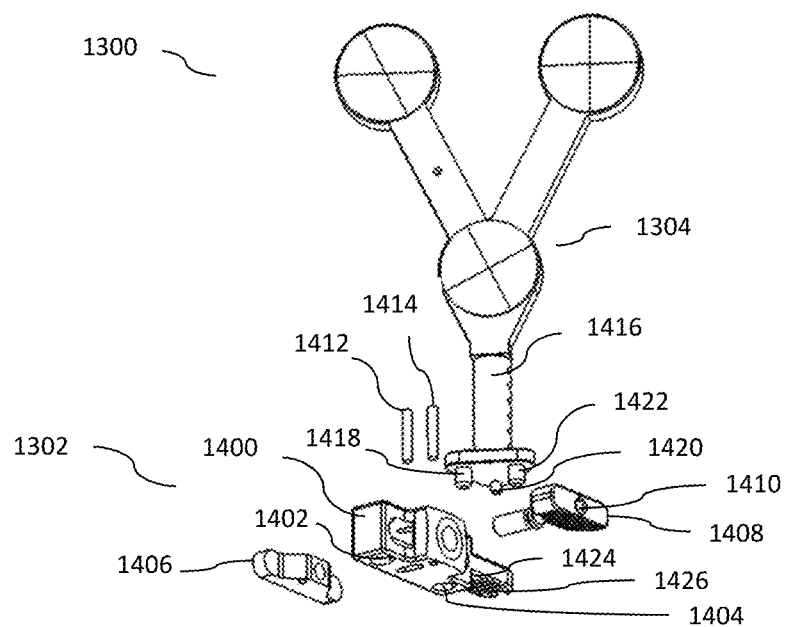
FIG. 14 shows an exploded view of the anatomy marker assembly shown in FIG. 13A.

In another exemplary embodiment and referring to FIGS. 13A-B and 14, the system 10 optionally includes an anatomy marker assembly 1300 comprised of a clamp assembly 1302 and an optical marker 1304. The clamp assembly 1302 includes a base 1400, a first teardrop-shaped hole 1402, and a second teardrop-shaped hole 1404. Fixation pins (not shown) which have been fixed to the bone can be inserted through the teardrop shaped holes (1402, 1404) and clamped between a clamp jaw 1406 and the body 1400 thereby fixing the clamp assembly 1302 to the pins and therefore to the bone. A clamp screw 1408 engages threads in the jaws and is used to tighten the assembly 1302 onto the pins. A hexagonal hole 1410 allows a hex driver to be used to tighten the assembly 1302. A first retaining pin 1412 and a second retaining pin 1414 prevent disassembly of the clamp assembly 1302. A marker body 1416 has a first locating post 1418, as second locating post 1420 and a third locating post 1422 which provide location to the base 1400 by engaging two locating posts with a locating hole 1424 and locating slot 1426 in the base. The design provides for two possible rotational positions of the marker 1304 which allows the marker 1304 to be oriented relative to the cameras (e.g., 3904) in the display device 104 (e.g., the AR headset 3600) for optimal tracking. The marker body 1416 encapsulates a magnet (not shown) which provides sufficient holding force to the base 1400.

Figure 15:
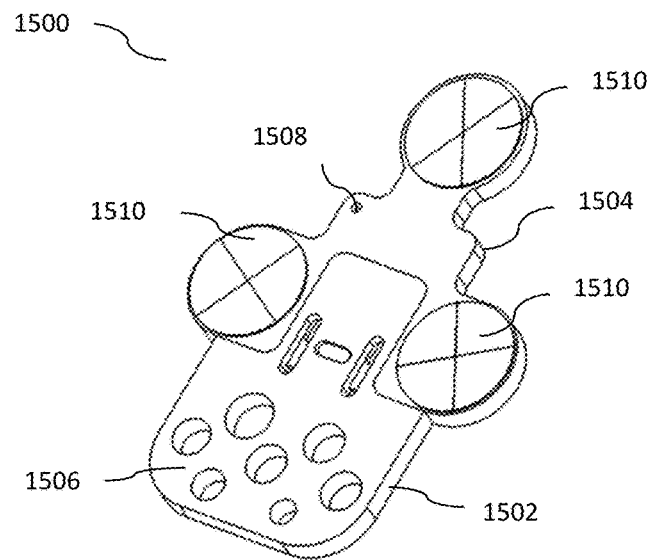
FIG. 15 shows a perspective view of a diagrammatic depiction of a calibration assembly that is optionally included in the system of FIG. 1.
Figure 16:
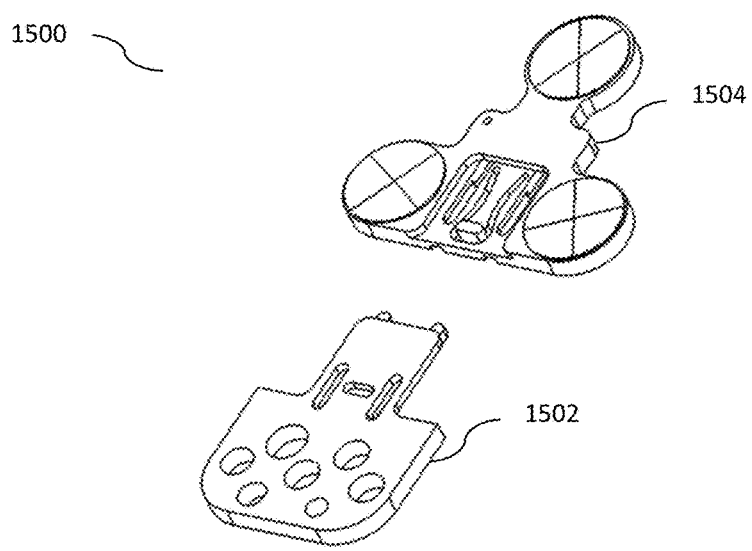
FIG. 16 shows an exploded front view of the calibration assembly shown in FIG. 15.
Figure 17:
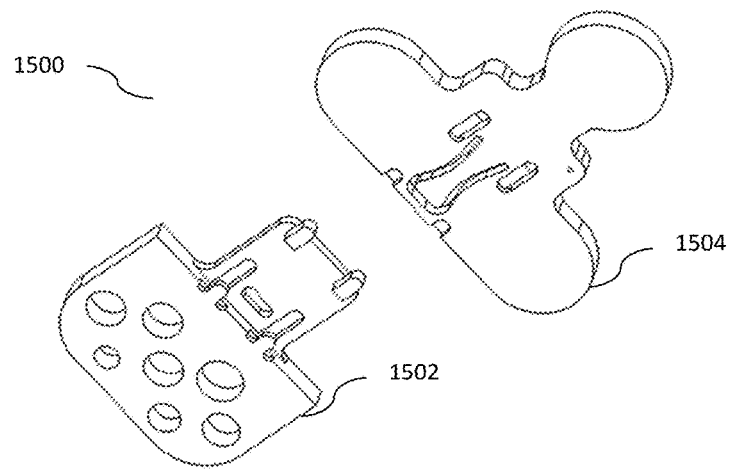
FIG. 17 shows an exploded back view of the calibration assembly shown in FIG. 16.

Referring to FIGS. 15-17, the system 10 may optionally include a calibration assembly 1500 comprising a plate 1502 and a marker 1504 with tongue and groove assembly features for coupling them (1502, 1504). The tongue and groove assembly features are especially useful for precisely assembling a metal part to a plastic part, which has a different rate of thermal expansion than the metal part. The plate 1502 has a plurality of holes 1506 having a plurality of thread types to accept various impactor types. The marker 1504 has a dimple 1508 into which the tip of a stylus may be inserted for registration. The marker 1504 has a plurality of fiducials 1510.

Figure 18:
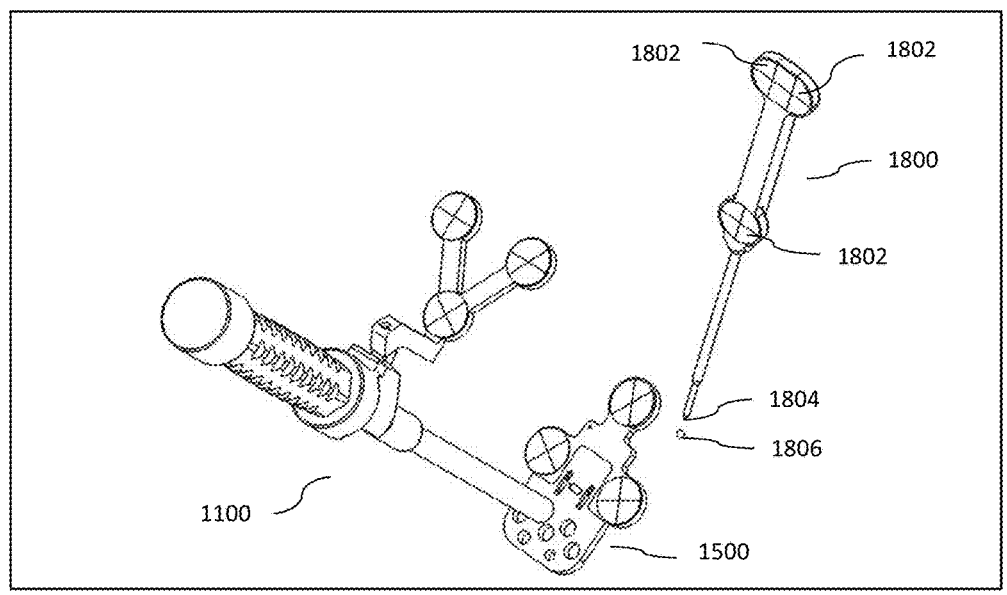
FIG. 18 shows a diagrammatic depiction of a MXUI provided by system of FIG. 1 during various calibration steps.

FIG. 18 depicts an exemplary embodiment of a MXUI shown to the user 106 via the display device 104 (e.g., the AR headset 3600) showing the calibration assembly 1500 being used for various calibration steps. First, the hip impactor assembly 1100 can be screwed into the appropriate hole of the plate 1502 so that the shoulder 1206 is seated squarely without play against the surface of the plate 1502. The cameras 3904 of the AR headset 3600 can then capture images which processed by an algorithm to determine the relationship between the shoulder of the impactor on which the acetabular shell will seat and the marker 1104 of the hip impactor assembly 1100. A stylus 1800 is shown which contains a plurality of fiducials 1802 for tracking. The tip 1804 of the stylus 1800 may be inserted into the dimple 1508 of the plate 1502 allowing the coordinate of the tip 1804 relative to the marker of the stylus 1800 to be determined. A virtual guide point 1806 is shown which is projected into the user's 106 field of view at a specific location relative to the marker 1504. The user 106 places the tip 1804 of the actual stylus 1800 where the virtual guide point 1806 is located according to the user's 106 depth perception thereby connecting his actual view with the virtual view represented by the virtual guide point. An algorithm then applies a correction factor to account for variables such as the intraocular distance of the user 106. This is beneficial if the user's depth perception will be relied on in a mixed reality state for precise location of tools or implants.

Figure 19:
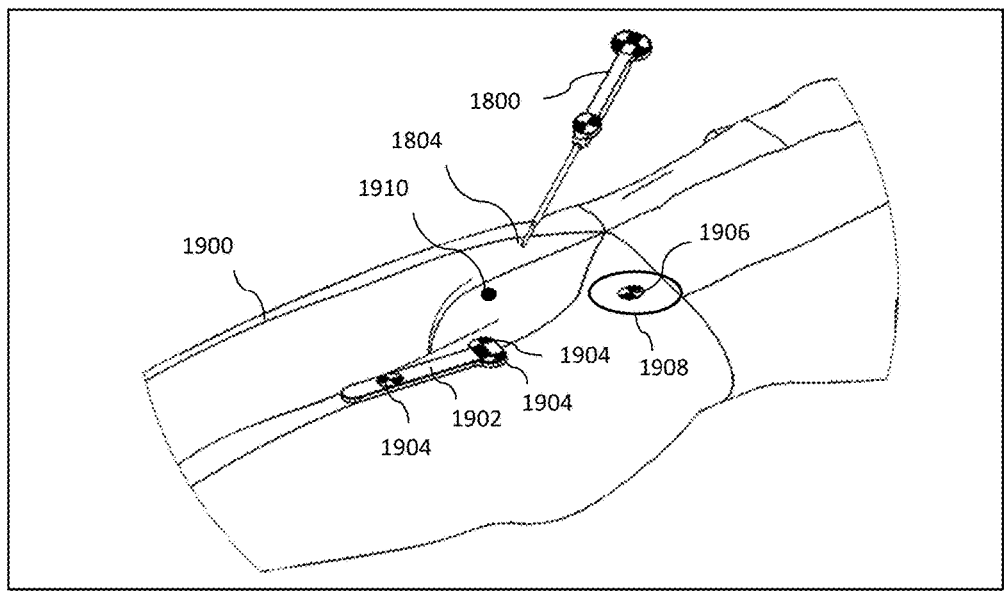
FIG. 19 is a diagrammatic depiction of a MXUI provided by system of FIG. 1 during a pelvic registration step of a hip replacement procedure.

FIG. 19 depicts an exemplary embodiment of a MXUI shown to the user 106 via the display device 104 of a patient 1900 at the beginning of a hip replacement procedure. A femur marker 1902, having a plurality of fiducials 1904 for tracking, is attached to the skin of the patient's 1900 thigh with adhesive tape such as Ioban. Alternatively, the femur marker 1902 could be fixated directly to the bone of the femur by use of pins and a clamp assembly like that depicted in FIG. 13B. The user 106 registers the anterior landmarks of the pelvis using the tip 1804 of the stylus 1800 to determine the location of the pelvis in the reference frame of the femur marker 1902 to establish a temporary pelvic reference frame. In another embodiment, this registration can be in the body reference frame defined by SLAM scanning of the visible surface of the patient. In another embodiment, the anterior landmarks of the pelvis can be registered by generating a surface map with SLAM and having the user 106 identify each point by positioning a virtual point 1910 on each landmark in turn by motion of his head. In another embodiment, a single fiducial 1906 can be placed at the location to be registered. A virtual circle 1908 can be used to define a mask whose position is controlled by the gaze of the user 106. The machine vision algorithm only looks for a single fiducial 1906 within the virtual circle 1908. Registration steps may be triggered with a voice command by the user 106 such as "register point". The user 106 may also register a point representing the distal femur such as the center of the patella or the medial and lateral epicondyles. When each point is registered, a virtual marker, such as a small sphere, may be positioned and remain at the location of the tip at the time of registration and beyond to provide the user 106 a visual confirmation to the user 106 and check on the quality of the registration.

Figure 20:
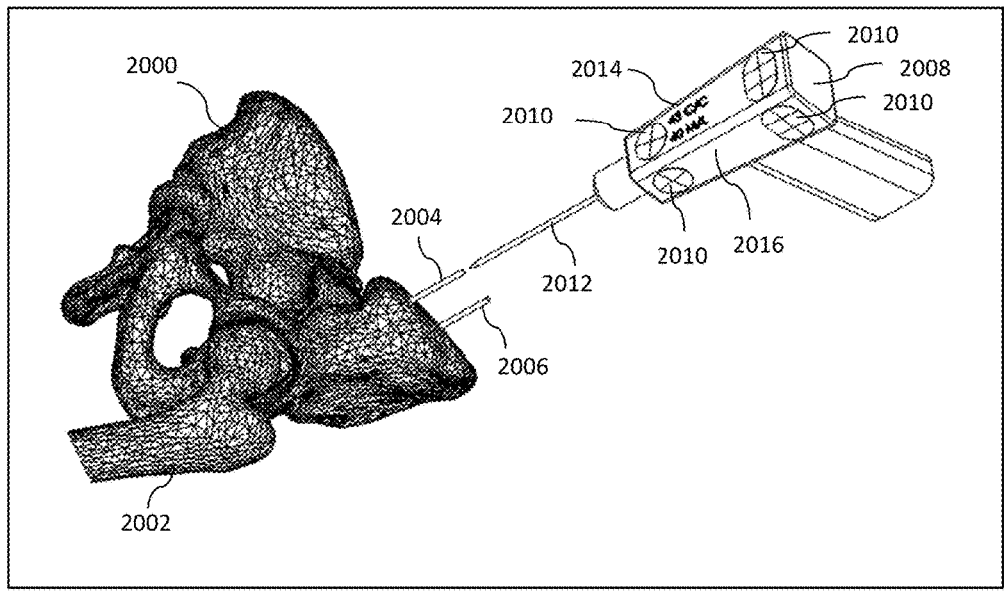
FIG. 20 is a diagrammatic depiction of a MXUI provided by system of FIG. 1 during insertion of a pin into a pelvis of a hip replacement procedure.

FIG. 20 depicts an exemplary embodiment of a MXUI shown to the user 106 via the display device 104 of a virtual pelvis 2000 and a virtual femur 2002 during a hip replacement procedure. If patient-specific models had been uploaded into the display device 104 then virtual models of these would be displayed along with any other virtual features of interest such as neurovascular structures. If not, the virtual pelvis and virtual femur could be gender-specific models, which have been scaled to best match the spacing of the registered landmarks. A first virtual trajectory 2004 and a second virtual trajectory 2006 for each of two fixation pins are displayed. In other embodiments, these may be tube-shaped or cone shaped. A drill 2008 is shown which includes a plurality of fiducials 2010 defining markers on a plurality of surfaces, which allows its pose to be tracked from various vantage points. Insertion of each pin can be guided either by lining up an actual pin 2012 with the virtual trajectory 2004 in the case where the drill is not tracked or by lining up a virtual pin (not shown) with the virtual trajectory in the case where the drill is tracked. If the drill is tracked, the angle of the drill relative to the pelvic reference frame is displayed numerically for additional augmentation. Virtual text 2014 is located on a surface 2016 of the actual drill and moves with the drill making it intuitive to the user the object to which the angles represented by the virtual text are associated.

Figure 21:
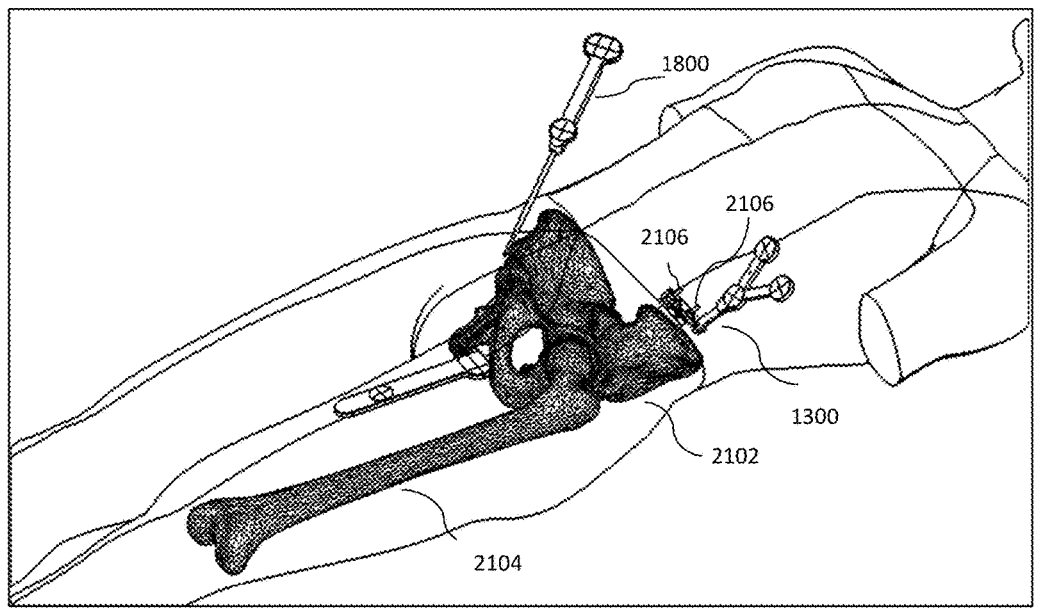
FIG. 21 is a diagrammatic depiction of a MXUI provided by system of FIG. 1 during a pelvic registration step of a hip replacement procedure.

FIG. 21 depicts an exemplary embodiment of a MXUI shown to the user 106 via the display device 104 during a hip replacement procedure with the anatomy marker 1300 attached to the patient's pelvis by way of clamping onto the pins 2106 inserted into the iliac crest. At this point, the reference frame relating to tracking the pelvis is transferred from the previous reference frame to that of the anatomy marker 1300. If desired, the pelvis may be re-registered to increase accuracy. The user 106 then makes an incision and exposes the femur using a virtual pelvis 2102, a virtual femur 2104 and virtual neurovascular structures (not shown) as a guide for the location of the incision and dissection of the muscles and joint capsule to expose the hip joint and neck of the femur. At this point, the user 106 places the leg in a reference position having approximately neutral abduction, flexion and rotation relative to the pelvis.

Figure 22:
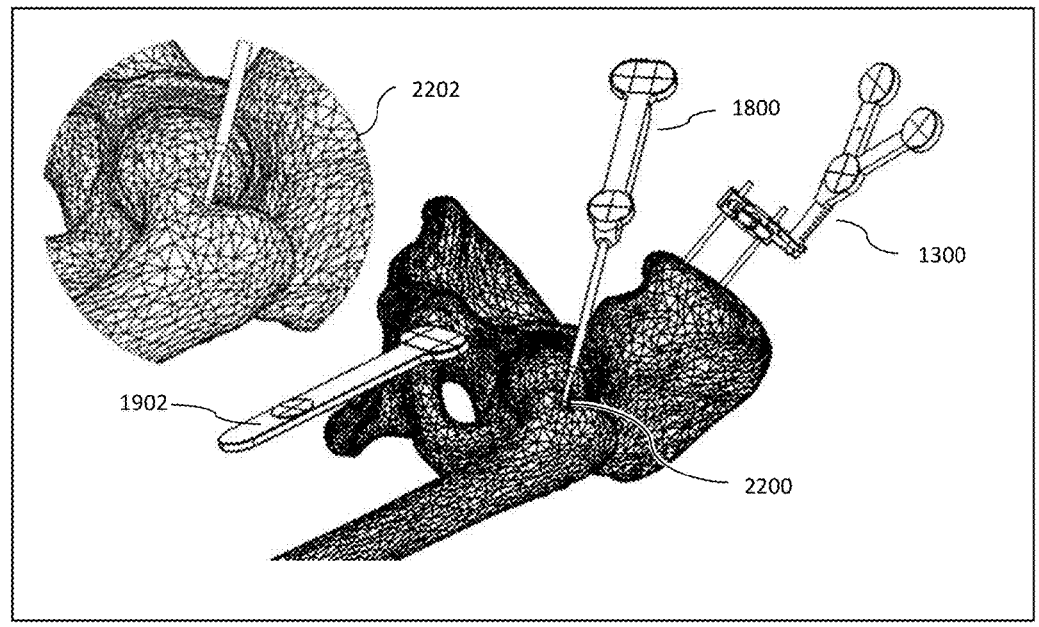
FIG. 22 is a diagrammatic depiction of a MXUI provided by system of FIG. 1 during a femoral registration step of a hip replacement procedure.

FIG. 22 depicts an exemplary embodiment of a MXUI shown to the user 106 via the display device 104 during femoral registration of a hip replacement procedure. The tip of the stylus 1800 is placed on a reference point 2200 on the proximal femur. At this time, the baseline orientation of the femur relative to the pelvis as defined by the relationship between markers 1902 and 1300 is determined and recorded. In addition, the coordinates of the reference point 2200 in the pelvic reference frame are recorded. The reference point 2200 may be enhanced by marking with a surgical pen, drilling a small hole in the bone or inserting a small tack. To improve the precision of the registration, a magnified stereoscopic image 2202 centered on the tip of the stylus is displayed as shown in FIG. 22. To aid the user 106 in finding the reference point later in the procedure, a baseline image, or images of the region around the point of the stylus may be recorded at the time of registration. These may be stereoscopic images. The user 106 then registers a point on the desired location of the femoral neck cut using the tip 1804 of the stylus 1800. This is typically the most superior/lateral point of the femoral neck. An optimum resection plane is calculated which passes through this point at the appropriate abduction and version angles.

Figure 23:
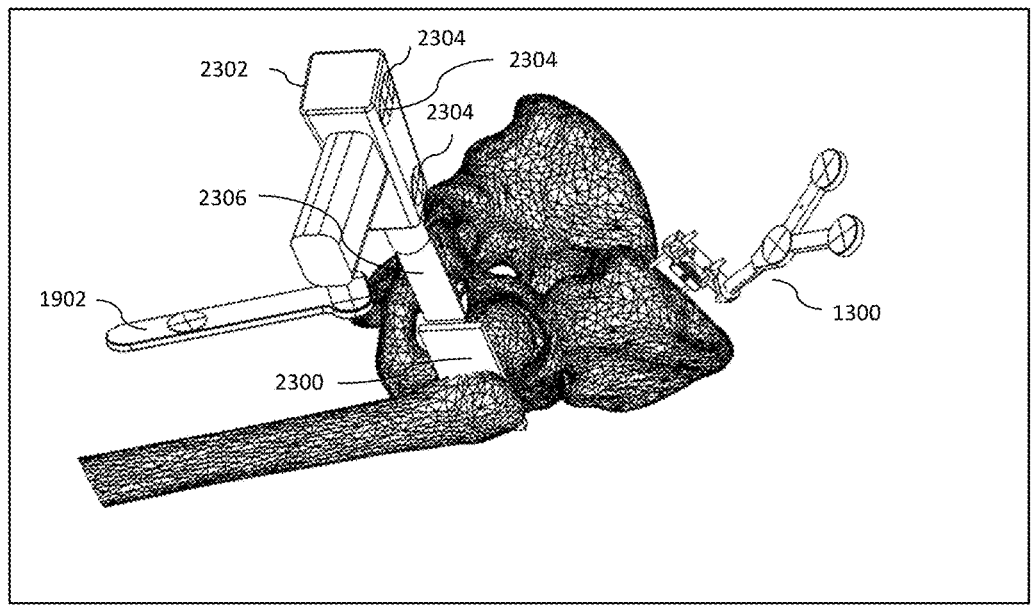
FIG. 23 is a diagrammatic depiction of a MXUI provided by system of FIG. 1 during resection of the femoral neck in a hip replacement procedure.

FIG. 23 depicts an exemplary embodiment of a MXUI shown to the user 106 via the display device 104 during resection of the femoral neck of a hip replacement procedure with a virtual resection guide 2300. A sagittal saw 2302 is shown having a plurality of fiducials 2304 defining a marker, allows the pose of the sagittal, saw 2302 to be tracked. Resection of the femoral neck can be guided either by lining up the actual saw blade 2306 with the virtual resection guide 2300 in the case where the drill is not tracked or by lining up a virtual saw blade (not shown) with the virtual resection guide 2300 in the case where the saw 2302 is tracked. As with the tracked drill shown in FIG. 20, the angles of the saw 2302 may be displayed numerically if the saw 2302 is tracked. These angles could be displayed relative to the pelvic reference frame or the femoral reference frame.

Figure 24:
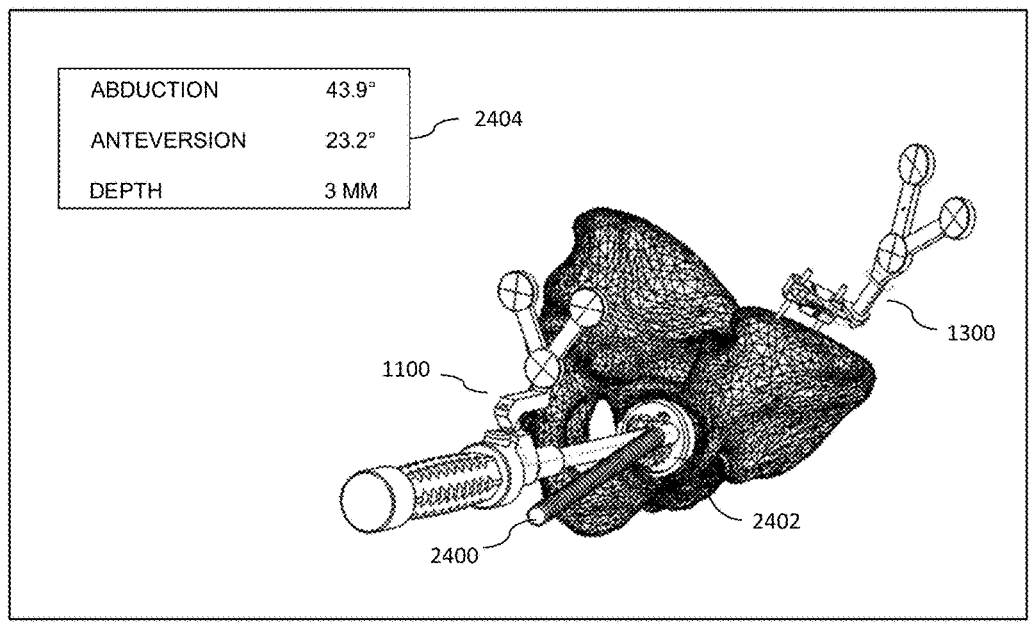
FIG. 24 is a diagrammatic depiction of a MXUI provided by system of FIG. 1 during positioning of an acetabular shell in a hip replacement procedure.

FIG. 24 depicts an exemplary embodiment of a MXUI shown to the user 106 via the display device 104 during positioning of the acetabular shell of a hip replacement procedure wherein a virtual target 2400 for the acetabular impactor assembly 1100 and a virtual shell 2402 are shown. Placement of the acetabular impactor assembly 1100 is guided by manipulating it to align with the virtual target 2400. The posterior/lateral quadrant of the shell portion of the virtual target may be displayed in a different color or otherwise visually differentiated from the rest of the shell 2402 to demarcate to the user 106 a target for safe placement of screws into the acetabulum. The numerical angle of the acetabular impactor and the depth of insertion relative to the reamed or un-reamed acetabulum are displayed numerically as virtual text 2404. A magnified stereoscopic image (not shown) similar to 2202 centered on the tip of the impactor may be displayed showing how the virtual shell interfaces with the acetabulum of the virtual pelvis 2102.

Figure 25:
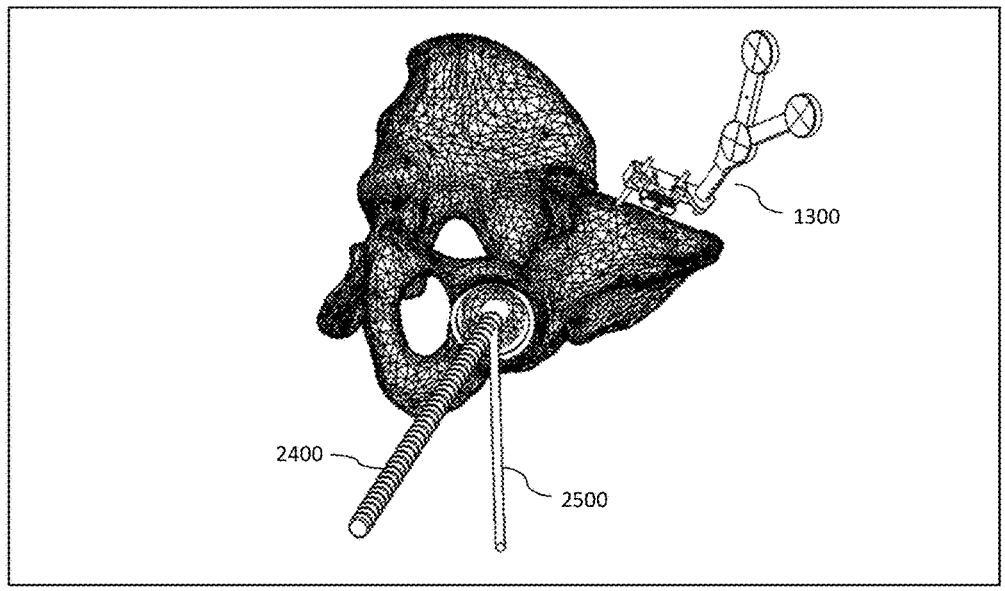
FIG. 25 is a diagrammatic depiction of a MXUI provided by system of FIG. 1 during positioning of an acetabular shell in a hip replacement procedure.

FIG. 25 depicts an exemplary embodiment of a MXUI shown to the user 106 via the display device 104 during positioning of the acetabular shell of a hip replacement procedure wherein a virtual axis 2500 of the acetabular impactor and the virtual target 2400 are shown. Placement of the acetabular impactor is guided by manipulating it to align the virtual axis 2500 with the virtual target 2400.

Figure 26:
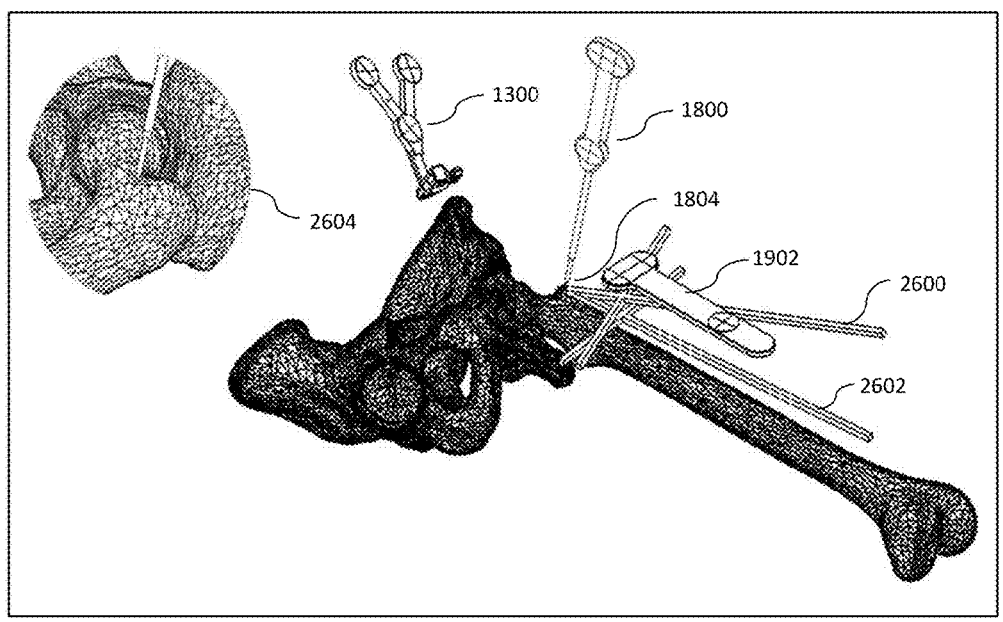
FIG. 26 is a diagrammatic depiction of a MXUI provided by system of FIG. 1 during repositioning of the femur in a hip replacement procedure.

FIG. 26 depicts an exemplary embodiment of a MXUI shown to the user 106 via the display device 104 during repositioning and registration of the femur of a hip replacement procedure. A virtual femur target 2600 is shown which represents the preoperative orientation of the femur relative to the pelvis during baseline femoral registration. The superior apex of this placed near the reference point on the proximal femur. A virtual femur frame 2602 is shown which represents the current orientation of the femur. As the femur is moved, the virtual femur frame 2602 rotates about the superior apex of the virtual femur target 2600. Re-positioning the femur to the baseline orientation is achieved by manipulating the femur to align the virtual femur frame 2602 with the virtual femur target 2600 in abduction, flexion, and rotation. With the femur re-positioned in the baseline orientation, the user then uses the tip 1804 of the stylus 1800 to re-register a reference point on the proximal femur to determine the change in leg length and lateral offset from the baseline measurement. The baseline image 2604 recorded earlier during baseline femoral registration may be displayed to assist in precisely re-registering the same reference point.

Figure 50A:
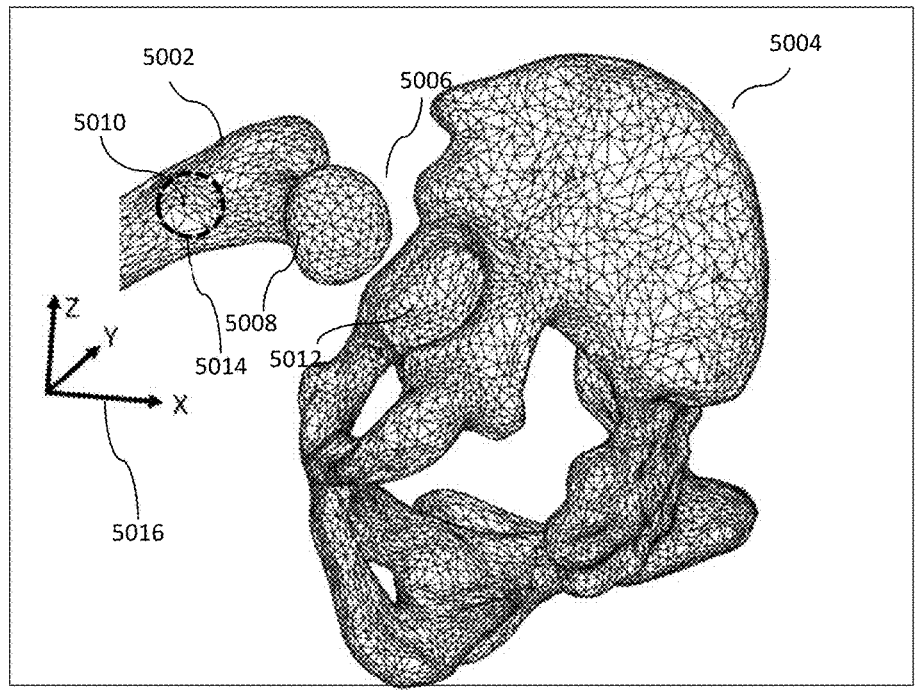
FIG. 50A is a diagrammatic depiction of exposed surfaces on the acetabulum and proximal femur in a reference position.
Figure 50B:
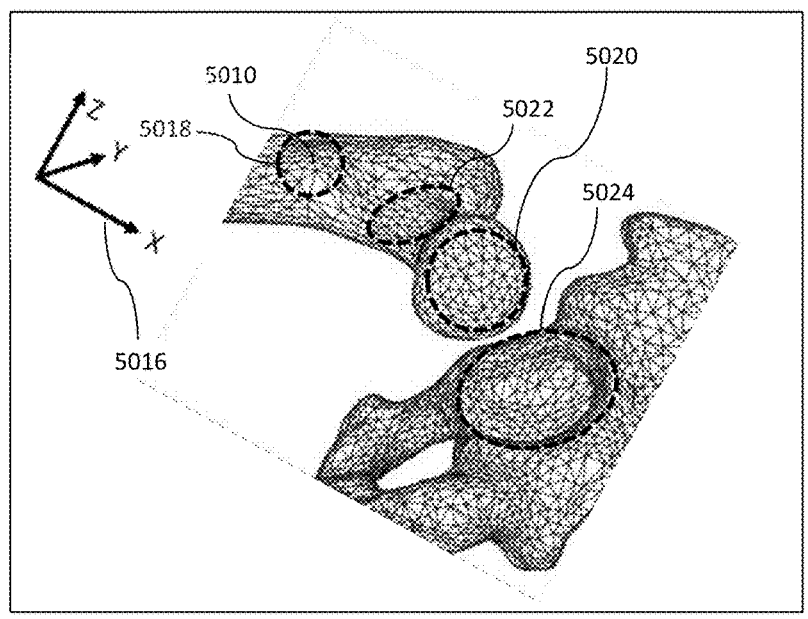
FIG. 50B is a diagrammatic depiction of exposed surfaces on the acetabulum and proximal femur in a displaced position.
Figure 51:
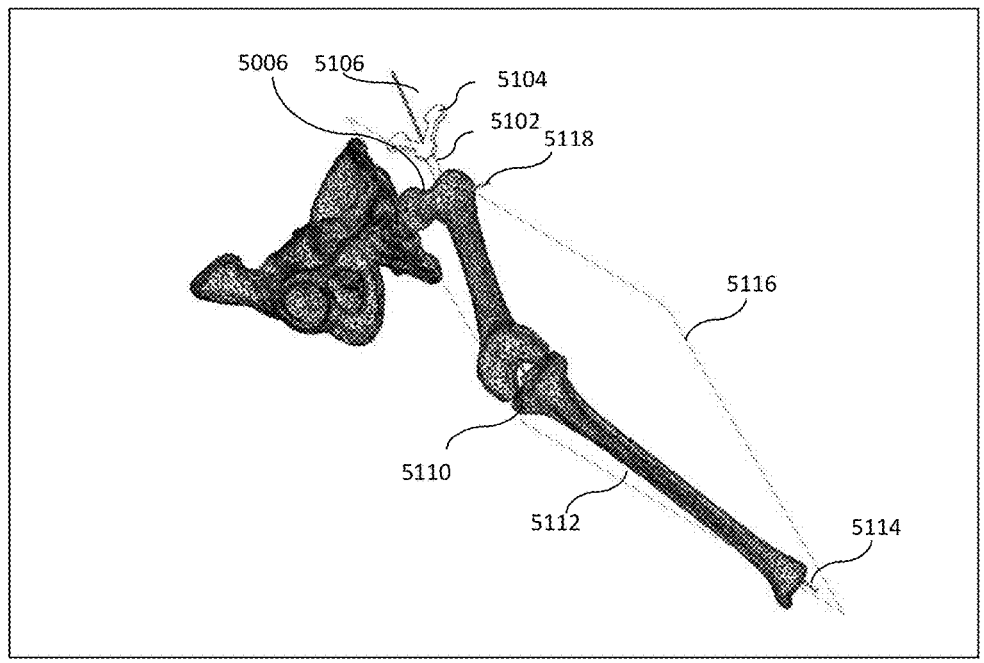
FIG. 51 is a diagrammatic depiction of a hip and leg, showing reference axes and planes for calculating femoral version.
Figure 52:
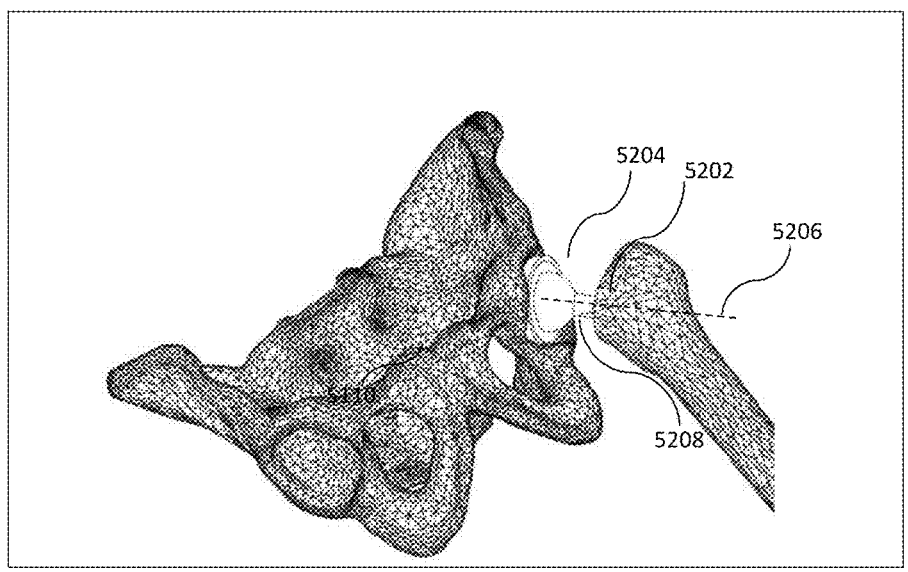
FIG. 52 is a diagrammatic depiction of a hip with implanted components.

Referring to FIGS. 50-52, the system 10 may optionally include a means for tracking anatomic structures without external fiducials fixed to the anatomy. FIGS. 50A-B depict an exemplary embodiment, in which the femur 5002 is dislocated, allowing the system 10, using sensor suite 210, to create a reference 3-dimensional surface map 5014 of the exposed surface of the lesser trochanter 5010. The surface of the lesser trochanter remains unchanged throughout the procedure and may be used by the system 10 to track the femur without additional fiducials. The boundary of the reference 3-dimensional surface map 5014 may optionally be indicated by the user by tracing a curve using a cursor or pointing device, which may operate by tracking the user's gaze. The system 10 may store the reference 3-dimensional map 5014 as a point cloud, as mathematical surfaces, or by other means. The system 10 may create a reference frame 5016 relative to the sensor suite 210 and record the initial pose of the surface map 5014 in reference frame 5016. The user 106 may register additional reference points or structures on the same bone or rigid body, such as the femoral head 5006, femoral neck 5008, and acetabulum 5012. The system may create additional 3-dimensional surface maps 5020, 5022, 5024 for the femoral head, femoral neck, and acetabulum, respectively, whose pose the system 10 records relative to the reference frame 5016. The system 10, using sensor suite 210, continuously re-scans the lesser trochanter 5010 and generates a displaced 3-dimensional surface map 5018 of the anatomy. Then comparing the displaced 3-dimensional surface map 5018 to the reference 3-dimensional surface map 5014 created for the same surface, the system 10 determines the geometric rotation and translation required to align the displaced surface map 5018 and reference surface map 5014 for best fit. The system 10 then applies the same rotation and translation to all stored reference points and structures on the rigid body of the femur 5002, calculating the current pose of all such points and structures relative to the reference frame of sensor suite 210. The system 10 may calculate diameter of the femoral head 5006 or acetabulum 5012 and display it to the user 106 as a guide for selecting an acetabular reamer size. The system 10 may calculate the center of the femoral head 5006 relative to the reference surface map 5014. The system 10 may also calculate the position of the center of the acetabulum 5012 relative to the pelvis 5004. The user 106 then inserts a broach or reamer 5102 with attached fiducial 5104 into canal of the femur, identifying a femoral axis 5106. The system 10 calculates a femoral neck axis 5118 between the femoral head 5006 and femoral axis 5106. With the knee 5110 flexed to approximately 90°, the cameras 206 scan the lower leg 5112, identifying its approximate central axis 5114, which is used with the femoral axis 5106 to define a reference plane 5116 from which the version angle of the native femoral neck axis 5118 is calculated. In the course of the procedure, the native femoral head 5006 and acetabulum 5012 are replaced with a femoral implant 5202 and acetabular implant 5204, respectively. The system 10 may detect the centers of the implanted acetabular shell 5204 and femoral head 5208, allowing the system 10 to calculate and display the change in distance from the femoral axis 5106 to the femoral head 5208 (femoral offset), or the change of position of the center of the acetabulum 5208, between the respective native and implanted conditions of each structure. Following replacement of the femoral head 5006, but prior to replacement of the acetabulum 5012, the system 10 may calculate and display the femoral version based on a new calculation of the femoral neck axis 5206 using the replaced femoral head 5208. The system 10 may calculate and display the additional anteversion required in the acetabular implant 5204 to achieve a target for combined anteversion of the femoral implant 5202 and acetabular implant 5204. The system 10 may calculate and display a change in distance between the femur 5002 and pelvis 5004 arising as a result of the procedure.

Figure 53:
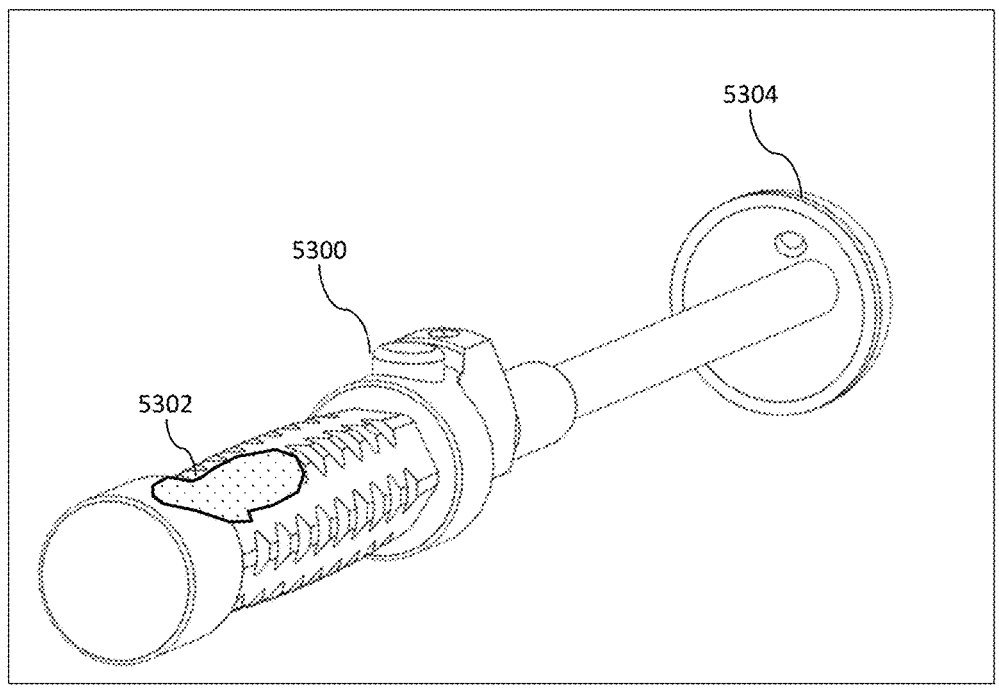
FIG. 53 is a diagrammatic depiction of a hip impactor and shell showing surfaces mapped on the impactor.

FIG. 53 depicts an exemplary embodiment of a hip impactor 5300 tracked via a 3-dimensional map of a portion of its exposed surface 5302, rather than by means of a supplementary fiducial. The system 10 may register an acetabular shell 5304 to this surface by simultaneously scanning the shell 5304 and impactor surfaces using the cameras 206.

Figure 59:
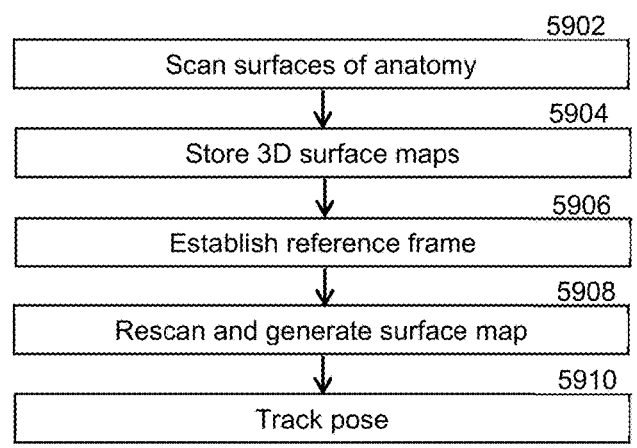
FIG. 59 is a flowchart showing an exemplary method of navigating a hip replacement procedure.

FIG. 59 depicts a flowchart showing how the system 10 and its sensor suite 210 can be used for navigation in a hip arthroplasty procedure. The sensor suite 210 can scan the lesser trochanter 5010 (5902). From this scan, reference 3-dimensional surface map 5014 can be stored (5904). The system 10 can then establish a reference frame 5016 for the femur 5002 relative to the sensor suite 210 (5906). Then, repeatedly scanning the exposed lesser trochanter 5010, the system 10 generates a displaced 3-dimensional surface map 5018 for each scan (5908). With each successive scan, the system can compare the displaced surface map 5018 to the reference surface map 5014 for the same region on the lesser trochanter 5010. Based on this comparison, the system 10 can track the pose of the femur 5002 relative to sensor suite 210 by determining the translation and rotation required to best fit the displaced surface map 5018 with the reference surface map 5014 (5910).

Figure 54:
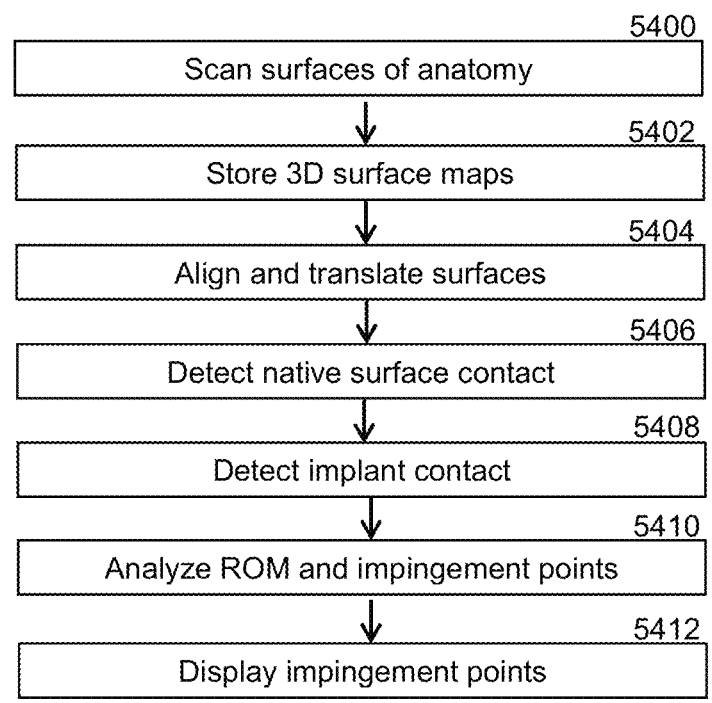
FIG. 54 is a flowchart showing how the system of FIG. 1 can be used to analyze hip kinematics in accordance with the principles of the present invention.

FIG. 54 depicts a flowchart showing how the system 10 and its sensor suite 210 can be used to analyze hip kinematics. The sensor suite 210 can scan exposed surfaces of the patient's anatomy, including the native femoral head 5006 and acetabulum 5012 (5400). From these surfaces, 3-dimensional maps 5020,5024 of each structure can be stored (5402). The system 10 can then rotate the surfaces into the orientations expected in a standing patient and translate them together in the direction of body weight (5404). The system 10 can then calculate the contact point or patch between the two surfaces, which may be a more appropriate center of rotation than the centers of the approximately spherical surfaces (5406). Following replacement of the native anatomy with femoral implant 5202 and acetabular implant 5204, the system 10 can similarly identify the contact points for the implants (5408). Using the implant geometry, the system 10 can perturb the hip angle to calculate the angular range of motion allowed in each direction prior to impingement between implants, or between implants and bone (5410). The location of first impingement, which limits range of motion, can be highlighted in the display device 104 (5412). For example, the femoral neck 5008 may impinge on the exposed rim of the acetabulum 5012, or on the acetabular implant 5204. If at least one of the impinging surfaces is on native bone, the user 106 may elect to trim the bone to increase the range of motion. If at least one of the impinging surfaces is on an implant, the user 106 may elect to adjust the position or angle of the implant.

IV. Use of System in Conjunction with a C-Arm System

Figure 27:
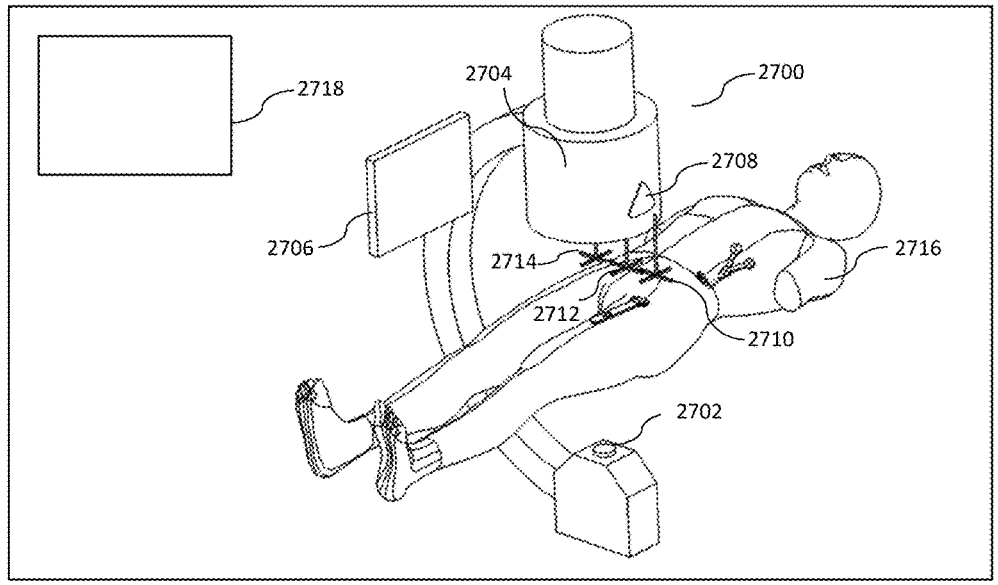
FIG. 27 is a diagrammatic depiction of a MXUI provided by system of FIG. 1 using a C-arm during a hip replacement procedure.

FIG. 27 depicts an exemplary embodiment of a MXUI shown to the user 106 via the display device 104 during imaging of a patient with a C-arm. A C-arm imaging system 2700 is shown having an X-ray source 2702, an imaging unit 2704 and a display unit 2706. A trackable label 2708 has been attached to the C-arm 2700. A virtual hip alignment guide 2710 and a virtual pelvis alignment guide 2712 are shown. These are perpendicular to the anterior pelvic plane and centered over the hip joint and pubic symphysis respectively. Placement of the C-arm 2700 is guided by adjusting the surface of the imaging unit 2704 to be aligned with the appropriate virtual alignment guide. If the C-arm 2700 is trackable, then a virtual C-arm alignment guide 2714 may be displayed. In this case, placement of the C-arm 2700 is guided by adjusting the virtual C-arm alignment guide 2714 to be aligned with the appropriate virtual alignment guides 2710 or 2712. The positional and angular misalignment relative to the target can also be displayed numerically as virtual text 2718.

Figure 28:
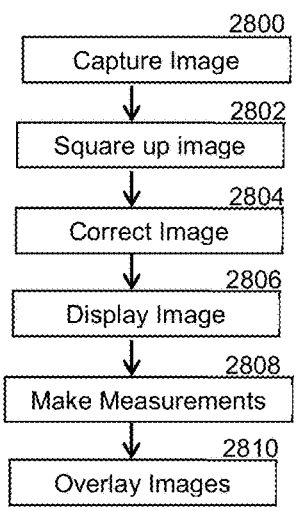
FIG. 28 is a flowchart showing how the system of FIG. 1 can be used in conjunction with a C-arm in a surgical procedure in accordance to the principles of the present invention.

FIG. 28 depicts a flowchart showing how the system 10 and its display device 104 (e.g., the AR headset 3600) can be used in conjunction with the C-arm 2700 in a surgical procedure. The camera 3904 (e.g., a high definition camera or the like) incorporated in the AR headset 3600 can be used to capture the image displayed on the C-arm monitor (2800). The image can be adjusted to "square it up" so that it matches what would be seen if the camera 3904 had been perfectly centered on and normal to the image on the monitor (2802). The knowledge of the position of the imager and source relative to the anatomy being imaged can be used to correct images for magnification and parallax distortion due to divergence of the X-ray beam from the source (2804). The corrected image can then be displayed in the AR headset 3600 (2806). This can then be used to allow the user 106 to make measurements relevant to the procedure such as acetabular cup placement or leg length (2808). Other images can be simultaneously displayed, overlaid, mirrored, or otherwise manipulated to allow the user 106 to make comparisons (2810).

In another embodiment, image capture can also be achieved by wireless communication between the C-arm 2700 and the AR headset 3600 for example by transfer of file in DICOM format. Alternatively, algorithms incorporating machine vision could be employed to automatically make measurements such as the inclination and version of an acetabular shell. Edge detection can be used to trace the outline of the shell. The parameters of an ellipse, which optimally matches the outline, can be determined and used to calculate the anteversion of the shell from the ratio of the length of the minor and major axes of the optimum ellipse. The inclination can be calculated for example by placing a line tangential to the most inferior aspects of the pubic rami and calculating the angle between the major axis of the shell ellipse and this line. Similarly, the comparative leg length and lateral offset of the femur can be determined and could be corrected for changes or differences in abduction of the femur by recognizing the center of rotation from the head of the femur or the center of the spherical section of the shell and performing a virtual rotation about this point to match the abduction angles. This type of calculation could be performed almost instantaneously and save time or the need to take additional radiographic images. Furthermore, and in another embodiment, an algorithm could correct for the effect of mispositioning of the pelvis on the apparent inclination and anteversion of the shell by performing a virtual rotation to match the widths and aspect ratios of the radiolucent regions representing the obturator foramens.

In yet another embodiment, C-arm imaging can be used to register the position of anatomy, such as the pelvis. For this, the anatomy marker 1300 would incorporate radio-opaque features of known geometry in a known pattern. The C-arm image is captured and scaled based on known marker features and displayed in the AR headset 3600. A virtual model of the anatomy generated from a prior CT scan is displayed to the user 106. The user 106 can manipulate the virtual model to position it in a way that its outline matches the C-arm image. This manipulation is preferably performed by tracking position and motion of the user's 106 hand using SLAM. Alternatively, the user 106 can manipulate a physical object, which incorporates a marker with the virtual model moving with the physical object. When the virtual model is correctly aligned with the C-arm image, the relationship between the patient's anatomy and the anatomy marker 1300 can be calculated. These steps and manipulations could also be performed computationally by the software by using edge detection and matching that to a projection of the profile of the model generated from the CT.

V. Spinal Procedures

Figure 31:
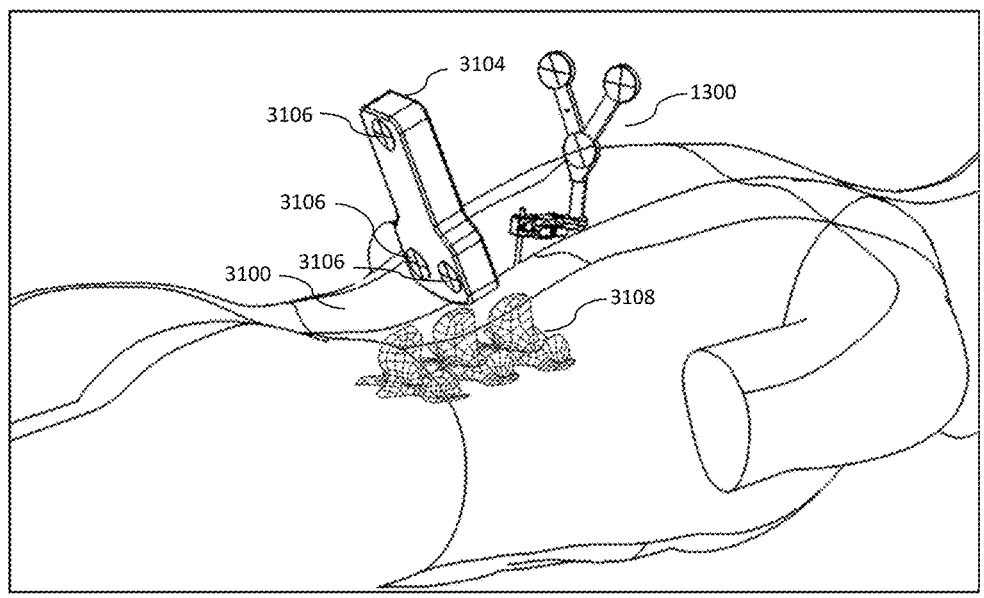
FIG. 31 is a diagrammatic depiction of a MXUI provided by system of FIG. 1 during registration of a spine with an ultrasound probe in a spinal fusion procedure.

FIG. 31 depicts an exemplary embodiment of a MXUI shown to the user 106 via the display device 104 during registration of a spine with ultrasound. An anatomy marker 1300 is fixated to a vertebra adjacent to the operative site. An ultrasound probe 3104 which includes a plurality of fiducials 3106 defining a marker is provided. In one embodiment, the ultrasound probe 3104 is battery operated, cordless, and can communicate with the AR headset 3600 via radio. The software has geometric and other information necessary to be able to position and scale the 2D ultrasound image relative to the marker's 1300 position. The ultrasound probe 3104 is moved over the surface of the patient 3100 to scan the region of interest. The software combines the 2D image data with the six degree of freedom pose information of the ultrasound probe 3104 relative to the anatomy marker 1300 to generate a virtual model 3108 representing the surface of the vertebrae of interest. The ultrasound probe 3104 may be rotated relative to anatomy of interest to get a more complete 3D image. The posterior contour of the spinous process and the left and right mammillary processes can be matched to the same features of a CT generated 3D model of the vertebra to register and subsequently position the virtual model of the vertebra in a mixed reality view. Alternatively, any appropriate features which are visible on an ultrasound scan can be utilized or the position of the virtual model can be relative to the surface of the patient as determined by SLAM. The latter is appropriate for procedures in which the patient anatomy of interest is stationary for the duration of the procedure and attachment of a marker would be unnecessarily invasive or burdensome. Ultrasound can similarly be used in this way to generate models of anatomy of interest such as, but not limited to, bony structures, nerves and blood vessels. Registration of any anatomy can be achieved. For example, a pelvic reference frame can be established using ultrasound to locate the proximal apex of the left and right ASIS and the pubis. The same method can be used to track the position of tools or implants percutaneously.

Figure 32:
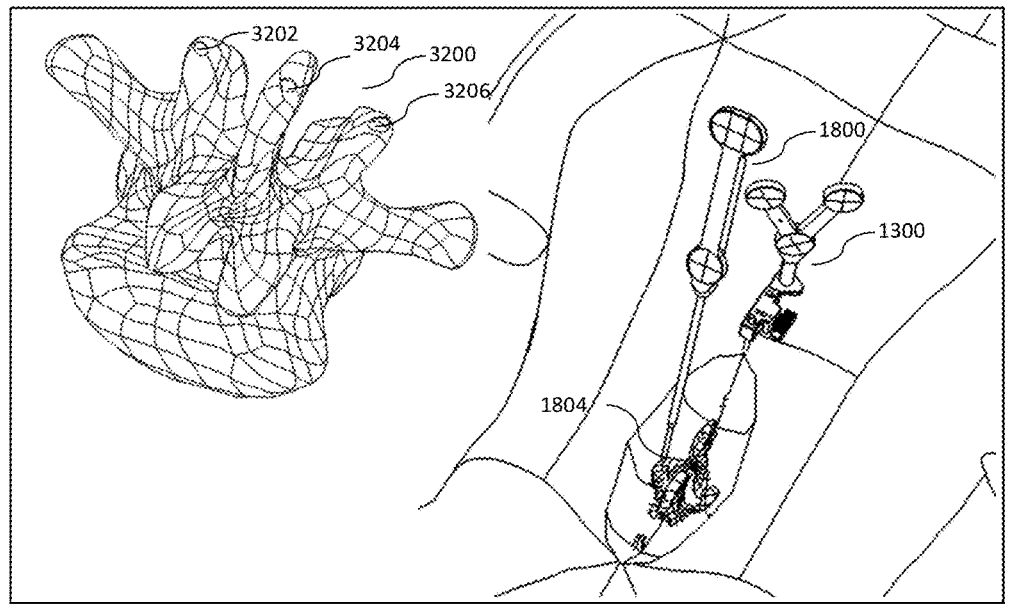
FIG. 32 is a diagrammatic depiction of a MXUI provided by system of FIG. 1 during registration of a spine with a stylus in an open spinal fusion procedure.
Figure 33:
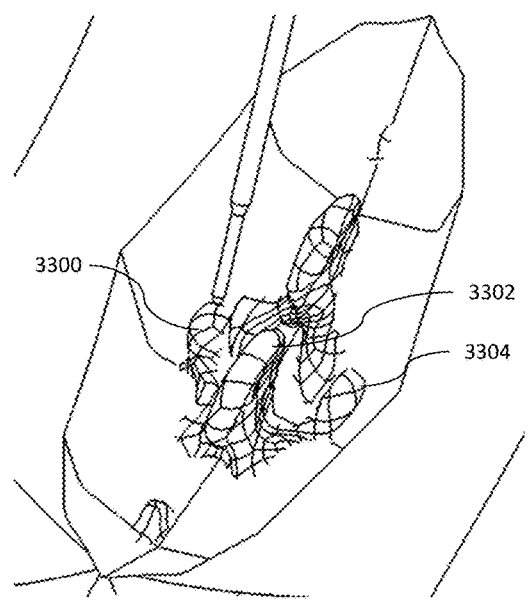
FIG. 33 is a close-up front view of the surgical exposure portion of FIG. 32.

FIG. 32 depicts an exemplary embodiment of a MXUI shown to the user 106 via the display device 104 during registration of a spine with a stylus 1800. The anatomy marker 1300 is fixated to a vertebra adjacent to the operative site. A virtual model 3200 of the patient's vertebra generated from pre-operative imaging is displayed. This virtual model includes a first landmark 3202, a second landmark 3204 and a third landmark 3206. FIG. 33 depicts a close up view of the exposed anatomy shown in FIG. 32. The soft tissues of the patient have been dissected sufficiently to expose a first bony process 3300, a second bony process 3302 and a third bony process 3304 which contain the three landmarks. The user 106 registers the three landmarks by placing the stylus tip 1804 at the points on the actual vertebra that best match the location of the landmarks shown on the virtual model. The software then re-positions the virtual model 3200 in the user's view to best align these points. The user 106 visually verifies the quality of the registration by comparison of the virtual model to the actual exposed regions of the vertebra. If necessary, the user 106 may make adjustments by using the tip 1804 of the stylus 1800 to reposition the virtual model. In an alternative embodiment, the landmarks are arcs traced over the most posterior aspect of each process. In another embodiment, the contours of the exposed processes are established with SLAM and the software performs a best fit on the position of the virtual model to match these contours.

Figure 34:
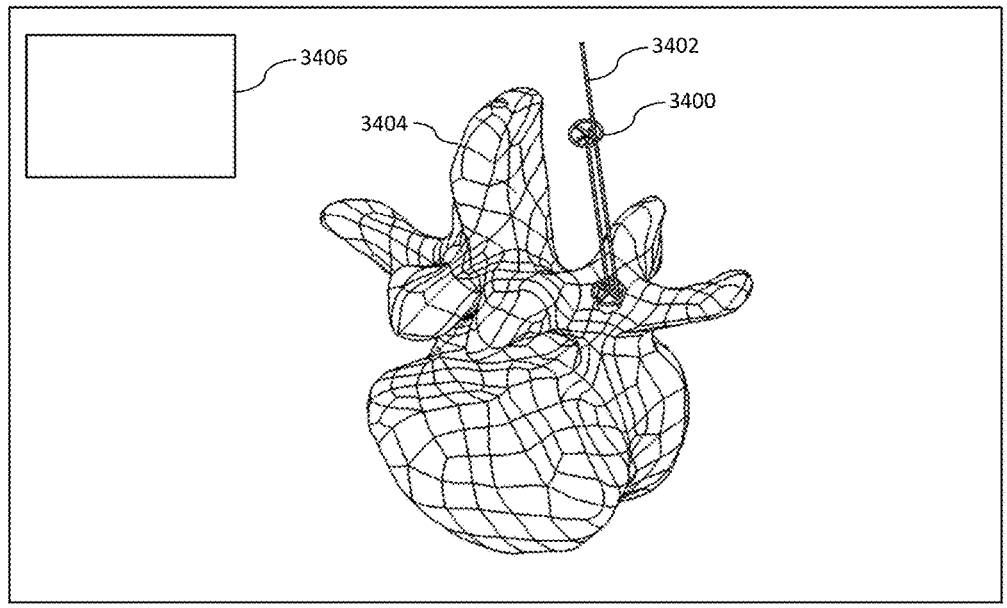
FIG. 34 is a diagrammatic depiction of a MXUI provided by system of FIG. 1 during drilling of a pedicle in a spinal fusion procedure.
Figure 35:
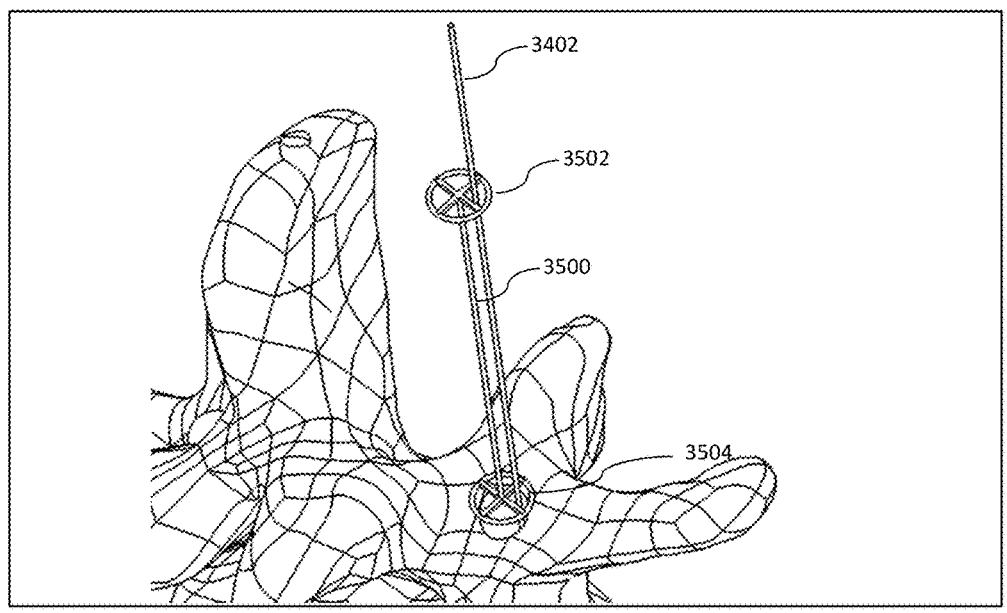
FIG. 35 is a close-up view of the virtual drill and target portion of FIG. 34.
Figures 36A, 36B:
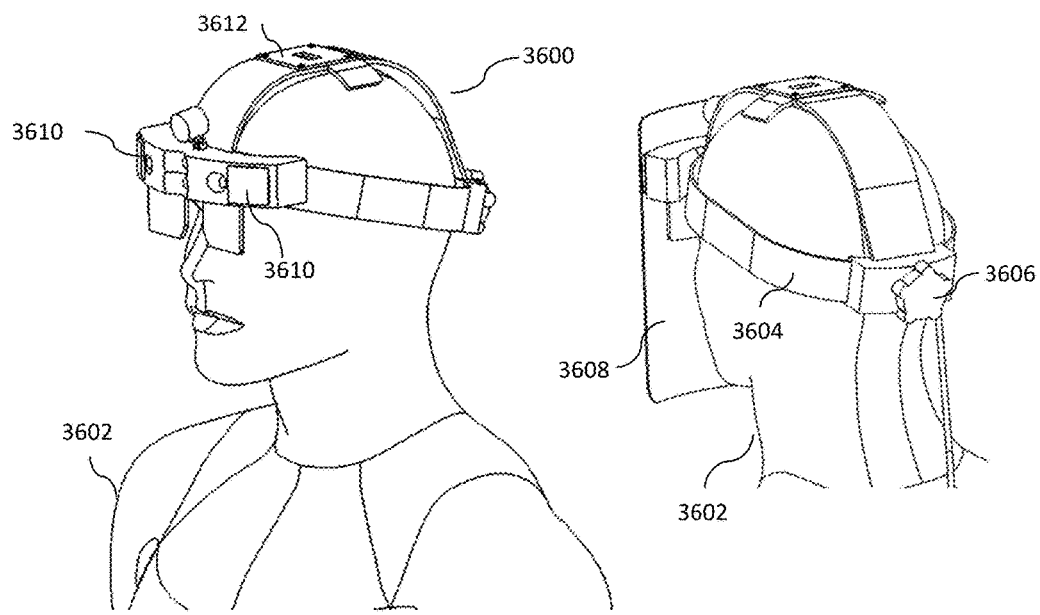
FIG. 36A shows a perspective front view of a diagrammatic depiction of a user wearing an AR headset of the system of FIG. 1.
FIG. 36B shows a perspective back view of a diagrammatic depiction of a user wearing an AR headset of the system of FIG. 1 having a protective face shield.
Figures 37A, 37B:
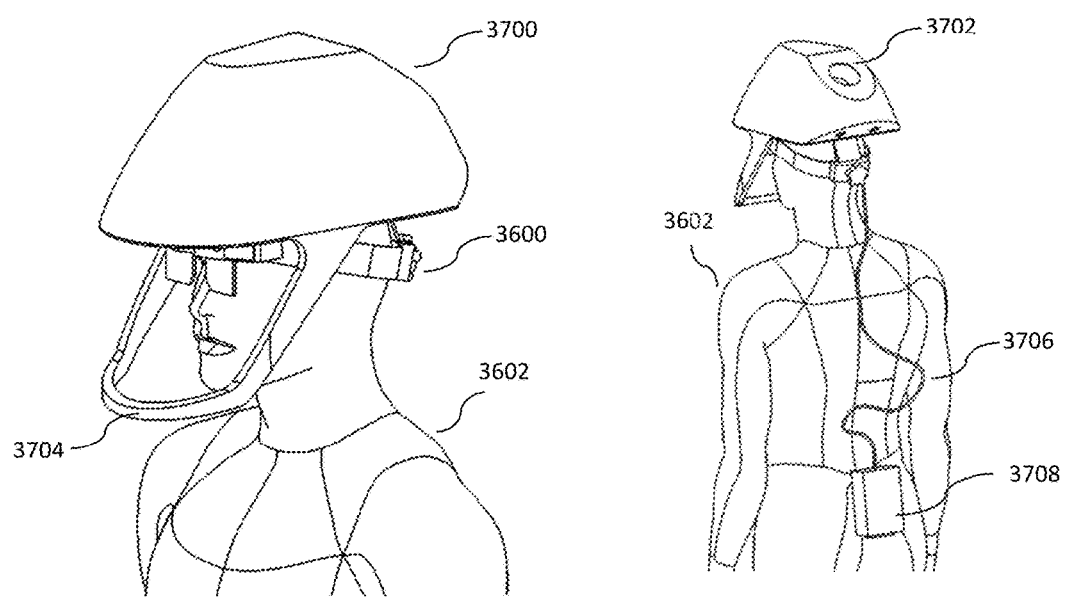
FIG. 37A is a perspective front view of diagrammatic depiction of a user wearing an AR headset of the system of FIG. 1 having a surgical helmet.
FIG. 37B is a perspective back view of the items shown in FIG. 37A.
Figures 38A, 38B:
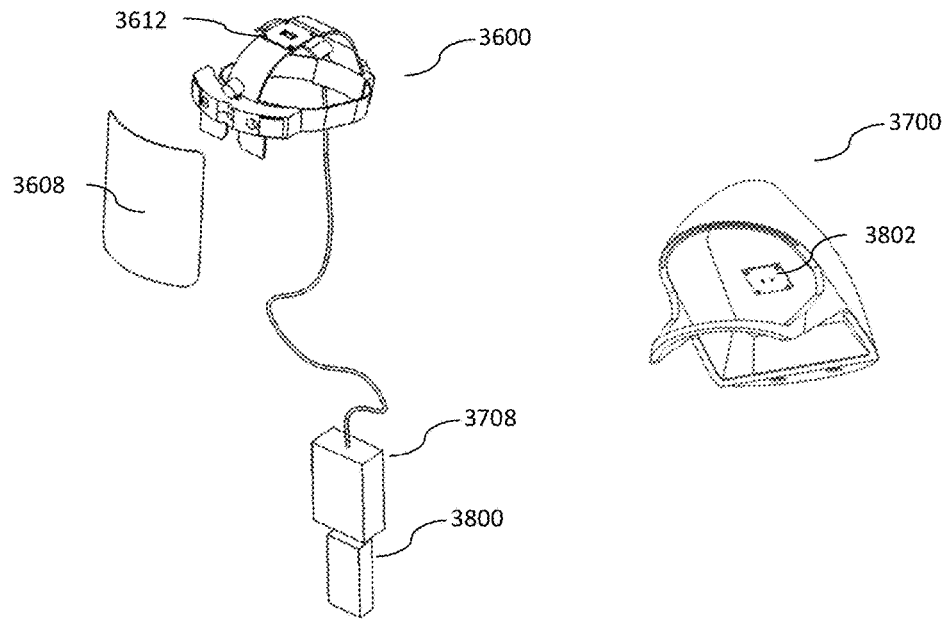
FIG. 38A is a perspective front view of diagrammatic depiction of various components of the system of FIG. 1.
FIG. 38B is a perspective back view of the surgical helmet shown in FIG. 37A.

FIG. 34 depicts an exemplary embodiment of a MXUI shown to the user 106 via the display device 104 during a spinal fusion procedure. A virtual target 3400 for the drill bit and a virtual drill bit 3402 are shown. A virtual vertebra 3404, rendered to be transparent relative to the virtual target 3400 and virtual drill bit 3402 are shown. The numerical angle of the drill bit and the depth of penetration or distance from the tip of the drill bit to the maximum safe depth of insertion are displayed numerically as virtual text 3406. FIG. 35 depicts a close up view of the virtual target 3400 and virtual drill bit 3402 shown in FIG. 34. The virtual target 3400 is shown in the form of a rod 3500 which has a proximal cross-hair 3502 and a distal cross-hair 3504. To maintain the actual drill bit in a safe target trajectory the user must maintain a position in which the virtual drill bit 3402 passes through the rings of both cross-hairs of the virtual target 3400. The ideal trajectory is achieved when the virtual drill bit 3402 passes through the center of both cross hairs. If the actual drill bit moves outside a safe target trajectory the color of the virtual target 3400 changes to alert the user and an audible warning is emitted. The distal cross-hair 3504 is positioned at the planned starting point on the surface of the bony. The axial length of the virtual target 3400 and the virtual drill bit 3402 are scaled so that their proximal ends are coincident when the drill reaches its maximum planned depth. The scaling for motions of displacement of the virtual drill bit 3402 is 1:1 when it is far from the virtual target 3400 but expands to a higher magnification for greater precision when closer allowing greater precision.

Although this is described in the context of drilling with a drill bit, this mixed reality view can be used for multiple steps including tapping of a pedicle or driving in a pedicle screw or use of a trackable awl to find the canal of the pedicle screw. As a quick means to re-calibrate the axial location of the tip of the drill, tap or screw as they are swapped out, the user places the tip into a dimple of a marker. Implants can be introduced less invasively by AR guidance for example an interbody cage can be positioned during a PLIF, XLIF or TLIF procedure.

In another embodiment, a surgical drill could be equipped to communicate wirelessly with the headset to provide two-way communication. This could facilitate various safety and usability enhancing features including the following. Automatically stopping the drill or preventing operation if the drill is not within the safe target trajectory or reaches the maximum safe depth. Providing a convenient user interface to specify appropriate torque setting parameters for a torque limiting application. For example, a maximum insertion torque for a pedicle screw of a given size or a seating torque for the set screw of a pedicle screw. Actual values used could be recorded with the patient record for documentation or research purposes for example, the torque curve during drilling, the final seating torque of a pedicle screw or set screw, the implanted position of a pedicle screw or the specific implants used.

In another embodiment, the AR headset 3600 could be connected wirelessly to a neuromonitoring/nerve localization system, to provide the user 106 (e.g., spine surgeon) real-time warnings and measurements within his field of view, particularly during minimally invasive procedures such as XLIF. Further, when used in conjunction with pre-operative imaging in which the patient's actual nerves have been imaged and reconstructed into 3D models, if the system detects that a particular nerve has been stimulated or is being approached by the stimulating probe, the hologram representing that nerve structure can be highlighted to the user 106 to make it easier to avoid contact with or injury to the nerve structure.

VI. Knee Replacement Procedures

Figure 42:
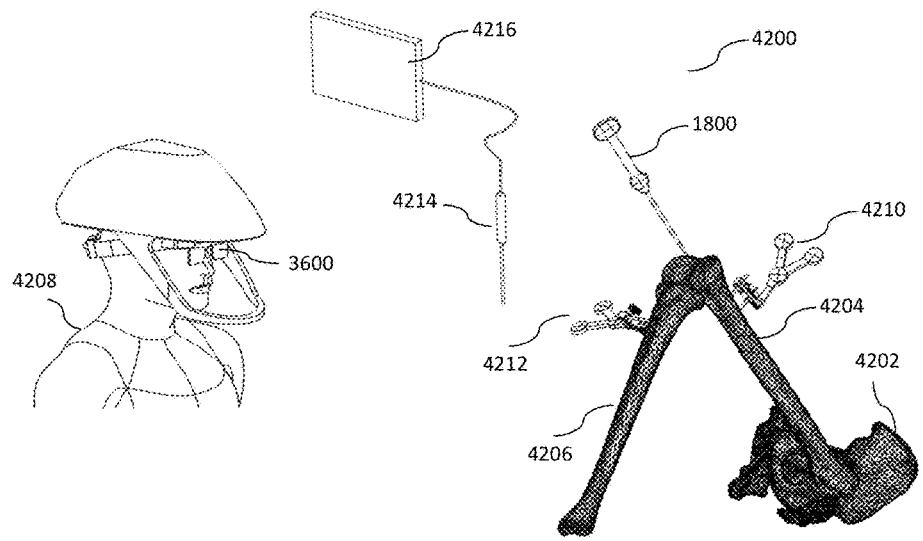
FIG. 42 is a perspective front view of components of the system shown in 37A used in a knee replacement procedure.

In another exemplary embodiment of the present invention and referring to FIG. 42, the system 10 is used for knee replacement surgery. A pelvis 4202, femur 4204 and tibia 4206 of a knee replacement patient are shown in FIG. 42, the surgeon 4208 (i.e., the user 106) is shown wearing the AR headset 3600. A femur marker 4210 and tibia marker 4212 are fixated to the femur and tibia respectively with pins. The femur is moved through a range of motion to determine the center of rotation as a proxy for the center of the hip in the reference frame of the femur marker 4210. The knee is then flexed through a range of motion to determine the baseline, pre-operative flexion axis of the knee. The surgeon 4208 then makes an incision to expose the knee joint. A stylus 1800 is used for registration of the center of the distal femur, based on a landmark such as the most distal point of the sulcus of the trochlea. The proximal center of the tibia is defined by registration of the footprint of the ACL with the tip of the stylus. For certain minimally-invasive procedures, bony landmarks may be registered arthroscopically by insertion of the stylus through one port into the joint capsule and visualizing it with an arthroscope 4214 inserted through a second port. Further, the arthroscopic image 4216 from the arthroscope may be communicated wirelessly to the AR headset 3600 and displayed as part of a MRUI. In an alternative embodiment, a stylus tip could be incorporated in a trackable arthroscope allowing landmark registrations to be performed through a single port. The stylus 1800 may then be used to register the medial and lateral malleoli and determine the center of the ankle in the reference frame of the tibia marker 4212 by interpolation of these points. At this point a femoral reference frame is established with its origin at the center of the distal femur, with a first axis extending toward the center of the hip, a second axis defined by the flexion axis of the knee and a third axis defined as the normal to the first and second axes. A tibial reference frame is defined with its origin at the center of the proximal tibia, with a first axis extending toward the center of the ankle, a second axis defined by the flexion axis of the knee and a third axis defined as the normal to the first and second axes. These reference frames may be presented as virtual images in a MRUI.

Figure 43:
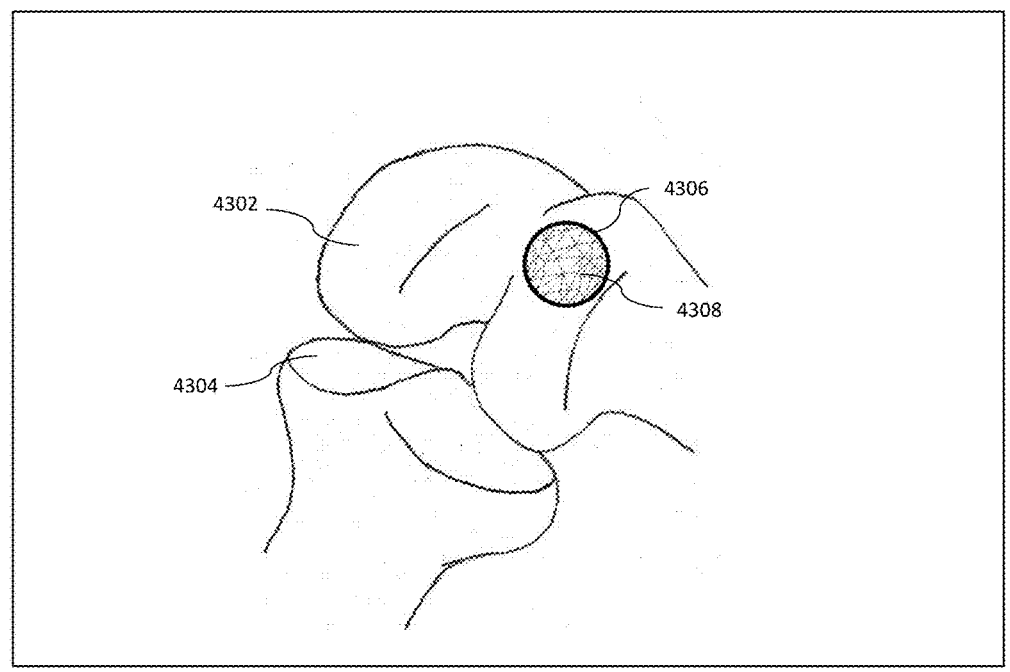
FIG. 43 is a diagrammatic depiction of a MXUI provided by system of FIG. 1 during registration of a distal femur in a knee replacement procedure.

FIG. 43 shows an exemplary embodiment of a MXUI shown to the surgeon 4208 via the AR headset 3600 during a knee replacement surgery with the knee exposed. A topographical map of the femoral condyles 4302 and tibial plateau 4304 can be generated by scanning with the depth sensor 3906 in the AR headset 3600 or by use of the stereoscopic cameras 3904 and SLAM. The knee would be flexed through a range of motion and the surgeon 4208 would adjust his vantage point to allow as much visualization of the condyles as possible. A circle 4306 at the center of the field of view is used by the surgeon 4208 to "paint" the condyles during the registration process and is used as a mask for the mapping algorithm. This circle may be coincident with the projection field of a structured light projector used to enhance the speed and precision of mapping. As surfaces are mapped, a virtual 3D mesh 4308 of mapped areas may be projected onto the articular surfaces to guide the surgeon 4208 and provide a visual confirmation of the quality of the surface registration. An algorithm is then used to determine the lowest point on the articular surfaces of the distal femur and the proximal tibia to determine the depth of the distal femoral and proximal tibial resections. The ideal implant sizes can be determined from the topographical map.

Figure 58A:
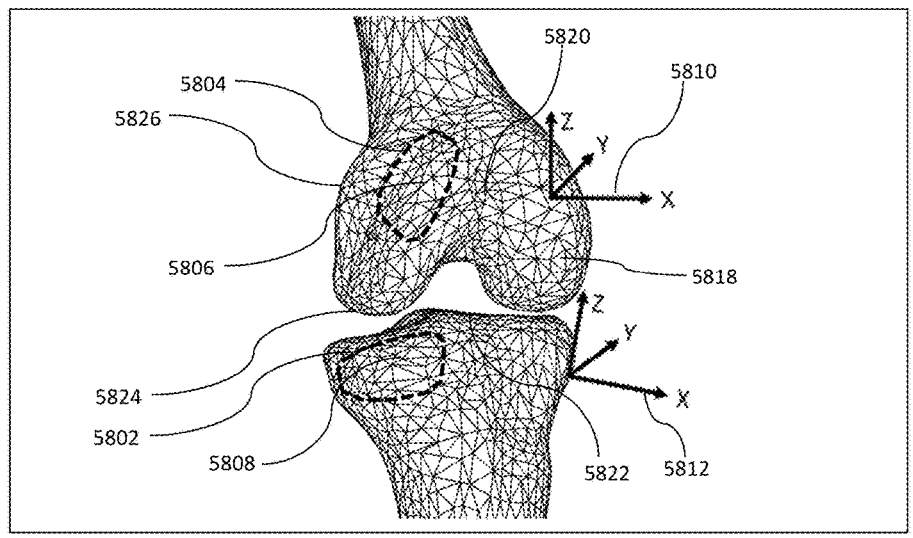
FIG. 58A is a diagrammatic depiction of a knee showing exemplary regions for surface mapping in a reference position.
Figure 58B:
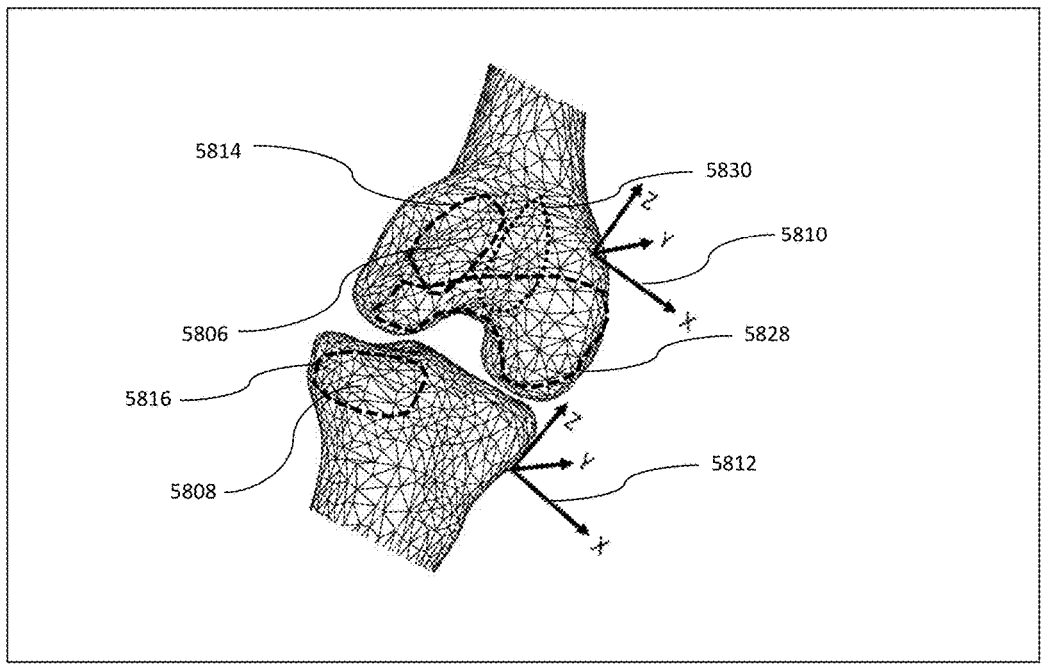
FIG. 58B is a diagrammatic depiction of a knee showing exemplary regions for surface mapping in a displaced position.
Figure 58C:
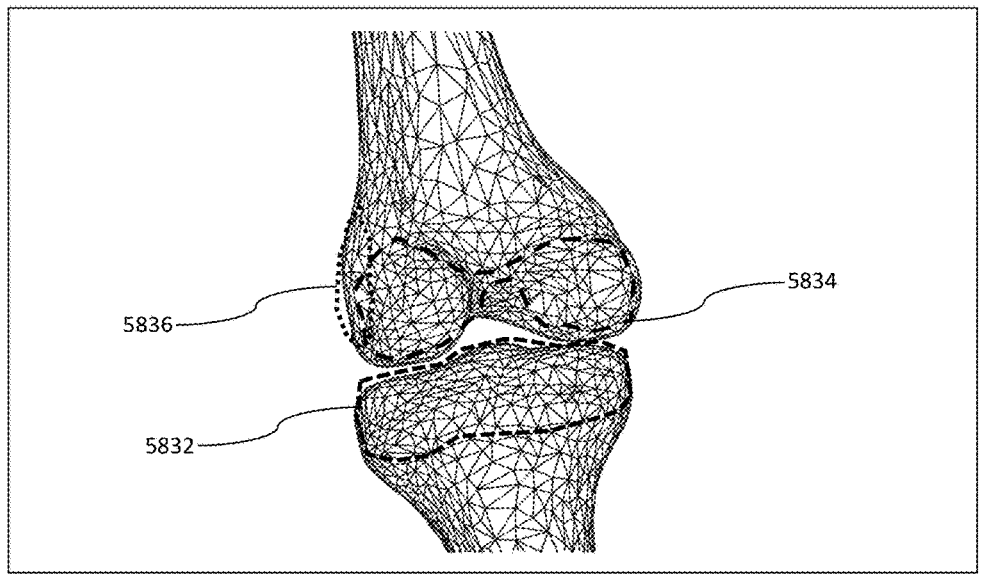
FIG. 58C is a diagrammatic depiction of a knee showing exemplary regions for surface mapping.

In another exemplary embodiment, the system 10 may use the topographical maps of the femur 4204 and tibia 4206 to track the poses of the respective bones (4204, 4206) in lieu of attaching a fiducial marker to the bones (4204, 4206). In a preferred embodiment, the user 106 may select regions of the bones (4204, 4206) that will remain visible as the knee is flexed and extended. Referring to FIGS. 58A-C, the user 106 may select to map the antero-medial aspect of the tibia 5808, or the antero-medial aspect of the distal femur 5806, creating reference 3-dimensional surface maps 5802 and 5804, respectively. These regions are visible through the typical skin incision. Customary retracting instruments and techniques may be used to maintain visibility. The system 10 may store the reference 3-dimensional maps 5802 and 5804 as point clouds, as mathematical surfaces, or by other means. The system 10 may create tibial reference frame 5812 and femoral reference frame 5810 relative to the sensor suite 210 and record the initial pose of the surface maps 5802 and 5804 to reference frames 5812 and 5810, respectively. The user 106 may register additional reference points or structures on the same bone or rigid body, whose pose the system 10 records relative to the reference frame 5812 or reference frame 5810. The system 10, using sensor suite 210, continuously re-scans the same sections of the anatomy and creates displaced 3-dimensional surface maps 5816 and 5814 for the tibia and femur, respectively. Then comparing each displaced surface map 5816, 5814 to the corresponding reference surface map 5802, 5804 created for the same surface, the system 10 determines the geometric rotation and translation required to align the displaced and reference surface maps for best fit. The system 10 then applies the same rotation and translation to all stored reference points and structures on the rigid body of the femur 4204 or tibia 4206, calculating the current pose of all such points and structures relative to the reference frame of sensor suite 210.

Figure 55:
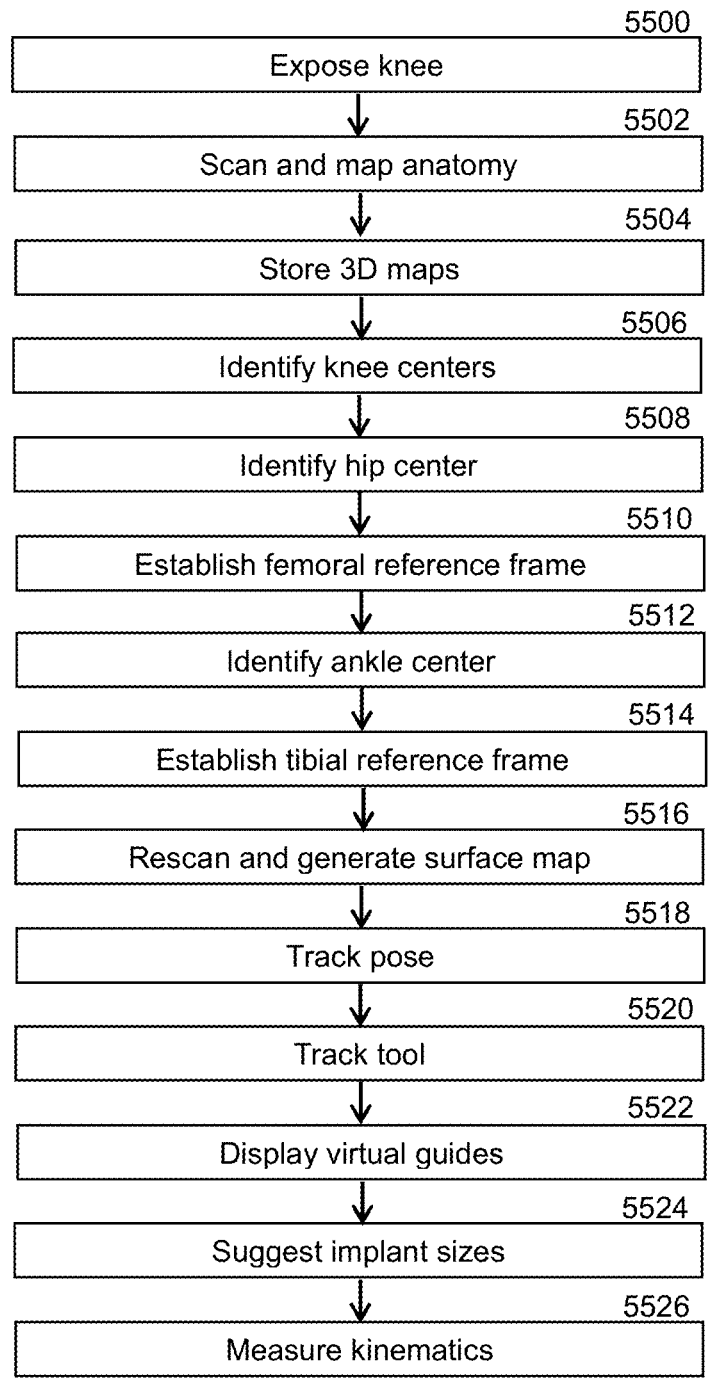
FIG. 55 is a flowchart showing an exemplary method of navigating a knee replacement procedure.

FIG. 55 depicts a flowchart showing an exemplary method for using the system to navigate a knee replacement procedure. The user (106) first exposes the knee to visualize the bony anatomy (5500). The sensor suite 210 then scans the antero-medial aspect of the distal femur 5806 and the antero-medial aspect of the proximal tibia 5808 (5502). From these surfaces, reference 3-dimensional surface maps 5802, 5804 are stored (5504). The system may optionally scan and map larger regions of the femoral condyles 5818, trochlea 5820, tibial plateau 5822, posterior condyles 5824, or epicondyles 5826. From these expanded surface maps 5828, 5830, 5832, 5834, 5836 respectively, and optionally using external anatomic data, the system 10 identifies the center on the distal femur 4204 and the center of the proximal tibia 4206 (5506). The femur is moved through a range of motion whilst scanning the distal femur 5806 to determine the center of rotation of the femur about the hip as a proxy for the center of the hip relative to the mapped distal femoral anatomy 5804 (5508). The user 106 then positions the knee at 90° flexion by arranging the lower leg 5112 approximately perpendicular to the femur 4204. With the knee flexed, the system 10 uses its sensor suite 210 to scan the distal femur 5806 and lower leg 5112, identifying its approximate central axis 5114. Alternatively, the system 10 uses its sensor suite 210 to scan the distal femur 5806 and proximal tibia 5808 as the knee is flexed through a 90 degree range of motion to identify an average flexion axis of the knee. The system 10 then establishes a reference frame 5810 for the femur 4204 relative to the sensor suite 210 with its origin at the center of the distal femur, with a first axis extending toward the center of the hip, a second axis parallel to the axis of the lower limb 5114, and a third axis defined as the normal to the first and second axes (5510). Alternatively, the system establishes a reference frame 5810 for the femur 4204 relative to the sensor suite 210 with its origin at the center of the distal femur, a first axis extending toward the center of the hip, a second axis parallel to the flexion axis of the knee and a third axis defined as the normal to the first and second axes. The locations of the posterior condyles relative to the tibia are recorded, and an axis is constructed between them. The system 10 generates a surface map of a section of the dorsal surface of the foot for the purpose of tracking its pose. In alternative embodiments, the foot may be tracked via a marker affixed to the skin or overlying drapes, wrappings, or boot. The foot is moved through a range of motion to determine its center of rotation as a proxy for the center of the ankle relative to the mapped proximal tibial anatomy (5512). The mechanical axis of the tibia is then constructed between the proximal tibia and ankle centers and establishes a reference frame 5812 for the tibia 4206 relative to the sensor suite 210 with its origin at the center of the proximal tibia, with a first axis extending toward the center of the hip, a second axis parallel to the axis of the lower limb 5114, and a third axis defined as the normal to the first and second axes (5514). Alternatively, the system establishes a reference frame 5812 for the tibia 4206 relative to the sensor suite 210 with its origin at the center of the proximal tibia, a first axis extending toward the center of the ankle, a second axis parallel to the flexion axis of the knee and a third axis defined as the normal to the first and second axes. Then, repeatedly scanning the exposed distal femur 5806 and proximal tibia 5808, the system 10 generates displaced surface maps 5814 and 5816 for each scan (5516). With each successive scan, the system can compare the displaced surface maps 5814 and 5816 to the original surface maps 5804 and 5802 for the corresponding region on the distal femur 5806 and proximal tibia 5808, respectively. Based on this comparison, the system 10 can track the pose of the femur 4204 and tibia 4206 relative to sensor suite 210 by determining the translation and rotation required to align the displaced surface maps 5814 and 5816 with the reference surface maps 5804 and 5802 (5518). The system 10 then calculates and displays the angles and depths of resection on the distal femur and proximal tibia by simultaneously tracking the respective mapped anatomic surface and a cutting tool or guide (5520). The system 10 may then display virtual guides to assist the user 106 in aligning the cutting tool or guide with a user-defined target angle or depth (5522). The system 10 may suggest implant sizes to the user 106 based on external implant data (5524). Following placement of implants or trial implants, the system 10 may track the femur and tibia throughout a range of flexion and measure the relative rotation of the femur and tibia about one or more axes, representing, for example, axial rotation or varus/valgus rotation (5526).

Optionally, the system 10 may use the mapped topography to automatically determine the respective centers of the distal femur 5804 (e.g., by identifying the most distal point on the trochlea or the center of a line through the widest part of the condyles) or proximal tibia 5802 (e.g., by calculating the centroid of the plateau). Optionally, the identification of the center point may be supplemented by external data such as a library of anatomic topographical maps in which the center had been identified, allowing the system 10 to calculate the center point in cases in which the anatomy was partly obscured, preventing mapping of the entire surface.

Figure 56:
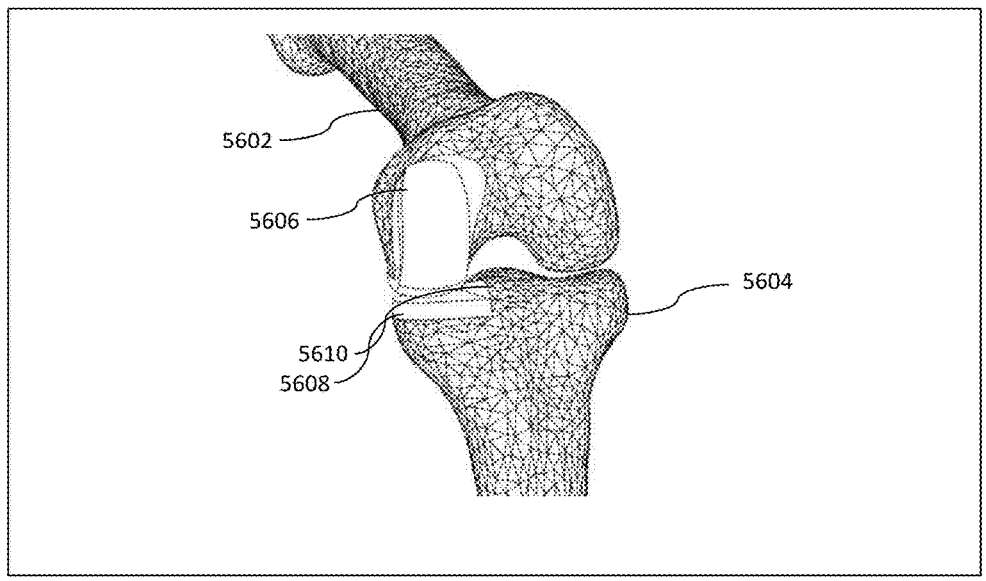
FIG. 56 is a diagrammatic depiction of a knee with unicondylar implants.

FIG. 56 depicts a knee with implanted unicondylar components. One compartment of each of the femur 5602 and tibia 5604 has been resected. A femoral implant 5606 and a tibial implant 5608 have been implanted. In one exemplary embodiment, the system 10 tracks and records the relative motion of the native femur 5602 and tibia 5604. Then, scanning and mapping the surfaces of the implants (5606, 5608) using cameras 206, the system 10 may calculate the paths of the implant surfaces following the recorded tibiofemoral motions. The system 10 may also map the remaining exposed bone 5610 and detect impingement between implants (5606, 5608) and bone 5610. The volume representing the overlap between interfering bodies may be calculated and overlaid as a virtual model in the display device 104. The system 10 may also highlight impingement sites in the display device 104. For example, the femoral implant 5606 may impinge on the ridge of tibial bone adjacent to the sagittal resection plane 5610, or this ridge may impinge on the femoral bone adjacent to the femoral implant 5606. If at least one contacting surface is a bone, the user 106 may elect to trim the bone to change the contact point. If at least one contacting surface is on an implant, the user 106 may elect to adjust the position of the implant to reduce impingement.

Figure 57:
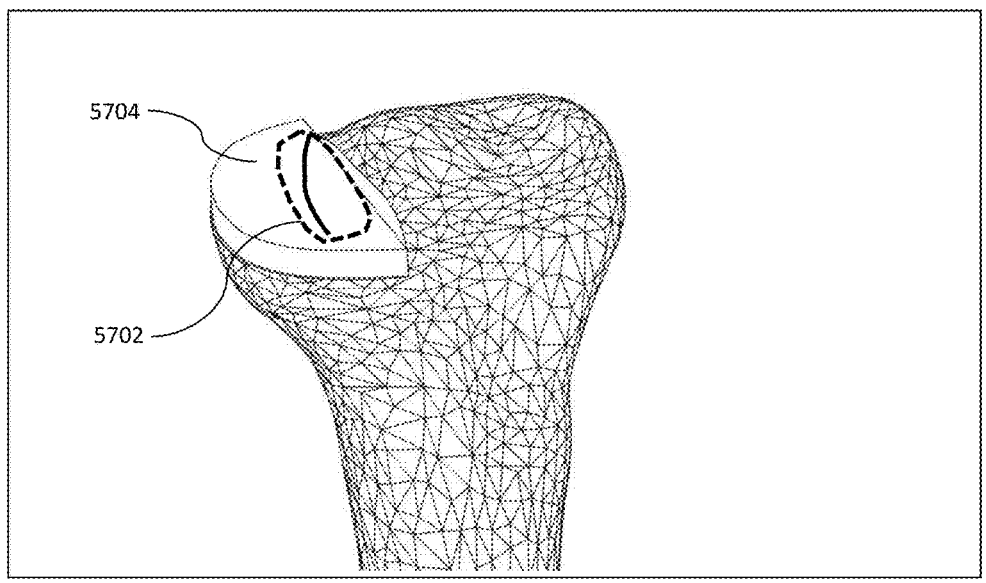
FIG. 57 is a diagrammatic depiction of a tibia with unicondylar implant.

Referring to FIG. 57, the system 10, having recorded the native tibio-femoral kinematics, may display to the user 106 the locus of the inter-implant contact point 5702 and a pre-defined safe zone 5704, projected onto the surface of the implant.

Figure 44:
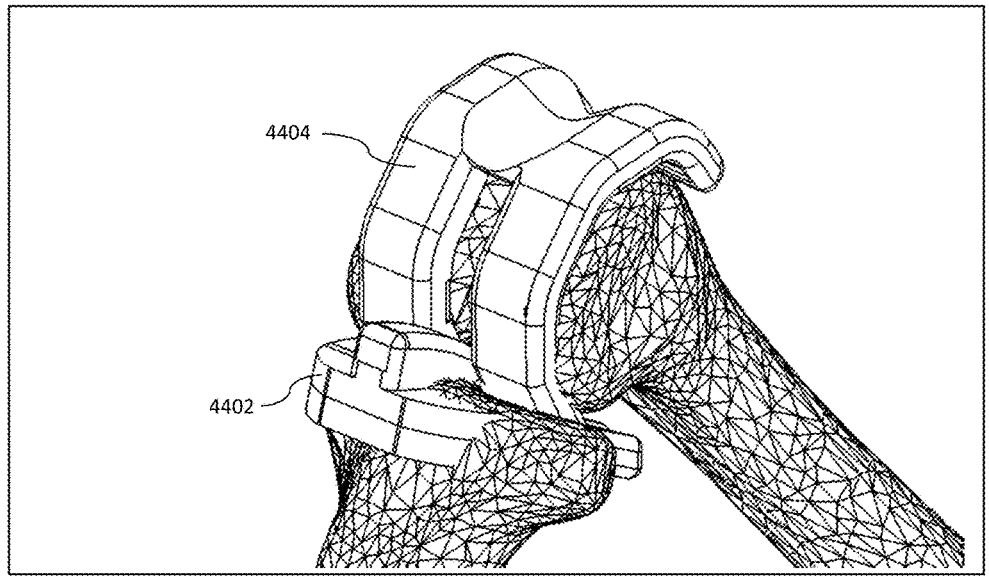
FIG. 44 is a diagrammatic depiction of a MXUI provided by system of FIG. 1 during resection plane planning in a knee replacement procedure.

Referring to FIG. 44, a virtual tibial implant 4402 and virtual femoral implant 4404 can be displayed in a MXUI shown to the surgeon 4208 via the AR headset 3600. The surgeon 4208 may switch the sizes and adjust the position of these virtual models until satisfied. In another embodiment, the virtual tibial implant may be displayed during preparation of the tibia for broaching to provide a guide for the rotational alignment of the tibial component.

Figure 45:
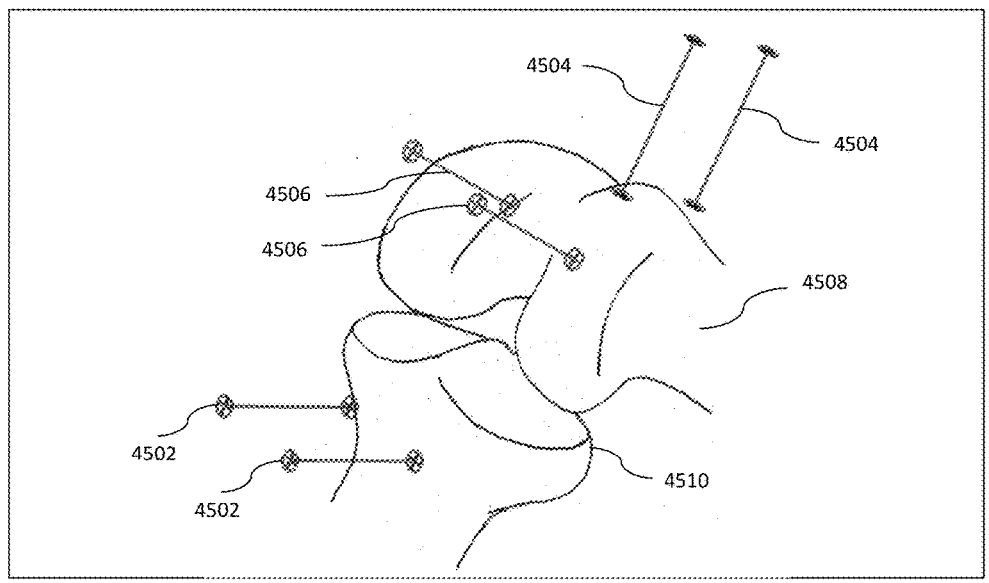
FIG. 45 is a diagrammatic depiction of a MXUI provided by system of FIG. 1 during placement of pins for location of cutting blocks in a knee replacement procedure.

Referring to FIG. 45, virtual guides 4502 for location of pins for the tibial cutting block are displayed in a MXUI shown to the surgeon 4208 via the AR headset 3600. Virtual guides 4504 for location of pins for the distal femoral cutting block are displayed. Virtual guides 4506 for location of pins for the 4 in 1 cutting block are displayed. Placement of the actual pins is guided by aligning them with the virtual guides 4502, 4504 or 4506. The femur 4508 and tibia 4510 may then be resected by placing cutting blocks on these pins.

Figure 46:
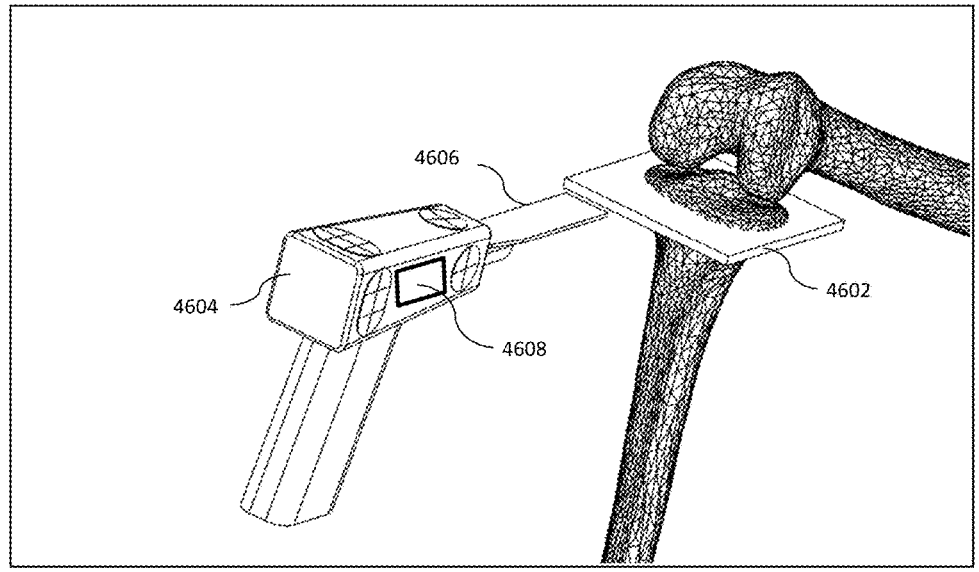
FIG. 46 is a diagrammatic depiction of a MXUI provided by system of FIG. 1 during tibial resection in a knee replacement procedure.

FIG. 46 depicts an alternative embodiment of the MXUI shown in FIG. 45 wherein a virtual guide 4602 is used to display the ideal plane of resection and the surgeon 4208 may resect the bone directly by alignment of the actual saw blade with the virtual guide 4602. Alternatively, in the case of a tracked saw 4604, the surgeon 4208 may resect the bone by alignment of a virtual saw blade 4606 with the virtual guide 4602. Virtual text 4608 showing the varus/valgus angle, flexion angle and depth of each resection may be displayed numerically when relevant.

Figure 47:
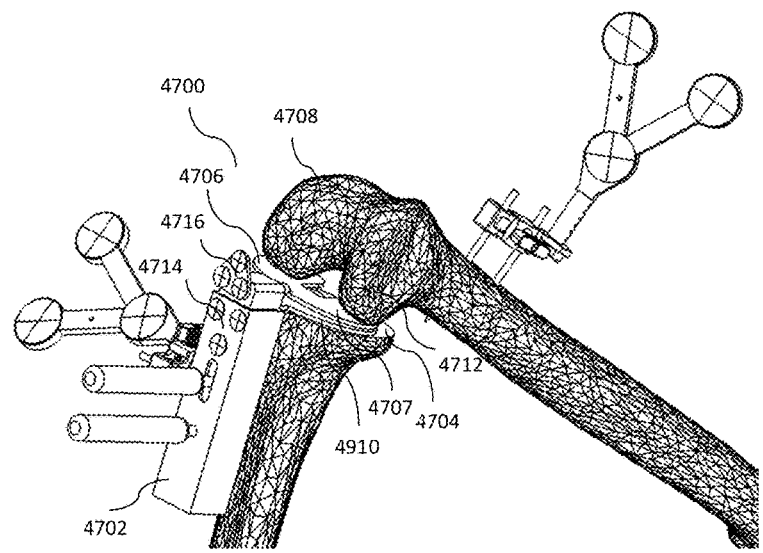
FIG. 47 is a perspective front view of a diagrammatic depiction of a knee balancing device that is optionally included in the system of FIG. 1 in use during a knee replacement procedure.
Figure 49:
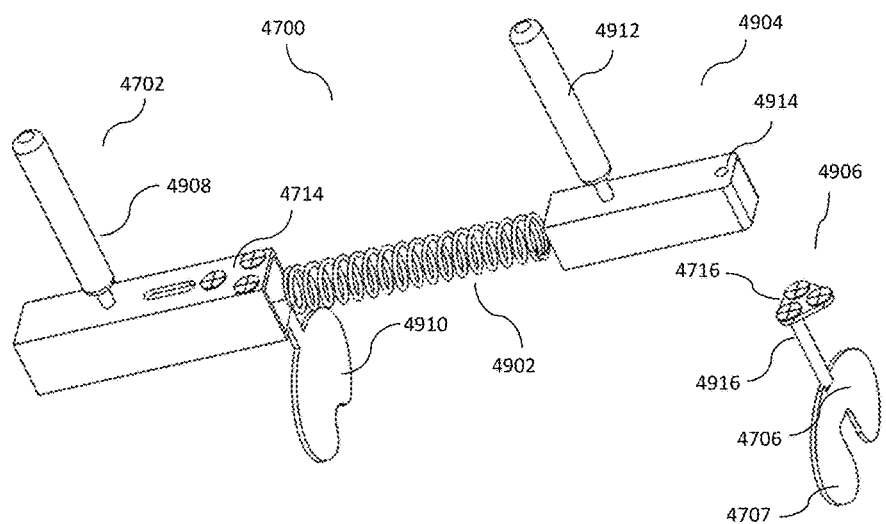
FIG. 49 is a perspective front view of the knee balancing device shown in FIG. 47.

FIGS. 47 and 49 depict a knee balancing device 4700 that may be optionally included in the system 10 having a base element 4702, a spring 4902, a condylar element 4904, and a condylar plate 4906. The base element 4702 includes a handle 4908, a target 4714 and a tibial plate 4910. The condylar element 4904 includes a handle 4912 and a cylindrical bearing hole 4914. The condylar plate 4906 includes a cylindrical bearing shaft 4916, a target 4716 and two paddles 4706 and 4707. The condylar plate 4906 pivots about a cylindrical bearing 4916, which allows medial/lateral tilt of the condylar plate 4906 relative to the base plate 4910. In an alternative embodiment, the bearing 4916 may be a ball-type allowing medial/lateral and flexion/extension tilt of the condylar plate 4906. In another embodiment, the condylar plate 4906 may be contoured to match the topography of the bearing surface of a tibial implant. In another embodiment, the design could include two fully independent condylar elements each with a rigidly integrated distraction paddle and a marker.

Referring to FIG. 47, the tibial plate 4910 is seated on the resected tibia 4704, and the distraction paddles 4706 and 4707 maintain contact with the medial femoral condyle 4708 and the lateral femoral condyle 4712 respectively. The distraction paddles 4706 and 4707 are pushed by the spring 4902 and pivot about an anteroposterior axis to provide a nearly equal and constant distraction force between each femoral condyle (4708, 4712) and the tibia 4704. The base element 4702 and distraction paddles (4706, 4704) include optical markers (4714, 4716) which allow the software to measure the degree of distraction of each femoral condyle (4708, 4712).

Figure 48:
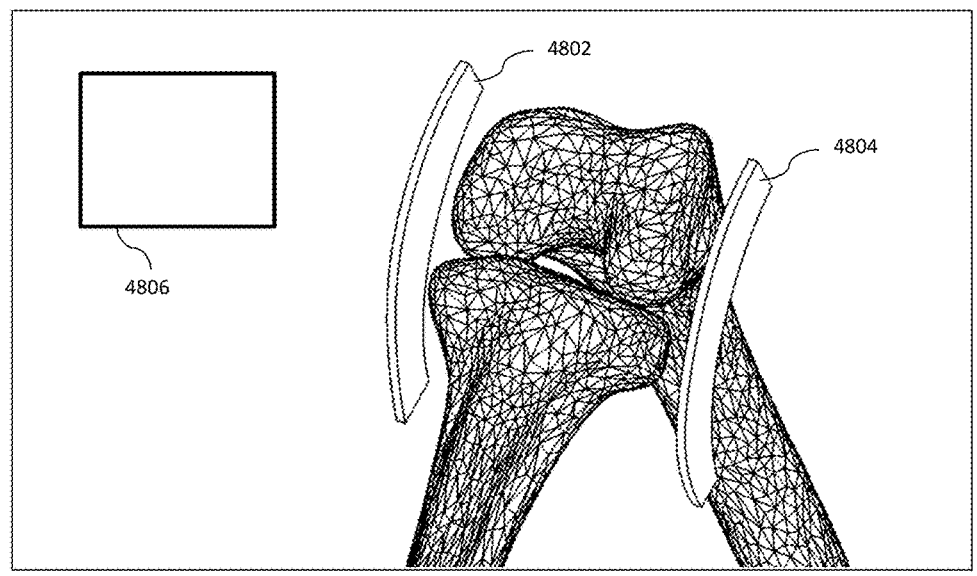
FIG. 48 is a diagrammatic depiction of a MXUI provided by system of FIG. 1 during a balancing assessment in a knee replacement procedure.

As the knee is flexed through a range of motion, the position of each target is tracked, as is the pose of the tibia and femur. This data is used to generate a plot of medial and lateral laxity as a function of flexion angle. This information is used to calculate the ideal location of the distal femoral cutting block location pins to achieve balance through the range of motion of the knee or to guide the user in removing osteophytes or performing soft tissue releases to balance the knee through its range of motion. This plot may be displayed in a MXUI as shown in FIG. 48 in which a first three-dimensional arc 4802 represents the medial laxity and a second three-dimensional arc 4804 represents the lateral laxity through the range of motion of the knee. The numerical values at the current flexion angle of the actual knee can be displayed as virtual text 4806.

VII. Other Medical Procedures

Figure 10:
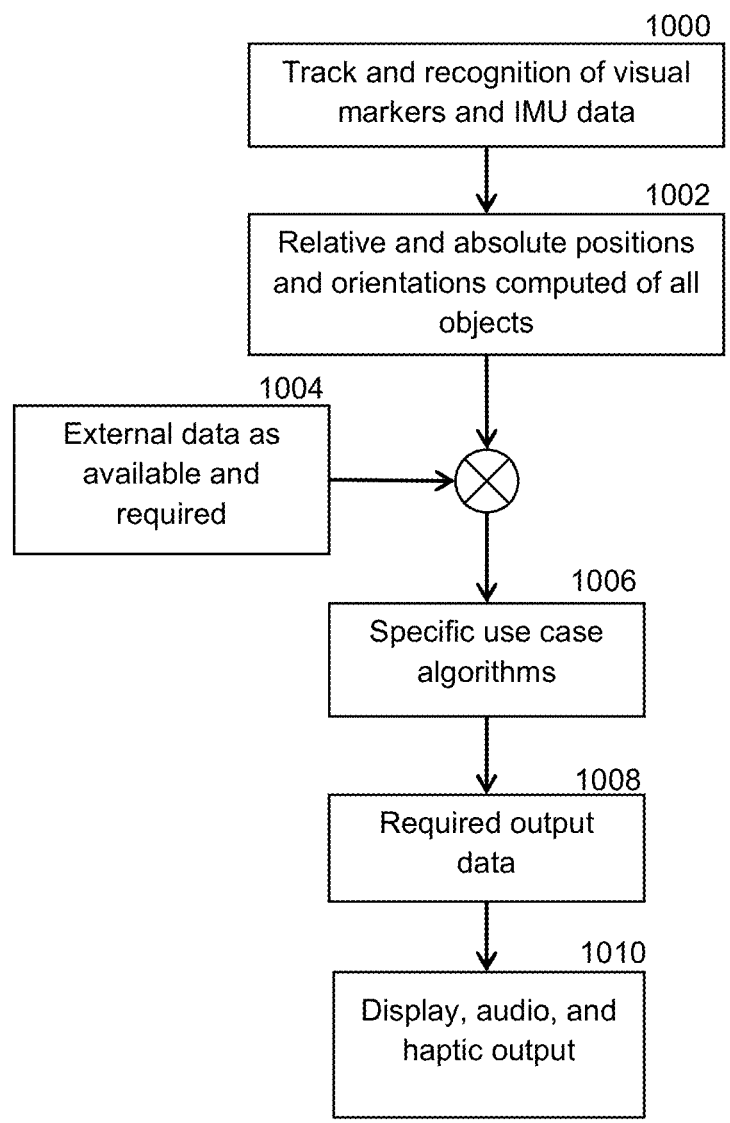
FIG. 10 is a flowchart showing a method of using the system of FIG. 1 to perform a general medical procedure in accordance to the principles of the present invention.

Referring to FIG. 10, the present invention further provides a method of using the system 10 to perform other surgical procedures (specific examples are provided below). The method includes data collection (1000) that includes, but is not limited to, tracking and recognition of visual markers and IMUs. This data is used to determine relative and/or absolute orientation and position of multiple items in the work view (1002). External data (1004) is brought into the algorithm. Algorithms are used to process the data for specific use cases (1006) and determine the required output (1008). This data is used in an augmented reality AR or virtual reality VR output display (1010) to assist the medical professional.

For example, the method can be used for total hip arthroplasty. The markers (e.g., 100, 108, 110, etc.) for anatomic landmarks and tools are used for data collection (1000) and the determination of position and orientation (1002) of hip and surgical tools. Algorithms (1006) are used to determine solutions including, but not limited to, component positioning, femoral head cut, acetabulum positioning, screw placement, leg length determination, and locating good bone in the acetabulum for revision setting.

The method can also be used for total knee arthroplasty. The markers (e.g., 100, 108, 110, etc.) for anatomic landmarks and tools are used for data collection (1000) and the determination of position and orientation (1002) of knee, tibia and surgical tools. Algorithms (1006) are used to determine solutions including but not limited to location, angle and slope of tibial cut, placement and fine-tuning of guide, avoidance of intra-medullary guide and improvement of femoral cuts.

The method can be used for corrective osteotomy for malunion of distal radial fractures. The markers (e.g., 100, 108, 110, etc.) for anatomic landmarks and tools are used for data collection (1000), which may be combined with pre-operative CT scan data for the determination of position and orientation (1002) of malunion and surgical tools. Algorithms (1006) are used to determine solutions including but not limited to location of osteotomy, angle of cut and assessment of results.

The method can be used for corrective osteotomy for malunion of arm bones including the humerus, distal humerus, radius and ulna with fractures that can be complicated and involve angular and rotational corrections. The markers (e.g., 100, 108, 110, etc.) for anatomic landmarks and tools are used for data collection (1000), which may be combined with pre-operative CT scan data for the determination of position and orientation (1002) of malunion and surgical tools. Algorithms (1006) are used to determine solutions including but not limited to location of osteotomy site, angle of cut, degree of correction and assessment of results.

The method can be used for distal femoral and proximal tibial osteotomy to correct early osteoarthritis and malalignment. The markers (e.g., 100, 108, 110, etc.) for anatomic landmarks and tools are used for data collection (1000), which may be combined with pre-operative CT scan data or long-leg X-ray imagery for the determination of position and orientation (1002) of osteotomy location and scale and surgical tools. Algorithms (1006) are used to determine solutions including but not limited to location of osteotomy site, angle of cut, degree of correction and assessment of results.

The method can be used for peri-acetabular osteotomy for acetabular dysplasia. The markers (e.g., 100, 108, 110, etc.) for anatomic landmarks and tools are used for data collection (1000), which may be combined with pre-operative CT scan data for the determination of position and orientation (1002) of osteotomy location and surgical tools. Algorithms (1006) are used to determine solutions including but not limited to location of osteotomy site, angulation, degree of correction and assessment of results.

The method can be used for pediatric orthopedic osteotomies similar to the previous embodiments. The markers (e.g., 100, 108, 110, etc.) for anatomic landmarks and tools are used for data collection (1000), which may be combined with pre-operative CT scan data for the determination of position and orientation (1002) of osteotomy location and surgical tools. Algorithms (1006) are used to determine solutions including but not limited to location of osteotomy site, angle of cut, degree of correction and assessment of results.

The method can be used for elbow ligament reconstructions including but not limited to radial collateral ligament reconstruction (RCL) and UCL reconstruction (Tommy-John). The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including but not limited to precise localization of tunnel placement and assessment of results.

The method can be used for knee ligament reconstructions including but not limited to MCL, LCL, ACL, PCL and posterolateral corner reconstructions. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including but not limited to precise localization of tunnel placement, tunnel depth, tunnel angle, graft placement, and assessment of results.

The method can be used for ankle ligament reconstructions including but not limited to reconstruction to correct instability. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including but not limited to precise localization of tunnel placement, tunnel depth, tunnel angle, and assessment of results.

The method can be used for shoulder acromioclavicular (AC) joint reconstruction surgical procedures including by not limited to placement not tunnels in the clavicle. The markers (e.g., 100, 108, 110, etc.) for anatomic landmarks and tools are used for data collection (1000), which may be combined with pre-operative CT scan or MRI data for the determination of position and orientation (1002) of isometric points for ligament reconstruction and surgical tools. Algorithms (1006) are used to determine solutions including but not limited to precise localization of tunnel placement, tunnel depth, tunnel angle, and assessment of results.

The method can be used for anatomic and reverse total shoulder replacement (TSA and RSA) surgical procedures including revision TSA/RSA. The markers (e.g., 100, 108, 110, etc.) for anatomic landmarks and tools are used for data collection (1000), which may be combined with pre-operative CT scan or MRI data for the determination of position and orientation (1002) of humeral head, related landmarks and surgical tools. Algorithms (1006) are used to determine solutions including but not limited to precise localization of humeral head cut and glenoid bone placement, baseplate and screws, and reaming angle and guide placement for glenoid correction, and assessment of results.

The method can be used for total ankle arthroplasty surgical procedures. The markers (e.g., 100, 108, 110, etc.) for anatomic landmarks and tools are used for data collection (1000), which may be combined with pre-operative CT scan or MRI data for the determination of position and orientation (1002) of tibia, fibula, talus, navicular and other related landmarks and surgical tools. Algorithms (1006) are used to determine solutions including but not limited to precise localization of tibial head cut, anatomic axis determination, and assessment of results.

The method can be used for percutaneous screw placement for pelvic fractures, tibial plateau, acetabulum and pelvis, but not limited to these areas. The markers (e.g., 100, 108, 110, etc.) for anatomic landmarks and tools are used for data collection (1000), which may be combined with pre-operative CT scan or MRI data for the determination of position and orientation (1002) of anatomic and other related landmarks and surgical tools including screws. Algorithms (1006) are used to determine solutions including but not limited to precise localization of bones receiving screws, surrounding anatomy and soft tissue features to be avoided, localization of screws, angle of insertion, depth of insertion, and assessment of results.

The method can be used for in-office injections to areas including but not limited to ankle, knee, hip, shoulder and spine. The markers (e.g., 100, 108, 110, etc.) for anatomic landmarks and tools are used for data collection (1000), which may be combined with pre-operative CT scan or MRI data for the determination of position and orientation (1002) of related landmarks and surgical tools. Algorithms (1006) are used to determine solutions including but not limited to precise localization of injection location, angulation, and depth in order to maximize effect and minimize interaction with internal organs and anatomy.

The method can be used for pedicle screw placement for spinal fusion procedures including the lumbar and thoracic spine, but not limited to these areas. The markers (e.g., 100, 108, 110, etc.) for anatomic landmarks and tools are used for data collection (1000), which may be combined with pre-operative CT scan or MRI data for the determination of position and orientation (1002) of anatomic and other related landmarks and surgical tools including screws. Algorithms (1006) are used to determine solutions including but not limited to precise localization of bones receiving screws, opening of the cortex, cranial-caudal angulation or similar, medio-lateral inclination, screw insertion trajectory, depth of insertion, and assessment of results.

The method can be used for visualization of alternate spectrum imagery including but not limited to infrared, ultraviolet, ankle, knee, hip, shoulder and spine. The markers (e.g., 100, 108, 110, etc.) for anatomic landmarks and tools are used for data collection (1000), which may include, but is not limited to, dual color camera(s) with alternate spectrum sensitivities and/or injection dye for highlight of the patient's features for the determination of position and orientation (1002) of related landmarks and surgical tools and position, location, and type of anatomic features more readily visible in alternate spectrums including nerves, tumors, soft tissues and arteries. Algorithms (1006) are used to determine solutions including but not limited to precise localization of nerves, tumors, soft tissues of interest, arteries and other features of interest that can be enhanced with this technique.

The method can be used for tumor diagnostic, staging and curative surgical procedures. The markers (e.g., 100, 108, 110, etc.) for anatomic landmarks and tools are used for data collection (1000), which may be combined with pre-operative CT scan or MRI data for the determination of position and orientation (1002) of tumor location and surgical tools. Alternately during diagnostic surgery, localization of the tumor with respect to anatomic landmarks can be performed. Algorithms (1006) are used to determine solutions including but not limited to location of tumor site and size extent, removal guidance and assessment of results.

The method can be used for projection of a visible or invisible but camera visible point of light on objects of interest in the field of regard, including but not limited to bony landmarks, nerves, tumors, and other organic and inorganic objects. The markers (e.g., 100, 108, 110, etc.) are used to augment or supersede external data sets for anatomic data, and can be used in place of a physical pointer or tool as has been described previously. The point of light can be displayed from the user's head display or other location. The point of light can also be manifested as a pattern or other array of lights. These light(s) highlight features on the patient for determination of position and orientation (1002) of related landmarks and surgical tools, as well as augmentation of data sets including but not limited to fluoroscopy, CT scans and MRI data. Algorithms (1006) are used to determine solutions previously described but with the alternate or added selection option.

The method can be used for minimally invasive positioning of implants and inserting locking screws percutaneously. A marker (e.g., 100, 108, or 110, etc.) is mounted on the proximal end of an intramedullary nail. Another marker (e.g., 100, 108, or 110, etc.) is mounted on the cross-screw insertion tool. A virtual model of the nail is displayed including the target trajectory for the locking cross-screw. The surgeon is able to insert the cross screw by aligning the virtual cross-screw with the target trajectory. In another embodiment, the same method can be applied to the external fixation plates. In this case virtual locking plate with a plurality of locking screw trajectories, one for each hole, would be displayed.

VIII. Database of Trackable Instruments and Equipment

Figure 29:
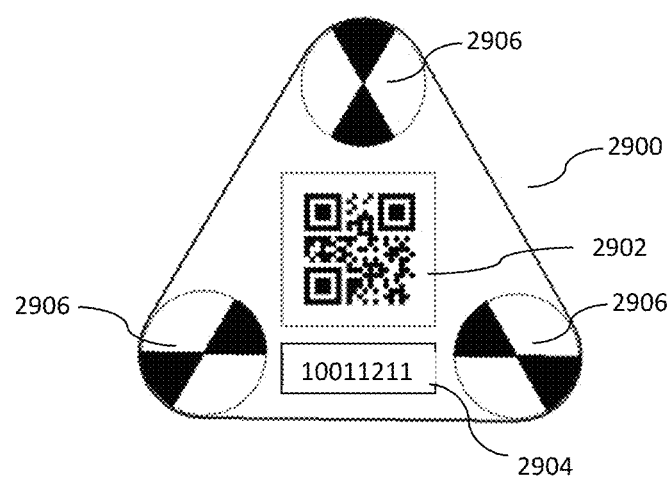
FIG. 29 shows a front view of a diagrammatic depiction of an equipment identification and tracking label that is optionally included in the system of FIG. 1.

The present invention optionally includes the construction of an electronic database of instruments and equipment in order to allow the AR headset 3600 to identify what instruments are present in the surgical field or in the operating room area. Referring to FIG. 29, a serialized tracking label 2900 is optionally included in the system to facilitate the construction of such database. The serialized tracking label 2900 includes a machine-readable serial number code 2902, a human readable serial number 2904 and a set of optical features which facilitate six-degree of freedom optical pose tracking such as a plurality of fiducials 2906. In one embodiment, the machine-readable number code 2902 pattern can be imaged by the camera(s) 3904 of the AR headset 3600 and used alone to determine pose and position of the medical instrument using machine vision algorithms. In another embodiment, the serial number image 2904 can be imaged by the camera(s) 3904 and used alone to determine pose and position of the medical instrument using machine vision algorithms. In yet another embodiment, the entire physical model of the tracking label 2900 can be imaged by the camera(s) 3904 and used alone to determine pose and position of the medical instrument using machine vision algorithms. In another embodiment, the tracking label 2900 may be comprised or contain a wireless RFID tag for non-optical identification of equipment in a kit that can be then verified automatically using optical recognition.

Figure 30:
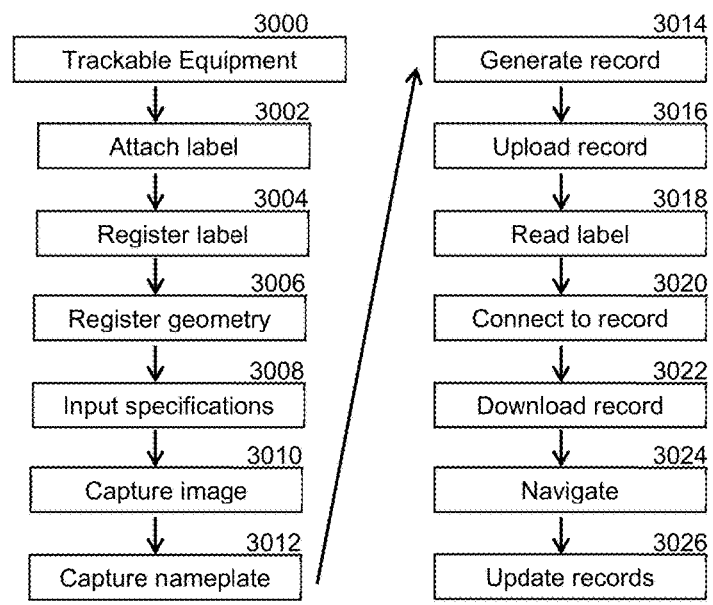
FIG. 30 is a flowchart of a method for registering, sharing and tracking medical equipment using the system of FIG. 1 in accordance to the principles of the present invention.

Referring to FIG. 30, a flowchart showing a system for registering item type and physical parameters of equipment and storing and sharing this data for use in surgery using an augmented reality headset is provided. In this exemplary embodiment, serialized trackable labels are pre-printed on durable self-adhesive material. The label is attached (3002) to an item of equipment (3000), which could be but is not limited to a C-arm, impactor, pointer, or any other equipment used in the procedure, in a location which will be most advantageously viewed during a surgical procedure or in the preparatory effort leading to the procedure (i.e. back table operations). The label is then registered (3004) by viewing with the camera(s) 3904, identifying the label, and initiating a database record associated with that serial number. Geometry of interest relating to the item of equipment can also be registered (3006) and stored relative to the trackable sticker. For example, in the case of a C-arm, a registration stylus may be used to register three points around the perimeter of the face of the imager and a point representing the origin of the X-ray beam source. This provides a coordinate frame, orientation (pose) data, and position data of the X-ray beam source with respect to the AR headset 3600 coordinate frame for use by the AR headset's 3600 algorithms. In one alternate embodiment, the cameras 3904 are stereo cameras and are used to scan and recognize C-arm geometry by recognition of key features such as the cylindrical or rectangular surface of the imager. Additional relevant specifications (3008) for the item of equipment can be entered into the record and includes but is not limited to the equipment type and model, calibration due date, electronic interface parameters and wireless connectivity passwords. An image of the device is captured 3010 with the camera(s) 3904. An image of the equipment label (3012) of the device is captured. All these items are added to the completed record (3014), which is currently local to the AR headset 3600. The record is then time-stamped and shared with a central database (3016). This may be located on a local server within the hospital system or in any remote server including any cloud based storage via the internet. Upload of the database may be done via Wi-Fi common network protocols or other art-disclosed means. The above actions may be performed by a company representative, a technician employed by the hospital, or any other trained individuals. To prevent poorly registered equipment entering the database, administrator privileges may be required to capture a record.

When an item of equipment is being used in surgery, the camera(s) 3904 are utilized to recognize the label as a trackable item of equipment and read the serial number (3018). The AR headset 3600 can then connect (3020) to the database and download the equipment record (3022). The equipment can thus be used in a six-degree of freedom trackable manner during the surgery (3024). If applicable, to the equipment with the data labels, the records (3026) may also be updated with data specific to the equipment itself, for example, upload images captured by the equipment during a surgery or capture logs of equipment activity during a surgery in a log. Log entries describing the use of the equipment in the surgery can be added to the database and to the patient record showing utilization of the equipment. The database thus generated can be mined for various reasons such as retrieving usage of defective equipment.

The system may also be used to recognize surgical instruments and implants encountered during surgery. A database of CAD models of instruments and equipment to scale is held in memory. During a procedure, SLAM or similar machine vision algorithms can capture topography of items in the scene and compare to the database on instruments and equipment. If a match is found, system can then take actions appropriate such as tracking the position and orientation of instruments relative to the patient and other instruments being used in surgery or enter a mode relevant to use of that instrument. For example, in a hip replacement procedure, if an acetabular impactor is detected, the mode for cup placement navigation is entered.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

Unless stated otherwise, dimensions and geometries of the various structures depicted herein are not intended to be restrictive of the invention, and other dimensions or geometries are possible. Plural structural components can be provided by a single integrated structure. Alternatively, a single integrated structure might be divided into separate plural components. In addition, while a feature of the present invention may have been described in the context of only one of the illustrated embodiments, such feature may be combined with one or more other features of other embodiments, for any given application. It will also be appreciated from the above that the fabrication of the unique structures herein and the operation thereof also constitute methods in accordance with the present invention.

What is claimed is:

1. A surgical navigation system for tracking anatomic structures without fiducial markers fixed to an anatomy, the system comprising:
   a head-worn display device, to be worn by a user during a surgical procedure, comprising a processor unit, a display generator, a sensor suite having at least one tracking camera or depth sensor, wherein:
   the processor unit is configured to perform a method comprising:
      receive, from the sensor suite during the surgical procedure, topographical data of an exposed surface of an anatomical feature of a bone;
      create a reference surface map of the exposed surface of the the anatomical feature of the bone using the topographical data received from the sensor suite, wherein a topography of the exposed surface of the anatomical feature of the bone remains unchanged and visible during the surgical procedure;
      establish a reference frame relative to the sensor suite for the reference surface map; and
      track, without using pre-operative anatomical data, a pose of the anatomical feature of the bone relative to the head-worn display device during the surgical procedure by:
         creating a displaced surface map of the exposed surface,
         comparing the displaced surface map to the reference surface map of the exposed surface of the feature of the bone,
         determining a rotation and translation required to best fit the displaced surface map with the reference surface map, and
         rotating and translating the displaced surface map and reference frame to align the displaced surface map with the reference surface map for best fit.

2. The surgical navigation system of claim 1, wherein the processor unit is further configured to communicate with the head-worn display to provide a mixed reality user interface comprising stereoscopic virtual images of desired features of surgical tools or implants relative to the anatomical feature of the bone in a field of view of the user.

3. The surgical navigation system of claim 1, where the processor unit is further configured to apply the rotation and translation to all stored reference points and structures on the bone; and calculate a current pose of all such points and structures relative to the reference frame.

4. The surgical navigation system of claim 1, wherein the processor unit is further configured to:
   create additional surface maps of other anatomical features of an anatomical object; and
   construct an anatomical reference frame relative to the bone by using the additional surface maps generated from the other anatomical features of the anatomical object.

5. The surgical navigation system of claim 4, wherein the processor unit is further configured to:

identify one or more approximate axes of one or more of the other anatomical features from the additional surface maps; and
construct the anatomical reference frame using the one or more approximate axes.

6. The surgical navigation system of claim 4, wherein the processor unit is further configured to:
track a pose of the other anatomical features in the additional surface maps during movement of an anatomical object;
calculate one or more approximate rotation axes or points from a path of movement; and
construct the anatomical reference frame using the one or more approximate axes or points.

7. The surgical navigation system of claim 4, wherein the surgical procedure is a knee surgery and the bone is selected from the group consisting of: a femur and a tibia.

8. The surgical navigation system of claim 7, wherein the bone is the femur and the reference frame is aligned with an axis of the femur by:
creating a surface map of a distal surface of the femur;
analyzing the surface map to establish a center of the distal surface of the femur;
moving the femur through a range of motion while tracking a pose of the femur;
determining a center of rotation of the femur based on the tracked pose; and
aligning an axis of the reference frame with a line joining the center of the distal surface of the femur to the center of rotation of the femur.

9. The surgical navigation system of claim 7, wherein the reference frame is aligned with an axis of the femur by flexing a knee while tracking the femur and the tibia using an exposed distal portion of the femur and an exposed proximal portion of the tibia or lower leg to establish a flexion axis of the knee.

10. The surgical navigation system of claim 7, wherein the bone is the tibia and the reference frame is aligned with a mechanical axis of the tibia by:
creating a surface map of a proximal surface of the tibia;
analyzing the surface map to establish a center of the proximal surface of the tibia;
flexing an ankle while scanning a surface of a foot and an exposed proximal portion of the tibia to determine a center of rotation of the ankle about the tibia.

11. The surgical navigation system of claim 10, wherein the reference frame is aligned with a transverse axis of the knee by flexing the knee while scanning an exposed distal portion of the femur and the exposed proximal portion of the tibia or a lower leg to establish a flexion axis of the knee.

12. The surgical navigation system of claim 1, wherein the processor unit is further configured to:
create one or more additional surface maps of other anatomical features of an anatomical object; and
establish a reference frame relative to the sensor suite for the reference surface map, wherein an orientation of the reference frame is based on the one or more additional surface maps.

13. The surgical navigation system of claim 12, wherein the surgical procedure is hip arthroplasty, the bone is a femur, and the exposed surface of the anatomical feature of the bone includes a lesser trochanter of the femur.

14. The surgical navigation of claim 13, wherein the other anatomical features are selected from a group consisting of: a femoral head, a femoral neck, a lower leg, and a combination thereof.

15. The surgical navigation system of claim 12, wherein the surgical procedure is knee arthroplasty, the bone is a tibia, and the exposed surface of the anatomical feature of the bone includes an antero-medial aspect of the tibia.

16. The surgical navigation system of claim 15, wherein the other anatomical features are selected from a group consisting of: a tibial plateau, a lower leg, a dorsal surface of a foot, and a combination thereof.

17. The surgical navigation system of claim 12, wherein the surgical procedure is knee arthroplasty, the bone is a femur, and the exposed surface of the anatomical feature of the bone includes an antero-medial aspect of a distal portion of the femur.

18. The surgical navigation system of claim 17, wherein the other anatomical features are selected from a group consisting of: a most distal point on trochlea, a femoral condyle, a posterior condyle, an epicondyle, a lower leg, and a combination thereof.

19. A surgical navigation system for a hip arthroplasty procedure for tracking anatomic structures without fiducial markers fixed to an anatomy, the system comprising:
a head-worn display device, to be worn by a user during a surgical procedure, comprising a processor unit, a display generator, a sensor suite having at least one tracking camera or depth sensor, wherein:
the processor unit is configured to:
receive, from the sensor suite during the surgical procedure, topographical data of a lesser trochanter;
create a reference surface map of the lesser trochanter using the topographical data received from the sensor suite, wherein a topography of the lesser trochanter remains unchanged and visible during the hip arthroplasty procedure;
establish a reference frame for a femur relative to the sensor suite for the reference surface map; and
track, without using pre-operative anatomic data, a pose of the lesser trochanter relative to the head-worn display device by:
creating a displaced surface map of the exposed surface of the lesser trochanter,
comparing the displaced surface map to the reference surface map of the exposed surface of the lesser trochanter of the femur,
determining a rotation and translation required to best fit the displaced surface map with the reference surface map, and
rotating and translating the displaced surface map and reference frame to align the displaced surface map with the reference surface map for best fit.

20. The surgical navigation system of claim 19, wherein the processor unit is further configured to:
create additional surface maps of a femoral head and a lower leg; and
establish a reference frame relative to the sensor suite for the reference surface map, wherein an orientation of the reference frame is based on the additional surface maps.

21. The surgical navigation system of claim 20, wherein the processor unit is further configured to:
create a surface map of a replaced femoral head; and
calculate a change in the femoral head by comparing the surface map of the replaced femoral head and at least one of the additional surface maps of the femoral head.

22. The surgical navigation system of claim 20, wherein the processor unit is further configured to measure a change in a femoral offset.

23. The surgical navigation system of claim 20, wherein the processor unit is further configured to measure a change in leg length due to a change in a position of the femoral head in the reference frame of the femur.

24. The surgical navigation system of claim 20, wherein the processor unit is further configured to:
   create a reference surface map of an acetabulum;
   create a replaced surface map of a replaced acetabular implant of the acetabulum; and
   measure a change in a position of the acetabulum by comparing the replaced surface map and the reference surface map of the acetabulum.

\* \* \* \* \*